(12) United States Patent
Banet et al.

(10) Patent No.: US 12,121,364 B2
(45) Date of Patent: *Oct. 22, 2024

(54) BODY-WORN MONITOR FOR MEASURING RESPIRATION RATE

(71) Applicant: SOTERA WIRELESS, INC., Carlsbad, CA (US)

(72) Inventors: Matthew Banet, San Diego, CA (US); Devin McCombie, Carlsbad, CA (US); Marshal Dhillon, San Diego, CA (US)

(73) Assignee: SOTERA WIRELESS, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/089,485

(22) Filed: Dec. 27, 2022

(65) Prior Publication Data

US 2023/0210384 A1 Jul. 6, 2023

Related U.S. Application Data

(63) Continuation of application No. 16/827,162, filed on Mar. 23, 2020, now abandoned, which is a (Continued)

(51) Int. Cl.
*A61B 5/08* (2006.01)
*A61B 5/00* (2006.01)
(Continued)

(52) U.S. Cl.
CPC .......... *A61B 5/6801* (2013.01); *A61B 5/0205* (2013.01); *A61B 5/1116* (2013.01);
(Continued)

(58) Field of Classification Search
None
See application file for complete search history.

(56) References Cited

U.S. PATENT DOCUMENTS

| 4,086,916 A | 5/1978 | Freeman et al. |
| 4,263,918 A | 4/1981 | Swearingen et al. |

(Continued)

FOREIGN PATENT DOCUMENTS

| EP | 0443267 A1 | 8/1991 |
| EP | 1938862 A2 | 7/2008 |

(Continued)

OTHER PUBLICATIONS

Soh et al., An investigation of respiration while wearing back belts. Applied Ergonomics 1997; 28(3):189-192.

(Continued)

*Primary Examiner* — Meredith Weare
(74) *Attorney, Agent, or Firm* — Michael A. Whittaker

(57) ABSTRACT

The invention provides a multi-sensor system that uses an algorithm based on adaptive filtering to monitor a patient's respiratory rate. The system features a first sensor selected from the following group: i) an impedance pneumography sensor featuring at least two electrodes and a processing circuit configured to measure an impedance pneumography signal; ii) an ECG sensor featuring at least two electrodes and an ECG processing circuit configured to measure an ECG signal; and iii) a PPG sensor featuring a light source, photodetector, and PPG processing circuit configured to measure a PPG signal. Each of these sensors measures a time-dependent signal which is sensitive to respiratory rate and, during operation, is processed to determine an initial respiratory rate value. An adaptive digital filter is determined from the initial respiratory rate. The system features a second sensor (e.g. a digital 3-axis accelerometer) that attaches to the patient's torso and measures an ACC signal indicating movement of the chest or abdomen that is also sensitive to respiratory rate. This second signal is processed (Continued)

with the adaptive filter to determine a final value for respiratory rate.

1 Claim, 33 Drawing Sheets

Related U.S. Application Data continuation of application No. 12/559,426, filed on Sep. 14, 2009, now Pat. No. 10,595,746.

(51) Int. Cl.
| | |
|---|---|
| *A61B 5/0205* | (2006.01) |
| *A61B 5/11* | (2006.01) |
| *A61B 5/318* | (2021.01) |
| A61B 5/024 | (2006.01) |
| A61B 5/0535 | (2021.01) |
| A61B 5/113 | (2006.01) |
| A61B 5/346 | (2021.01) |

(52) U.S. Cl.
CPC ............ *A61B 5/1118* (2013.01); *A61B 5/318* (2021.01); *A61B 5/681* (2013.01); *A61B 5/721* (2013.01); *A61B 5/0002* (2013.01); *A61B 5/02416* (2013.01); *A61B 5/0535* (2013.01); *A61B 5/0809* (2013.01); *A61B 5/0816* (2013.01); *A61B 5/113* (2013.01); *A61B 5/346* (2021.01); *A61B 5/6823* (2013.01); *A61B 5/6824* (2013.01); *A61B 5/6826* (2013.01); *A61B 5/7239* (2013.01); *A61B 5/746* (2013.01); *A61B 2562/0219* (2013.01)

(56) References Cited

U.S. PATENT DOCUMENTS

| | | | |
|---|---|---|---|
| 4,270,547 A | 6/1981 | Steffen et al. | |
| 4,305,400 A | 12/1981 | Logan | |
| 4,577,639 A | 3/1986 | Simon et al. | |
| 4,582,068 A | 4/1986 | Phillipps et al. | |
| 4,653,498 A | 3/1987 | New, Jr. et al. | |
| 4,710,164 A | 12/1987 | Levin et al. | |
| 4,722,351 A | 2/1988 | Phillipps et al. | |
| 4,802,486 A | 2/1989 | Goodman et al. | |
| 4,807,638 A | 2/1989 | Sramek | |
| 4,905,697 A | 3/1990 | Heggs et al. | |
| 5,025,791 A | 6/1991 | Niwa | |
| 5,140,990 A | 8/1992 | Jones et al. | |
| 5,190,038 A | 3/1993 | Polson et al. | |
| 5,197,489 A | 3/1993 | Conlan | |
| 5,224,928 A | 7/1993 | Sibalis et al. | |
| 5,247,931 A | 9/1993 | Norwood | |
| 5,289,824 A | 3/1994 | Mills et al. | |
| 5,316,008 A | 5/1994 | Suga et al. | |
| 5,339,818 A | 8/1994 | Baker et al. | |
| 5,448,991 A | 9/1995 | Polson et al. | |
| 5,465,082 A | 11/1995 | Chaco | |
| 5,482,036 A | 1/1996 | Diab et al. | |
| 5,485,838 A | 1/1996 | Ukawa et al. | |
| 5,490,505 A | 2/1996 | Diab et al. | |
| 5,515,858 A | 5/1996 | Myllymaki | |
| 5,517,988 A | 5/1996 | Gerhard | |
| 5,524,637 A | 6/1996 | Erickson | |
| 5,549,650 A | 8/1996 | Bornzin et al. | |
| 5,575,284 A | 11/1996 | Athan et al. | |
| 5,588,427 A | 12/1996 | Tien | |
| 5,593,431 A | 1/1997 | Sheldon | |
| 5,632,272 A | 5/1997 | Diab et al. | |
| 5,645,060 A | 7/1997 | Yorkey | |
| 5,649,543 A | 7/1997 | Hosaka et al. | |
| 5,680,870 A | 10/1997 | Hood, Jr. et al. | |
| 5,685,299 A | 11/1997 | Diab et al. | |
| 5,709,205 A | 1/1998 | Bukta | |
| 5,743,856 A | 4/1998 | Oka et al. | |
| 5,766,131 A | 6/1998 | Kondo et al. | |
| 5,769,785 A | 6/1998 | Diab et al. | |
| 5,800,349 A | 9/1998 | Isaacson et al. | |
| 5,820,550 A | 10/1998 | Polson et al. | |
| 5,848,373 A | 12/1998 | Delorme et al. | |
| 5,853,370 A | 12/1998 | Chance et al. | |
| 5,857,975 A | 1/1999 | Golub | |
| 5,865,755 A | 2/1999 | Golub | |
| 5,865,756 A | 2/1999 | Peel, III | |
| 5,873,834 A | 2/1999 | Yanagi et al. | |
| 5,876,353 A | 3/1999 | Riff | |
| 5,895,359 A | 4/1999 | Peel, III | |
| 5,899,855 A | 5/1999 | Brown | |
| 5,913,827 A | 6/1999 | Gorman | |
| 5,919,141 A | 7/1999 | Money et al. | |
| 5,941,836 A | 8/1999 | Friedman | |
| 5,964,701 A | 10/1999 | Asada et al. | |
| 5,964,720 A | 10/1999 | Pelz | |
| 5,971,930 A | 10/1999 | Elghazzawi | |
| 6,002,952 A | 12/1999 | Diab et al. | |
| 6,011,985 A | 1/2000 | Athan et al. | |
| 6,018,673 A | 1/2000 | Chin et al. | |
| 6,036,642 A | 3/2000 | Diab et al. | |
| 6,041,783 A | 3/2000 | Gruenke | |
| 6,057,758 A | 5/2000 | Dempsey et al. | |
| 6,067,462 A | 5/2000 | Diab et al. | |
| 6,081,735 A | 6/2000 | Diab et al. | |
| 6,081,742 A | 6/2000 | Amano et al. | |
| 6,094,592 A | 7/2000 | Yorkey et al. | |
| 6,117,077 A | 9/2000 | Del Mar et al. | |
| 6,129,686 A | 10/2000 | Friedman | |
| 6,157,850 A | 12/2000 | Diab et al. | |
| 6,159,147 A | 12/2000 | Lichter et al. | |
| 6,160,478 A | 12/2000 | Jacobsen et al. | |
| 6,168,569 B1 | 1/2001 | McEwen et al. | |
| 6,198,394 B1 | 3/2001 | Jacobsen et al. | |
| 6,198,951 B1 | 3/2001 | Kosuda et al. | |
| 6,199,550 B1 | 3/2001 | Wiesmann et al. | |
| 6,206,830 B1 | 3/2001 | Diab et al. | |
| 6,236,872 B1 | 5/2001 | Diab et al. | |
| 6,251,080 B1 | 6/2001 | Henkin et al. | |
| 6,261,247 B1 | 7/2001 | Ishikawa et al. | |
| 6,262,769 B1 | 7/2001 | Anderson et al. | |
| 6,263,222 B1 | 7/2001 | Diab et al. | |
| 6,287,262 B1 | 9/2001 | Amano et al. | |
| 6,334,065 B1 | 12/2001 | Al-Ali et al. | |
| 6,371,921 B1 | 4/2002 | Caro et al. | |
| 6,388,240 B2 | 5/2002 | Schulz et al. | |
| RE37,852 E * | 9/2002 | Aso et al. ......... | A61B 5/02255 600/494 |
| 6,443,890 B1 | 9/2002 | Schulze et al. | |
| 6,480,729 B2 | 11/2002 | Stone | |
| 6,491,647 B1 | 12/2002 | Bridger et al. | |
| 6,503,206 B1 | 1/2003 | Li et al. | |
| 6,514,218 B2 | 2/2003 | Yamamoto | |
| 6,516,218 B1 | 2/2003 | Cheng et al. | |
| 6,516,289 B2 | 2/2003 | David | |
| 6,526,310 B1 | 2/2003 | Carter et al. | |
| 6,527,729 B1 | 3/2003 | Turcott | |
| 6,533,729 B1 | 3/2003 | Khair et al. | |
| 6,541,756 B2 | 4/2003 | Schulz et al. | |
| 6,544,173 B2 | 4/2003 | West et al. | |
| 6,544,174 B2 | 4/2003 | West et al. | |
| 6,546,267 B1 | 4/2003 | Sugiura et al. | |
| 6,551,252 B2 | 4/2003 | Sackner et al. | |
| 6,584,336 B1 | 6/2003 | Ali et al. | |
| 6,589,170 B1 | 7/2003 | Flach et al. | |
| 6,595,929 B2 | 7/2003 | Stivoric et al. | |
| 6,605,038 B1 | 8/2003 | Teller et al. | |
| 6,616,606 B1 | 9/2003 | Petersen et al. | |
| 6,650,917 B2 | 11/2003 | Diab et al. | |
| 6,684,090 B2 | 1/2004 | Ali et al. | |
| 6,732,064 B1 | 5/2004 | Kadtke et al. | |
| 6,745,060 B2 | 6/2004 | Diab et al. | |
| 6,770,028 B1 | 8/2004 | Ali et al. | |
| 6,790,178 B1 | 9/2004 | Mault et al. | |
| 6,811,538 B2 | 11/2004 | Westbrook et al. | |
| 6,845,256 B2 | 1/2005 | Chin et al. | |

(56) References Cited

U.S. PATENT DOCUMENTS

| | | |
|---|---|---|
| 6,850,787 B2 | 2/2005 | Weber et al. |
| 6,879,850 B2 | 4/2005 | Kimball |
| 6,893,396 B2 | 5/2005 | Schulze et al. |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 | 1/2006 | Suzuki et al. |
| 6,997,882 B1 | 2/2006 | Parker et al. |
| 7,004,907 B2 | 2/2006 | Banet et al. |
| 7,020,508 B2 | 3/2006 | Stivoric et al. |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,079,888 B2 | 7/2006 | Oung et al. |
| 7,115,824 B2 | 10/2006 | Lo |
| 7,156,809 B2 | 1/2007 | Quy |
| 7,179,228 B2 | 2/2007 | Banet |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,451 B2 | 1/2008 | Halperin et al. |
| 7,351,206 B2 | 4/2008 | Suzuki et al. |
| 7,355,512 B1 | 4/2008 | Al-Ali |
| 7,373,191 B2 | 5/2008 | DeLonzor et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,420,472 B2 | 9/2008 | Tran |
| 7,427,926 B2 | 9/2008 | Sinclair et al. |
| 7,455,643 B1 | 11/2008 | Li et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | Devaul et al. |
| 7,976,480 B2 | 7/2011 | Grajales et al. |
| 7,983,933 B2 | 7/2011 | Karkanias et al. |
| 7,993,275 B2 | 8/2011 | Banet et al. |
| 8,047,998 B2 | 11/2011 | Kolluri et al. |
| 8,082,160 B2 | 12/2011 | Collins, Jr. et al. |
| 8,137,270 B2 | 3/2012 | Keenan et al. |
| 8,167,800 B2 | 5/2012 | Ouchi et al. |
| 8,180,440 B2 | 5/2012 | McCombie et al. |
| 8,419,649 B2 | 4/2013 | Banet et al. |
| 8,449,469 B2 | 5/2013 | Banet et al. |
| 8,506,480 B2 | 8/2013 | Banet et al. |
| 8,979,765 B2 * | 3/2015 | Banet ............... A61B 5/318 |
| | | 600/529 |
| 9,149,192 B2 | 10/2015 | Banet et al. |
| 10,555,676 B2 | 2/2020 | McCombie et al. |
| 10,595,746 B2 | 3/2020 | Banet et al. |
| 10,973,414 B2 | 4/2021 | Moon et al. |
| 2001/0004234 A1 | 6/2001 | Petelenz et al. |
| 2001/0007923 A1 | 7/2001 | Yamamoto |
| 2001/0013826 A1 | 8/2001 | Ahmed et al. |
| 2001/0045395 A1 | 11/2001 | Kitaevich et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0170193 A1* | 11/2002 | Townsend ............ A61B 5/1116 |
| | | 33/512 |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0097046 A1 | 5/2003 | Sakamaki et al. |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Connor et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0111033 A1 | 6/2004 | Oung et al. |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0193063 A1 | 9/2004 | Kimura et al. |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode et al. |
| 2005/0059870 A1 | 3/2005 | Aceti |
| 2005/0070773 A1 | 3/2005 | Chin et al. |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0216199 A1 | 9/2005 | Banet |
| 2005/0228296 A1 | 10/2005 | Banet |
| 2005/0228297 A1 | 10/2005 | Banet et al. |
| 2005/0228298 A1 | 10/2005 | Banet et al. |

(56) References Cited

U.S. PATENT DOCUMENTS

| | | |
|---|---|---|
| 2005/0228299 A1 | 10/2005 | Banet |
| 2005/0228300 A1 | 10/2005 | Jaime et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0261598 A1 | 11/2005 | Banet et al. |
| 2005/0265267 A1 | 12/2005 | Hwang |
| 2005/0283088 A1 | 12/2005 | Bernstein |
| 2006/0009697 A1 | 1/2006 | Banet et al. |
| 2006/0009698 A1 | 1/2006 | Banet et al. |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0084878 A1 | 4/2006 | Banet et al. |
| 2006/0122469 A1 | 6/2006 | Martel |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0142730 A1 | 6/2007 | Laermer et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0276632 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0039731 A1 | 2/2008 | McCombie et al. |
| 2008/0077026 A1 | 3/2008 | Banet et al. |
| 2008/0077027 A1 | 3/2008 | Allgeyer |
| 2008/0082001 A1 | 4/2008 | Hatlestad et al. |
| 2008/0082004 A1 | 4/2008 | Banet et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1* | 6/2008 | Hansmann ............ A61B 5/0823 600/529 |
| 2008/0146887 A1 | 6/2008 | Rao et al. |
| 2008/0146892 A1 | 6/2008 | LeBoeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1* | 3/2009 | Gao ...................... H04L 67/125 600/300 |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2010/0010380 A1 | 1/2010 | Panken et al. |
| 2010/0030034 A1 | 2/2010 | Schulhauser et al. |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0195512 A1 | 8/2010 | Harvey |
| 2010/0210930 A1 | 8/2010 | Saylor |
| 2010/0217099 A1 | 8/2010 | LeBoeuf et al. |
| 2010/0222649 A1 | 9/2010 | Schoenberg |
| 2010/0234693 A1 | 9/2010 | Srinivasan et al. |
| 2010/0234695 A1 | 9/2010 | Morris |
| 2010/0234786 A1 | 9/2010 | Fulkerson et al. |
| 2010/0241011 A1 | 9/2010 | McCombie et al. |

(56) References Cited

U.S. PATENT DOCUMENTS

| | | |
|---|---|---|
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |

FOREIGN PATENT DOCUMENTS

| | | |
|---|---|---|
| GB | 2329250 A1 | 3/1999 |
| WO | 9932030 A1 | 7/1999 |
| WO | 2006005169 A1 | 1/2006 |
| WO | 2007024777 A2 | 3/2007 |
| WO | 2007143535 A2 | 12/2007 |
| WO | 2008037820 A1 | 4/2008 |
| WO | 2008057883 A2 | 5/2008 |
| WO | 2008110788 A1 | 9/2008 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

Subbe et al., Effect of introducing the Modified Early Warning score on clinical outcomes, cardiopulmonary arrests and intensive care utilization in acute medical admissions. Anaesthesia Aug. 2003;58(8):797-802.
Talkowski, Quantifying Physical Activity in Community Dwelling Older Adults Using Accelerometry. University of Pittsburgh (Dissertation) 2008: 1-91.
Thongpithoonrat et al., Networking and Plug-and-Play of Bedside Medical Instruments. Conf Proc IEEE Eng Med Biol Soc. 2008;2008:1514-1517.
USB 2.0 Specification Engineering Change Notice. Oct. 20, 2000.
Vuorela et al., Two portable long-term measurement devices for ECG and bioimpedance. Second International Conference on Pervasive Computing Technologies for Healthcare. Jan. 30-Feb. 1, 2008:169-172.
Wolf et al., Development of a Fall Detector and Classifier based on a Triaxial Accelerometer Demo Board. 2007:210-213.
Yan and Zhang, A Novel Calibration Method far Noninvasive Blood Pressure Measurement Using Pulse Transit Time. Proceedings of the 4th IEEE-EMBS International Summer School and Symposium on Medical Devices and D Biosensors St Catharine's College, Cambridge, UK, Aug. 19-22, 2007.
Yang et al., Research on Multi-Parameter Physiological Monitor Based on CAN Bus. IFMBE Proceed. 2008; 19:417-419.
Zeltwanger, Controller Area Network and CANopen in Medical Equipment. Bus Briefing: Med Dev Manuf Technol. 2002:34-37.
Zislin et al., Ways of Improving the Accuracy of Arterial Pressure Oscillometry. Biomedical Engineering 2005;39 (4):174-178.
Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.
Extended European Search Report and Written Opinion issued in EP 15159340.7 dated Dec. 10, 2015.
International Preliminary Report on Patentability dated Jan. 5, 2012 issued in PCT/US2010/039000.
International Preliminary Report on Patentability dated Dec. 1, 2011 issued in PCT/US2010/035554.
International Search Report and Written Opinion dated Mar. 3, 2011 issued in PCT/US2010/062564.
International Search Report and Written Opinion dated Apr. 27, 2012 as reported in PCT/US2011/067441.
International Search Report and Written Opinion dated May 29, 2012 issued in PCT/US2012/025648.
International Search Report and Written Opinion dated Jun. 29, 2012 issued in PCT/US2012/025640.
International Search Report and Written Opinion dated Jul. 22, 2011 issued in PCT/US2011/027843.
International Search Report and Written Opinion dated Jul. 20, 2011 issued in PCT/US2011/033100.
International Search Report and Written Opinion dated Sep. 23, 2010 issued in PCT/US2010/035554.
International Search Report and Written Opinion dated Sep. 7, 2010 issued in PCT/US2010/039000.
International Search Report and Written Opinion dated Oct. 15, 2010 issued in PCT/US2010/035550.
International Search Report and Written Opinion dated Nov. 3, 2010 issued in PCT/US2010/048729.
International Search Report and Written Opinion dated Nov. 5, 2010 issued in PCT/US2010/048866.
International Search Report and Written Opinion issued in PCT/US2012/064302 on Jan. 15, 2013.
Partial European Search Report issued in EP 15159340 dated Jul. 16, 2015.
Supplemental European Search Report issued in EP 10778376 dated Jan. 31, 2013.

(56) References Cited

OTHER PUBLICATIONS

Ahlstrom et al., Noninvasive investigation of blood pressure changes using the pulse wave transit time: a novel approach in the monitoring of hemodialysis patients. J Artif Organs. 2005;8(3):192-197.
Allen et al., Classification of a known sequence of motions and postures from accelerometry data using adapted Gaussian mixture models. Physiol. Meas. 2006;27:935-951.
Alves et al., CAN Protocol: A Laboratory Prototype for Fieldbus Applications. XIX IMEKO World Congress Fundamental and Applied Metrology Sep. 6-11, 2009, Lisbon, Portugal. 4 pages :454-457 ISBN 978-963-88410-0-1.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Benefits of Digital Sensors. Gems Sensors. Feb. 14, 2008. http://www.sensorland.com/HowPage054.html.
Bonfiglio et al., Managing Catastrophic Events by Wearable Mobile Systems. Mobile Response {Lecture Notes in Computer Science) Feb. 2007;4458:95-105.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2001;33(3):349-356.
Chan et al., Noninvasive and Cuffless Measurements of Blood Pressure For Telemedicine. Proceedings of the 23rd Annual International Conference of the IEEE Engineering in Medicine and Biology Society 2001:3 pages.
Clifford et al., Measuring Tilt with Low-g Accelerometers. Freescale Semiconductor, Inc., 2005:8 pages.
Controller-Area Network (can BUS). Apr. 2, 2009. accessed online at: https://en.wikipedia.org/wiki/CAN_bus.
Cretikos et al., The Objective Medical Emergency Team Activation Criteria: a case-control study. Resuscitation Apr. 2007;73(1 ):62-72.
De Scalzi et al., Relationship Between Systolic Time Intervals and Arterial Blood Pressure. Clin Cardiol. 1986;9:545-549.
Drinnan et al., Relation between heart rate and pulse transit time during paced respiration. Physiol Meas. Aug. 2001 ;22(3 ): 425-432.
Espina et al., Wireless Body Sensor Network for Continuous Cuff-less Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1, 1993; 8(7):354-360.
Flash et al., The Coordination of Arm Movements: An Experimentally Confirmed Mathematical Model. J Neurosci. Jul. 1985;5(7): 1688-1703.
Fung, Advisory System far Administration of Phenylephrine Following Spinal Anesthesia for Cesarean Section. Master's Thesis. University of British Columbia 2002: 119 pages.
Gallagher, Comparison of Radial and Femoral Arterial Blood Pressure in Children after Cardiopulmonary Bypass. J Clin Monit Jul. 1985;1(3):168-171.
Goldhill et al., A physiologically-based early warning score for ward patients: the association between score and putcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jackson, Digital Filter Design and Synthesis Using High-Level Modeling Tools. Virginia Polytechnic Institute and State University Thesis. Dec. 1999.
Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009.

Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol Meas. 2000;21:79-88.
Khan et al., Accelerometer Signal-based Human Activity Recognition Using Augmented Autoregressive Model Coefficients and Artificial w Neural Nets. 30th Annual International Conference of the IEEE Engineering in Medicine and Biology Society. Aug. 20-24, 2008:5172-5175.
Kim et al., Two Algorithms for Detecting Respiratory Rate from ECG Signal. IFMBE Proceedings 2007;14(6) JC27:4069-4071.
Klabunde, Mean Arterial Pressure. Cardiovascular Physiology Concepts. Mar. 8, 2007. http://www.cvphysiology.com/Blood%20Pressure/BP006.
Liu et al., The Changes in Pulse Transit Time at Specific Cuff Pressures during Inflation and Deflation. Proceedings of the 28th IEEE EMBS Annual International Conference New York City, USA, Aug. 30-Sep. 3, 2006:6404-6405.
Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1 :996-999.
Mason, Signal Processing Methods for Non-Invasive Respiration Monitoring. Department of Engineering Science, University of Oxford 2002 (175 pages).
Mathie et al., Classification of basic daily movements using a triaxial accelerometer. Med Biol Eng Comput. Sep. 2004;42(5):679-687.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.
McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard-A Personal Physiological Monitor Far Extreme Environments. Conf Proc IEEE Eng Med Biol Soc. 2004;3:2192-2195.
Nitzan et al., Effects of Externa! Pressure on Arteries Distal to the Cuff During Sphygmomanometry. IEEE Transactions on Biomedical Engineering, Jun. 2005;52{6): 1120-1127.
O'Haver, Peak Finding and Measurement, Version 1.6 Oct. 26, 2006. http://terpconnect.umd.edu/-toh/spectrum/PeakFindingandMeasurement.htm.
Otto et al., System Architecture of a Wireless Body Area Sensor Network for Ubiquitous Health Monitoring. Journal of Mobile Multimedia Jan. 10, 2006;1 (4):307-326.
Packet Definition. The Linux Information Project Jan. 8, 2006 http://www.linfo.org/packet.html.
Park et al., An improved algorithm for respiration signal extraction from electrocardiogram measured by conductive textile electrodes using instantaneous frequency estimation. Med Bio Eng Comput 2008;46:147-158.
Park and Guntheroth, Direct Blood Pressure Measurements in Brachial and Femoral Arteries in Children. Circulation Feb. 1970; 41 (2):231-237.
PDF-Pro for iPhone & iPod touch User Manual. ePapyrus Jul. 2009;1 :1-25 http://epapyrus.com/en/files/PDFPro%.
Poon and Zhang, Cuff-Less and Noninvasive Measurements of Arterial Blood Pressure by Pulse Transit Time. Conf Proc IEEE Eng Med Biol Soc. 2005;6:5877-5880.
Reddan et al., Intradialytic Blood vol. Monitoring in Ambulatory Hemodialysis Patients: A Randomized Trial. J Am Soc Nephrol. Jul. 2005;16(7):2162-2169.

(56) References Cited

OTHER PUBLICATIONS

Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
RS-232. Wikipedia Dec. 5, 2008 accessed online at: http://en.wikipedia.org/wiki/RS-232.
Scanaill et al., A Review of Approaches to Mobility Telemonitoring of the Elderly in Their Living Environment. Annals of Biomed Engineer. Apr. 2006;34(4):547-563.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Signal Strength. Oct. 6, 2008. accessed online at: https://en.wikipedia.org/wiki/Signal_strength.

\* cited by examiner

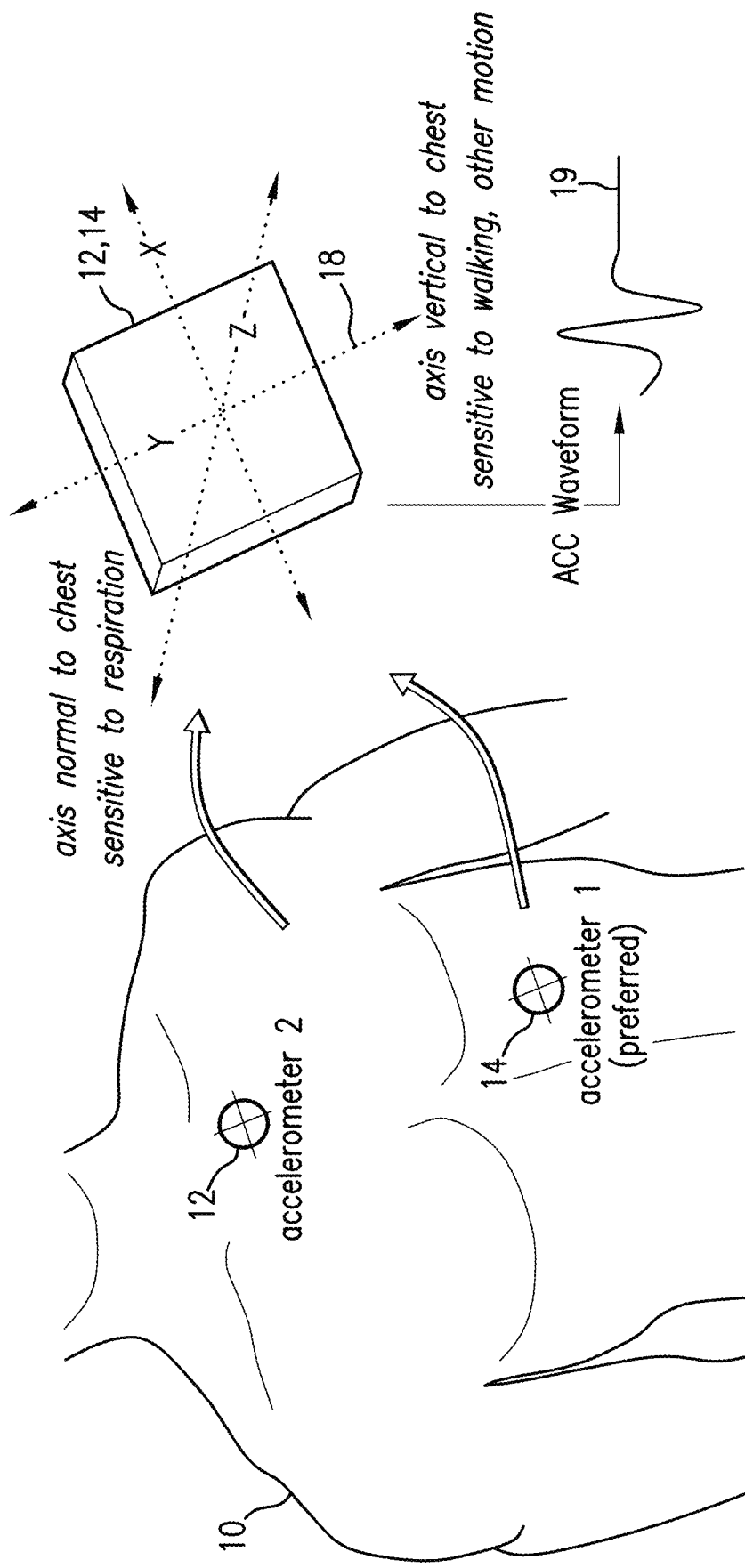

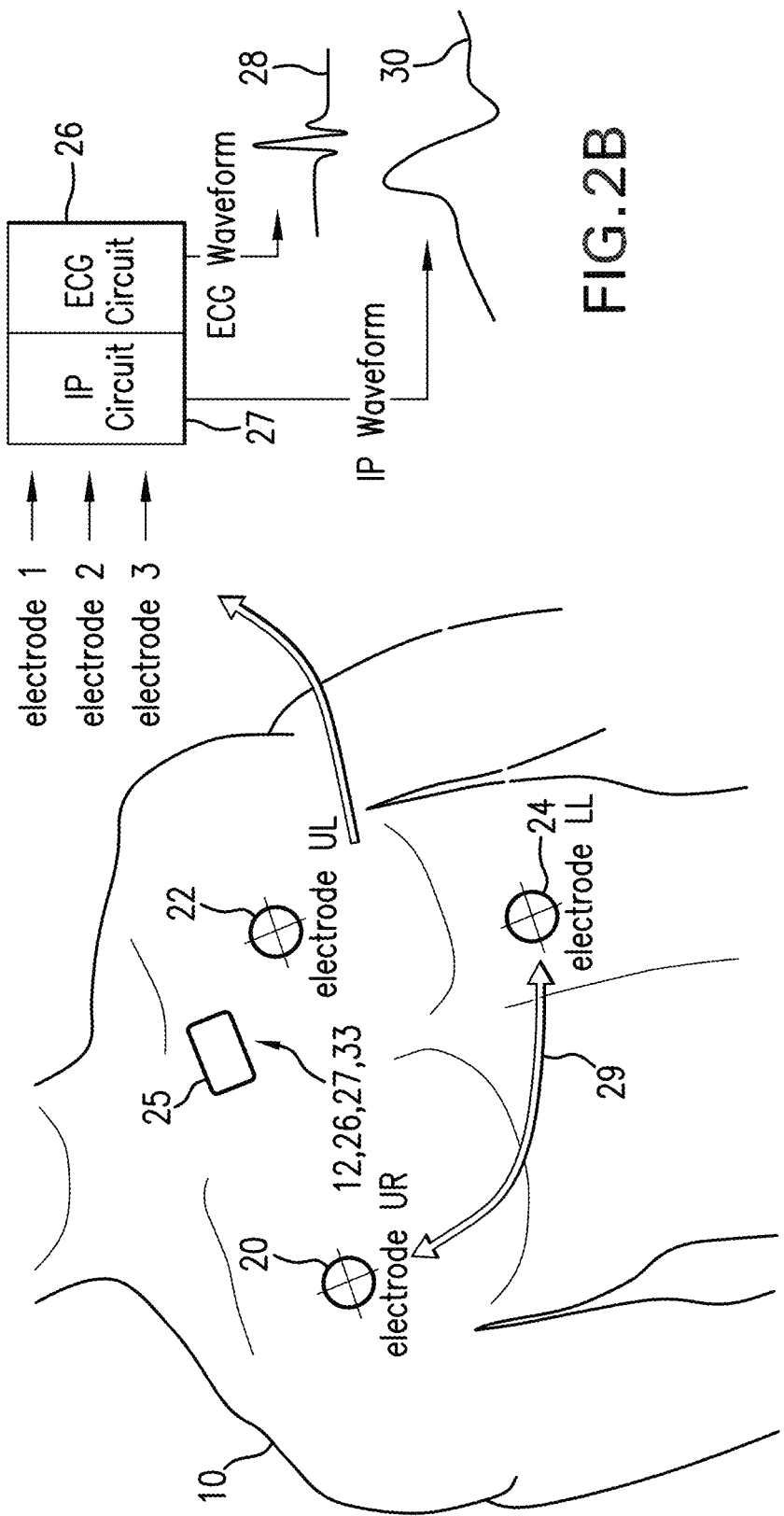

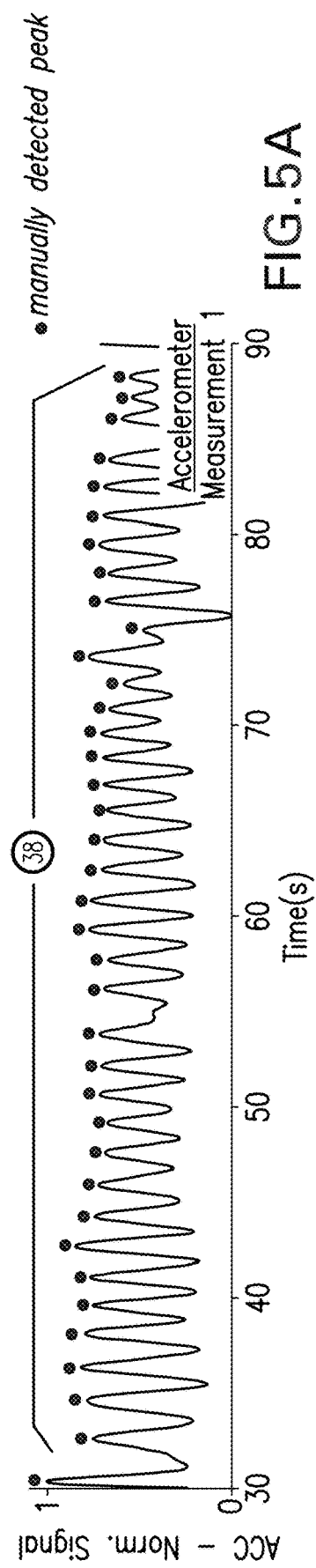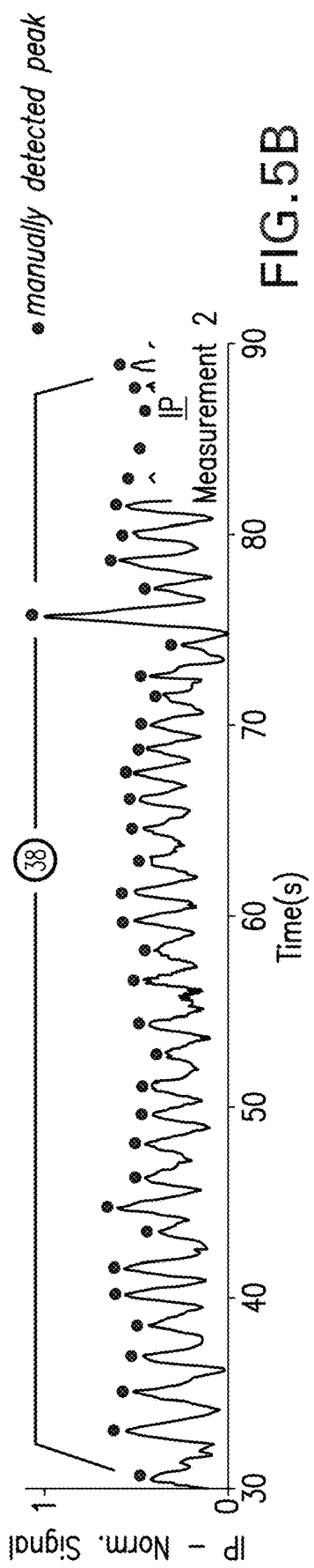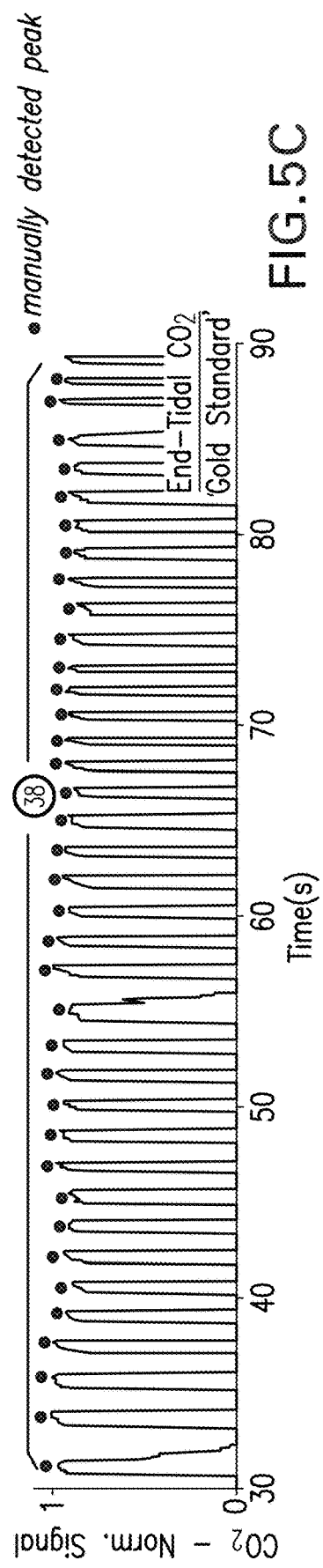

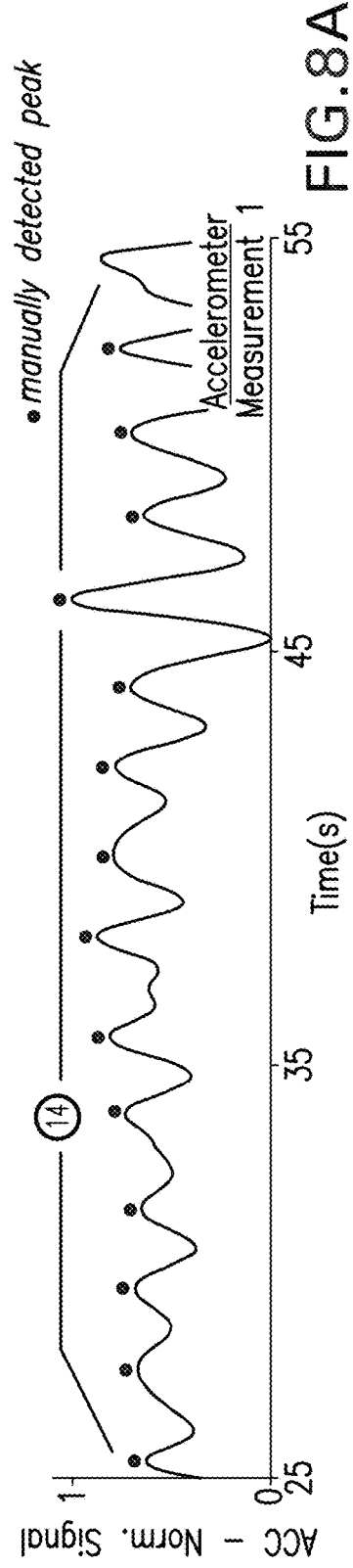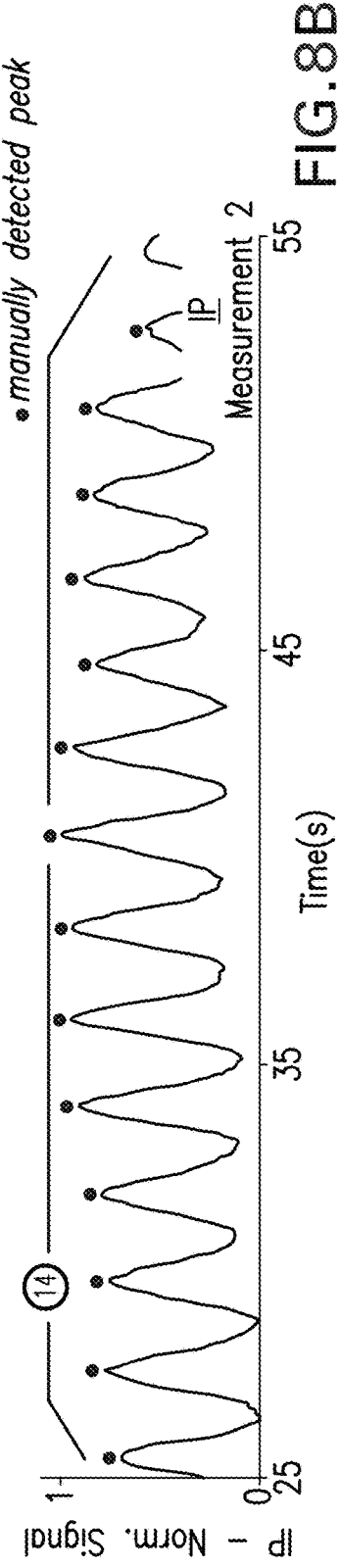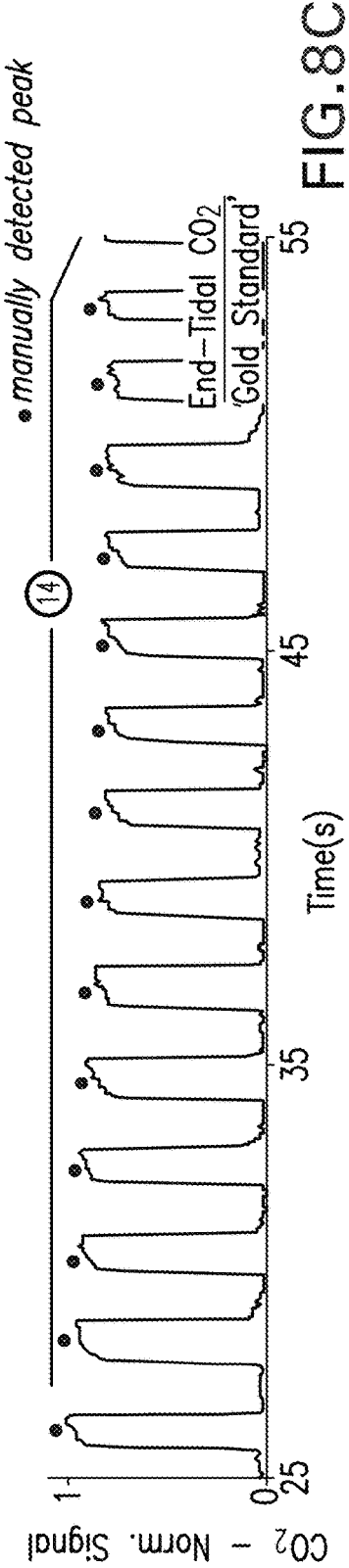

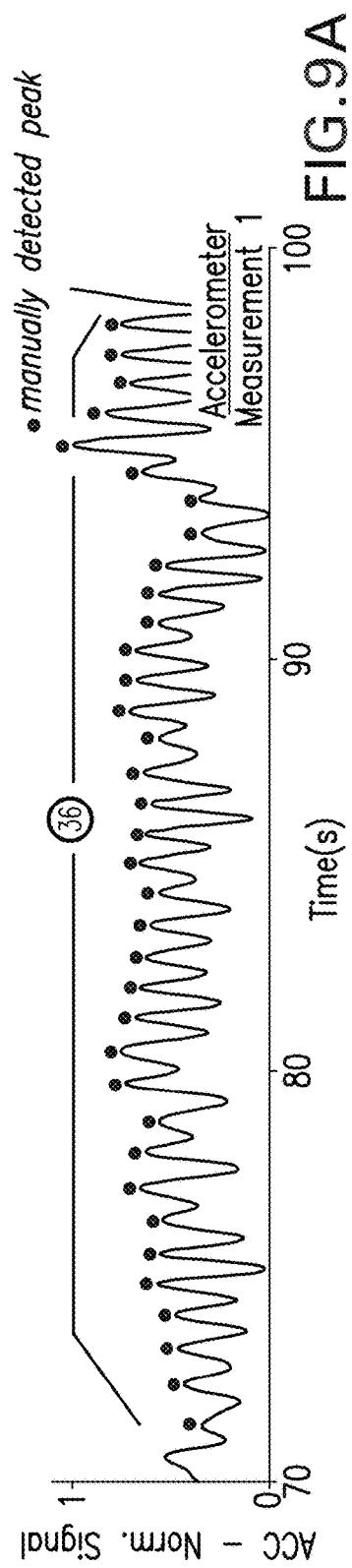
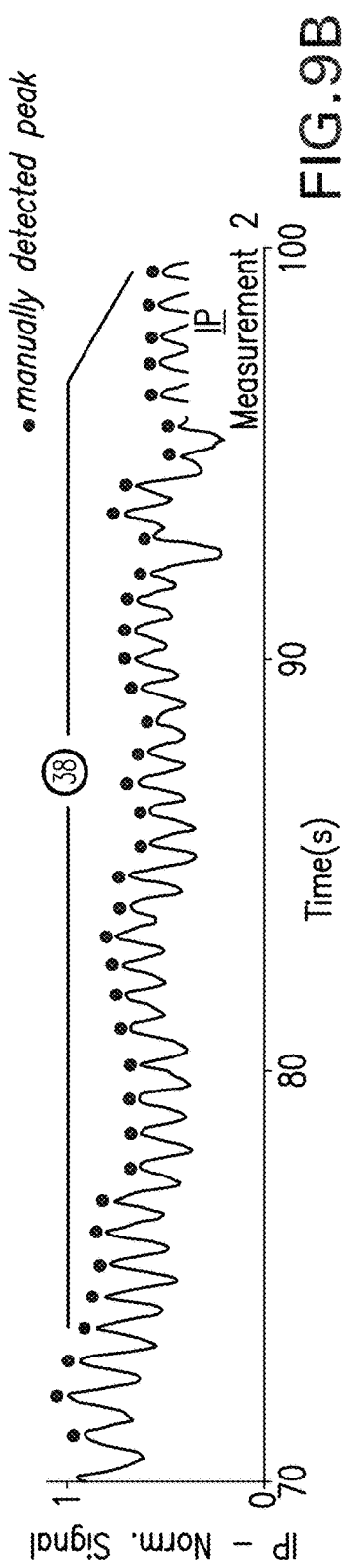
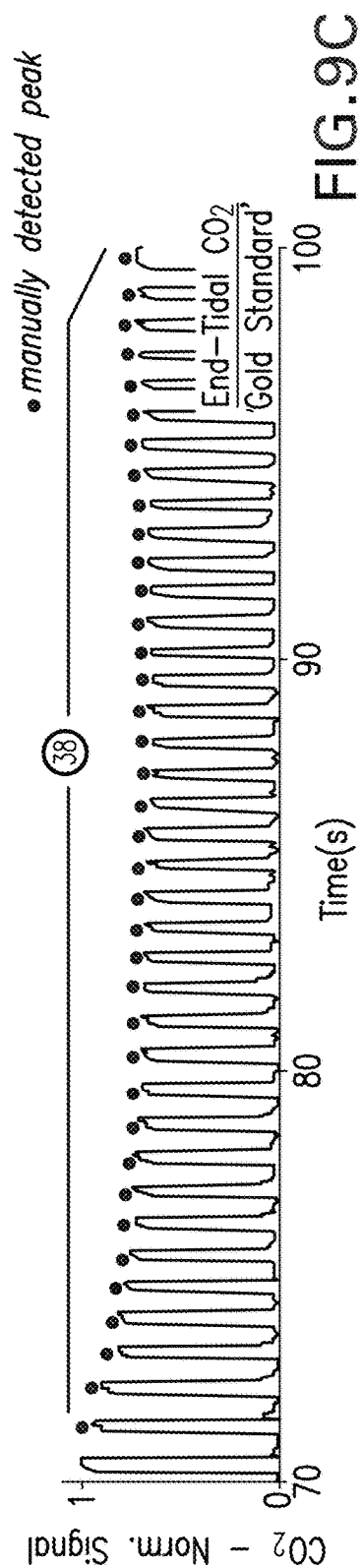

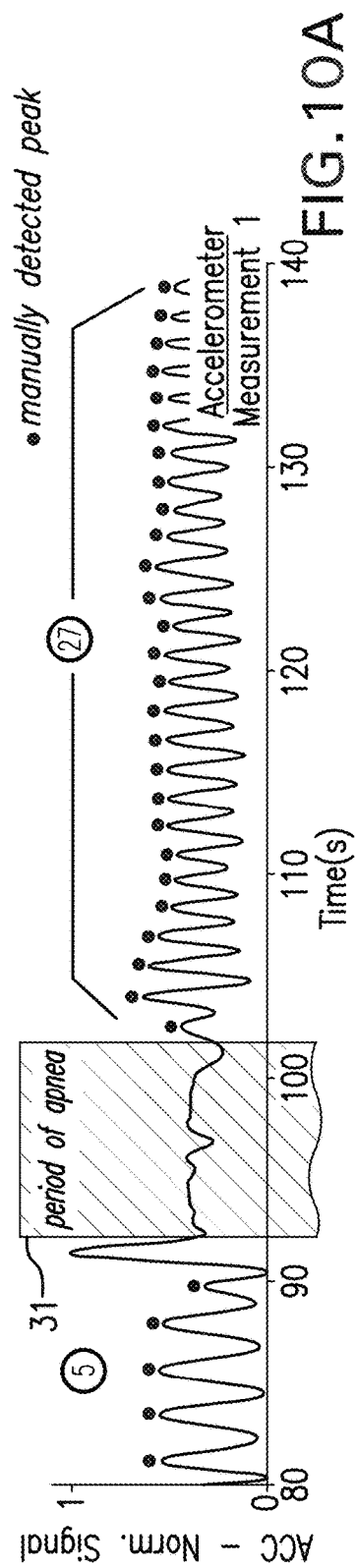
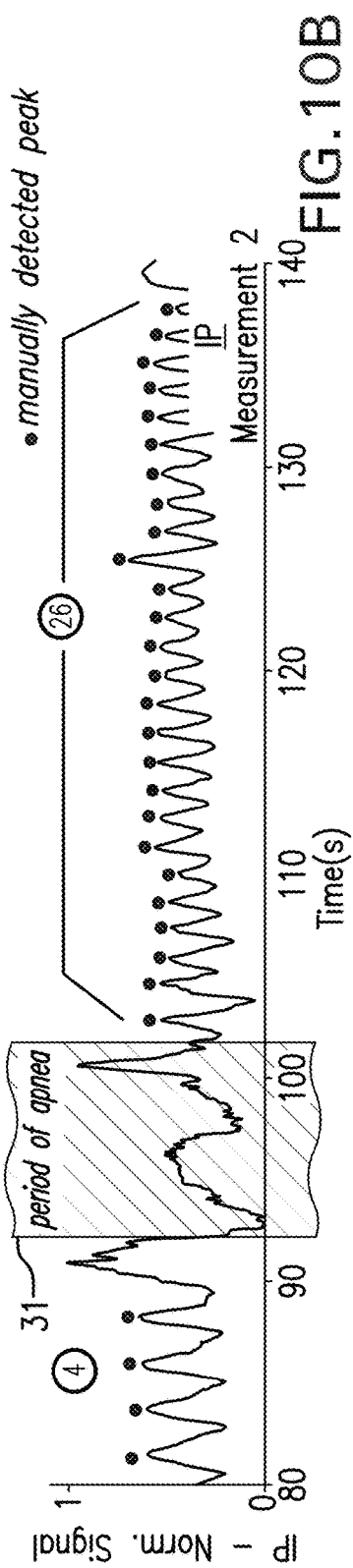
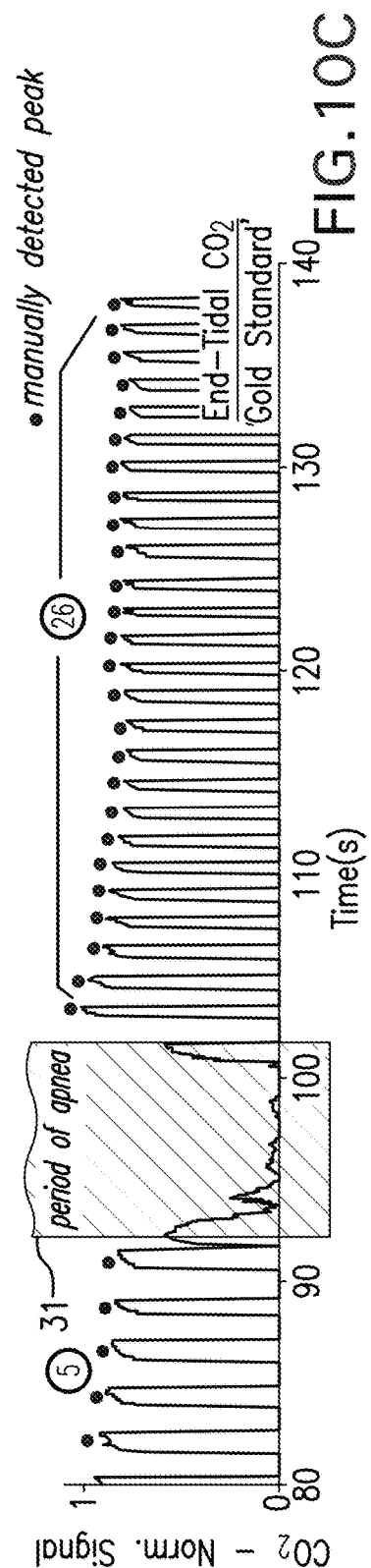

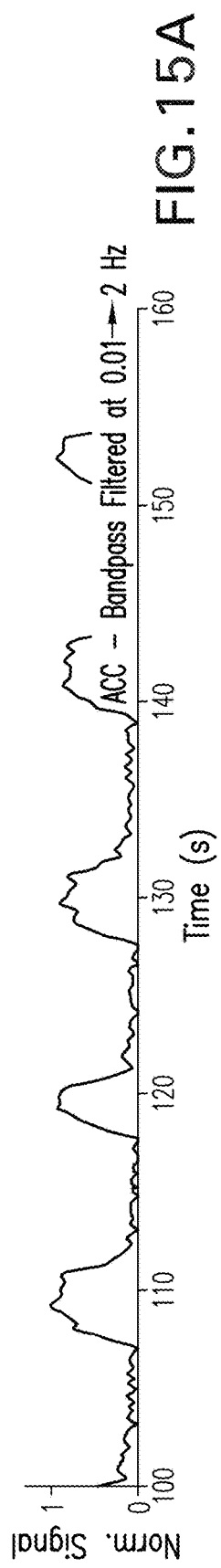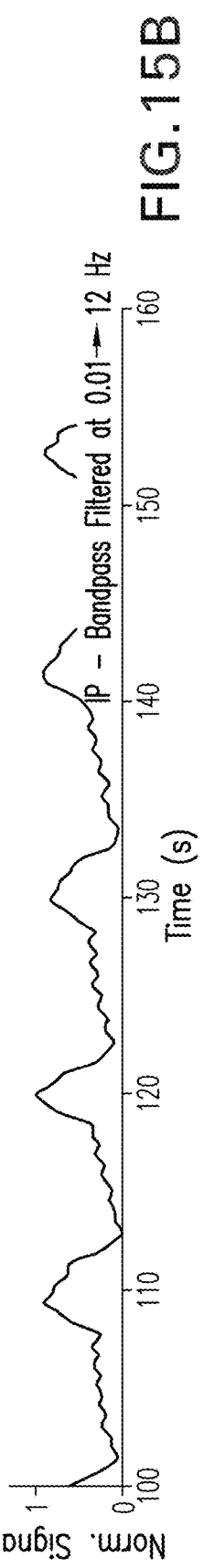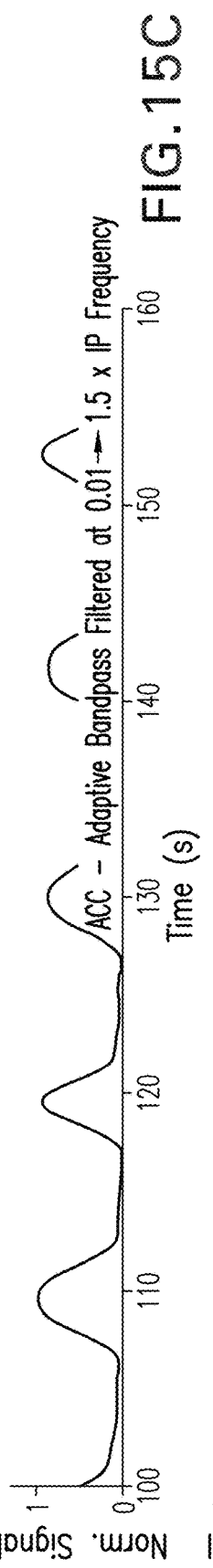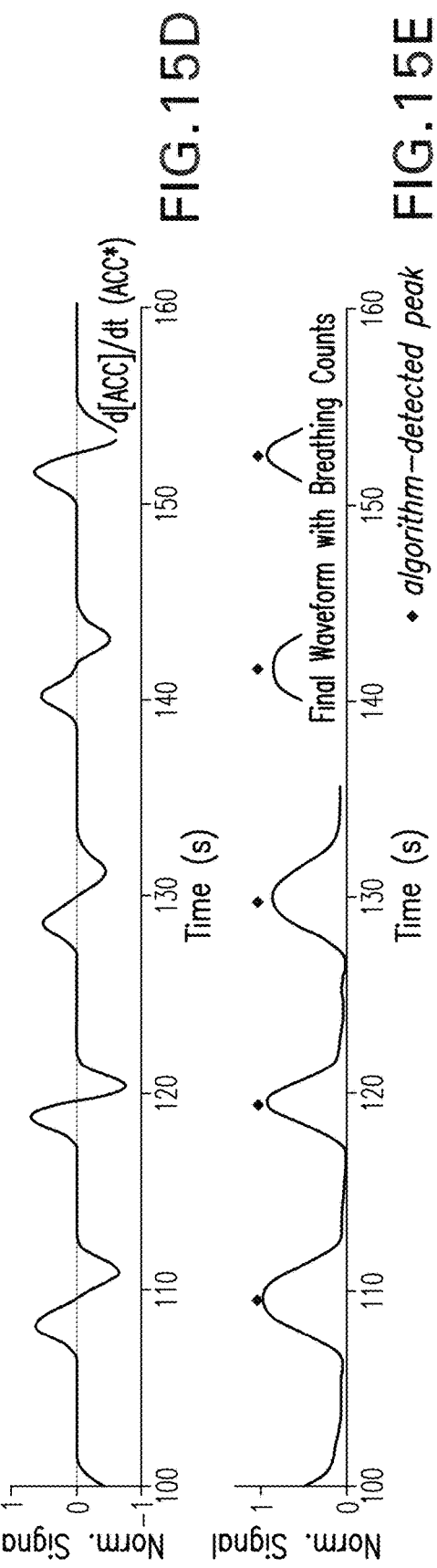

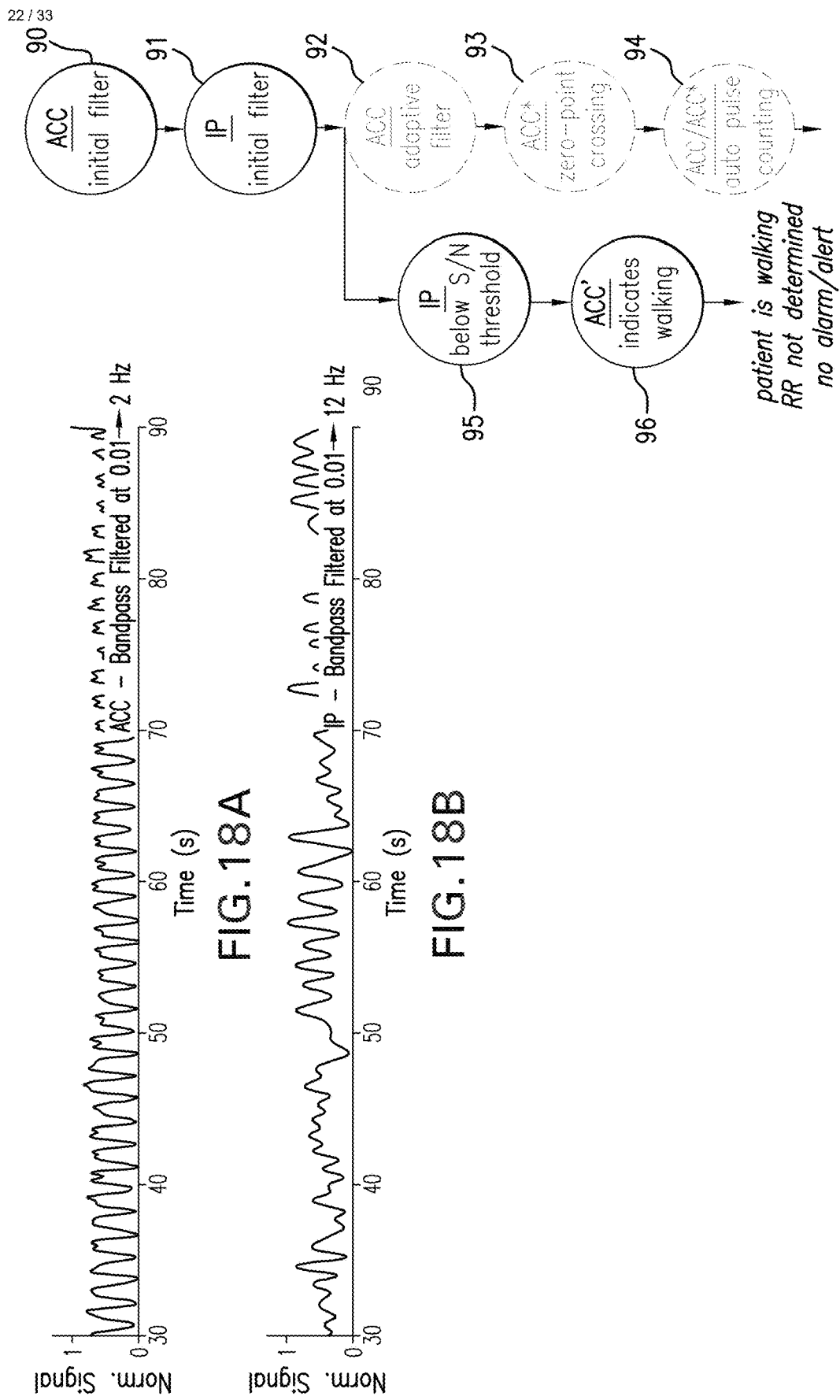

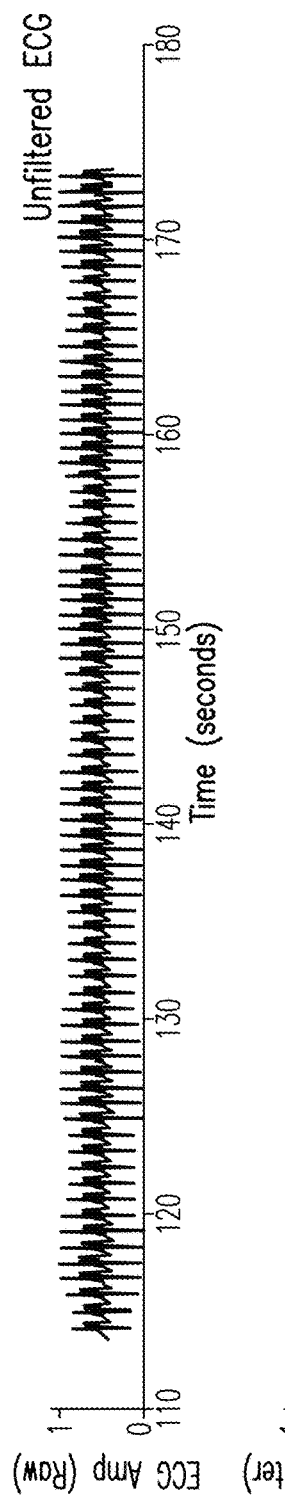
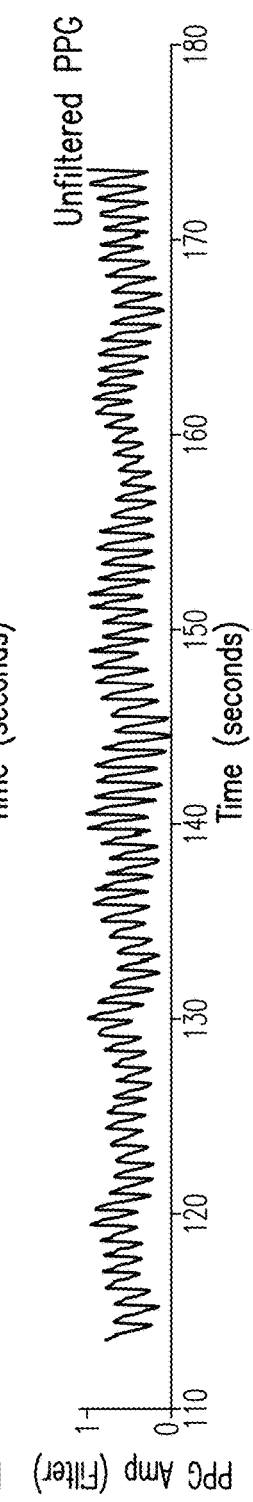
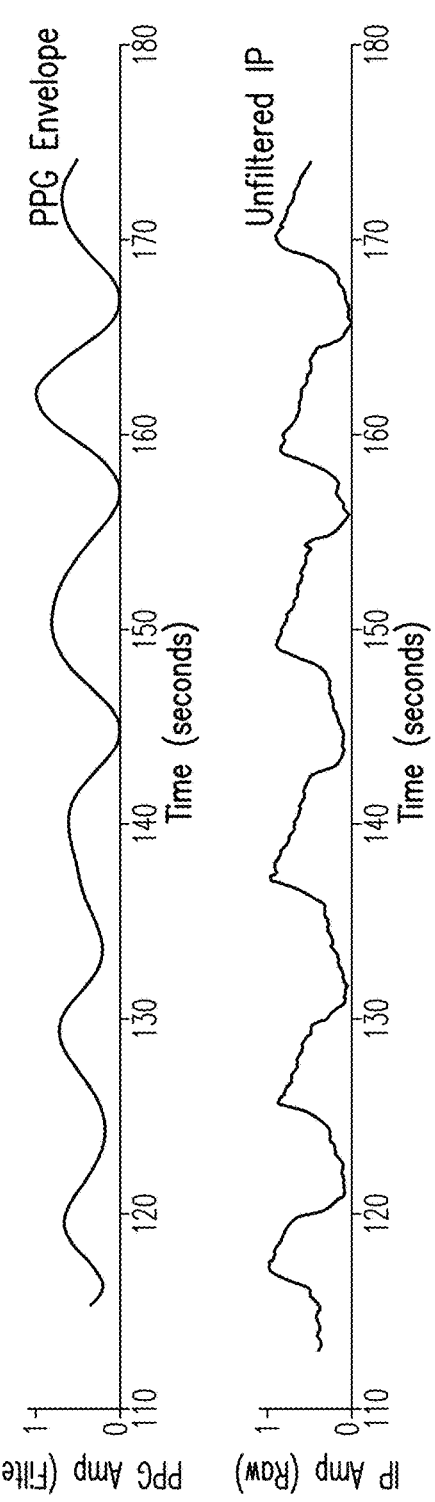
FIG. 20A
FIG. 20B
FIG. 20C
FIG. 20D
FIG. 20E

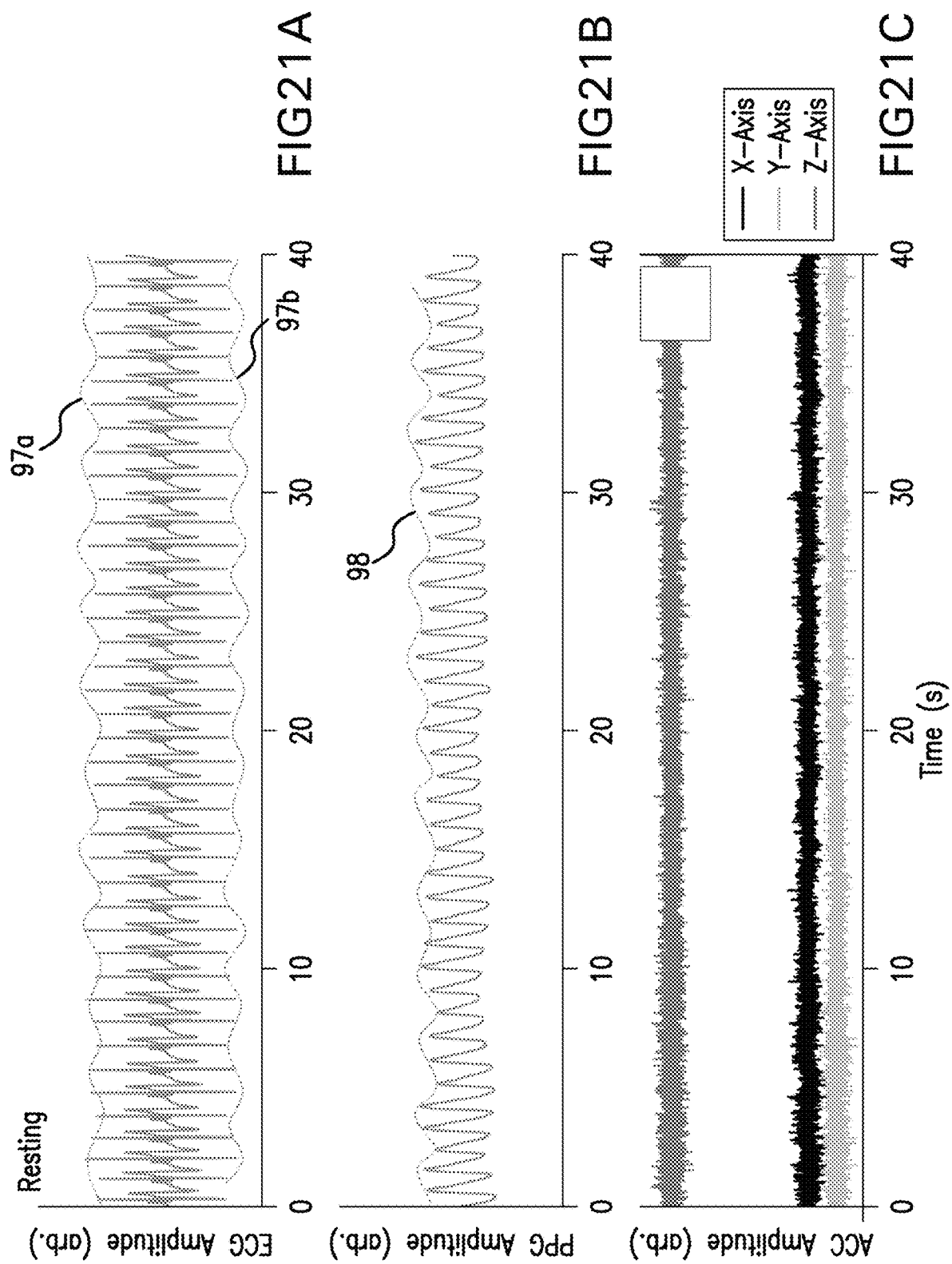

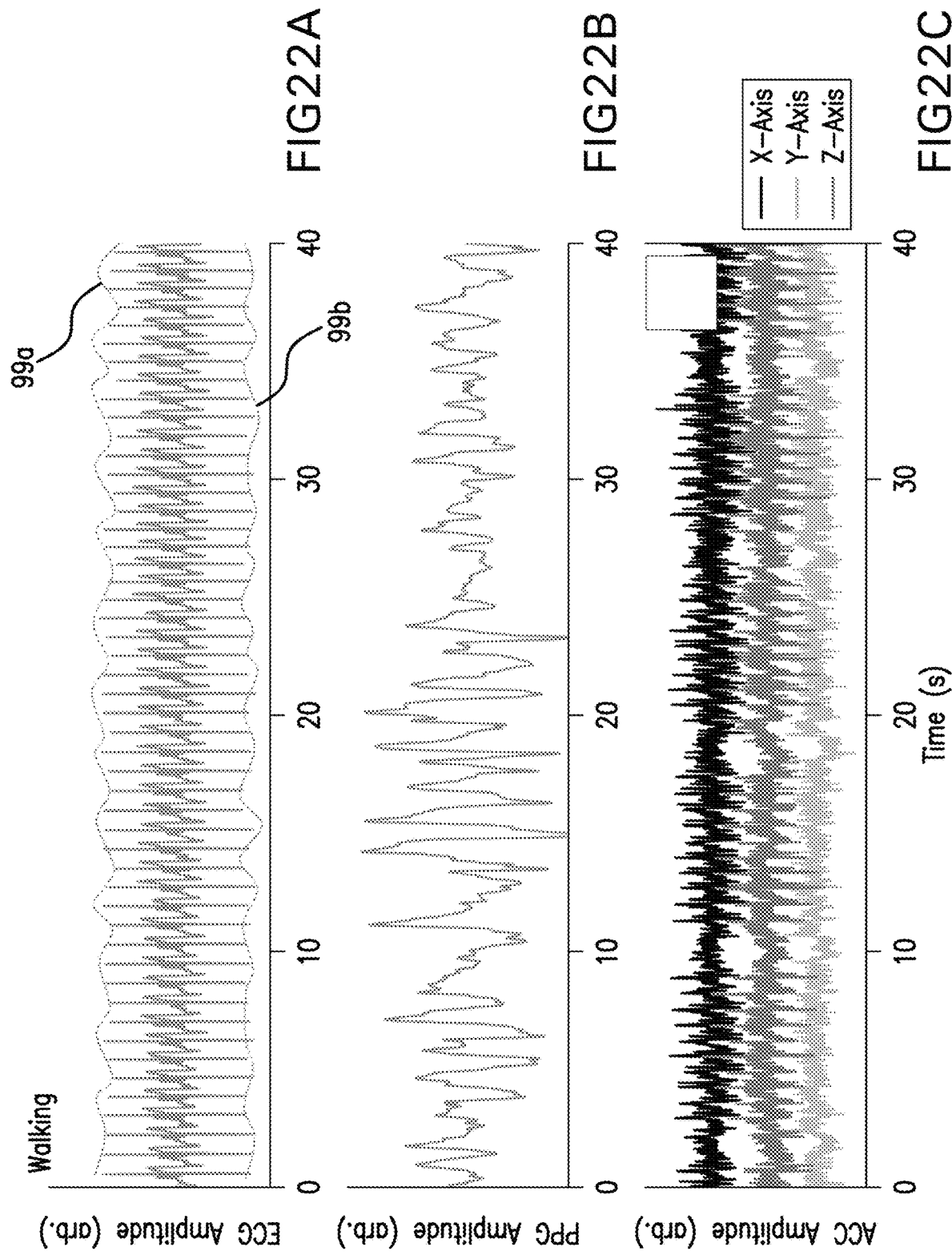

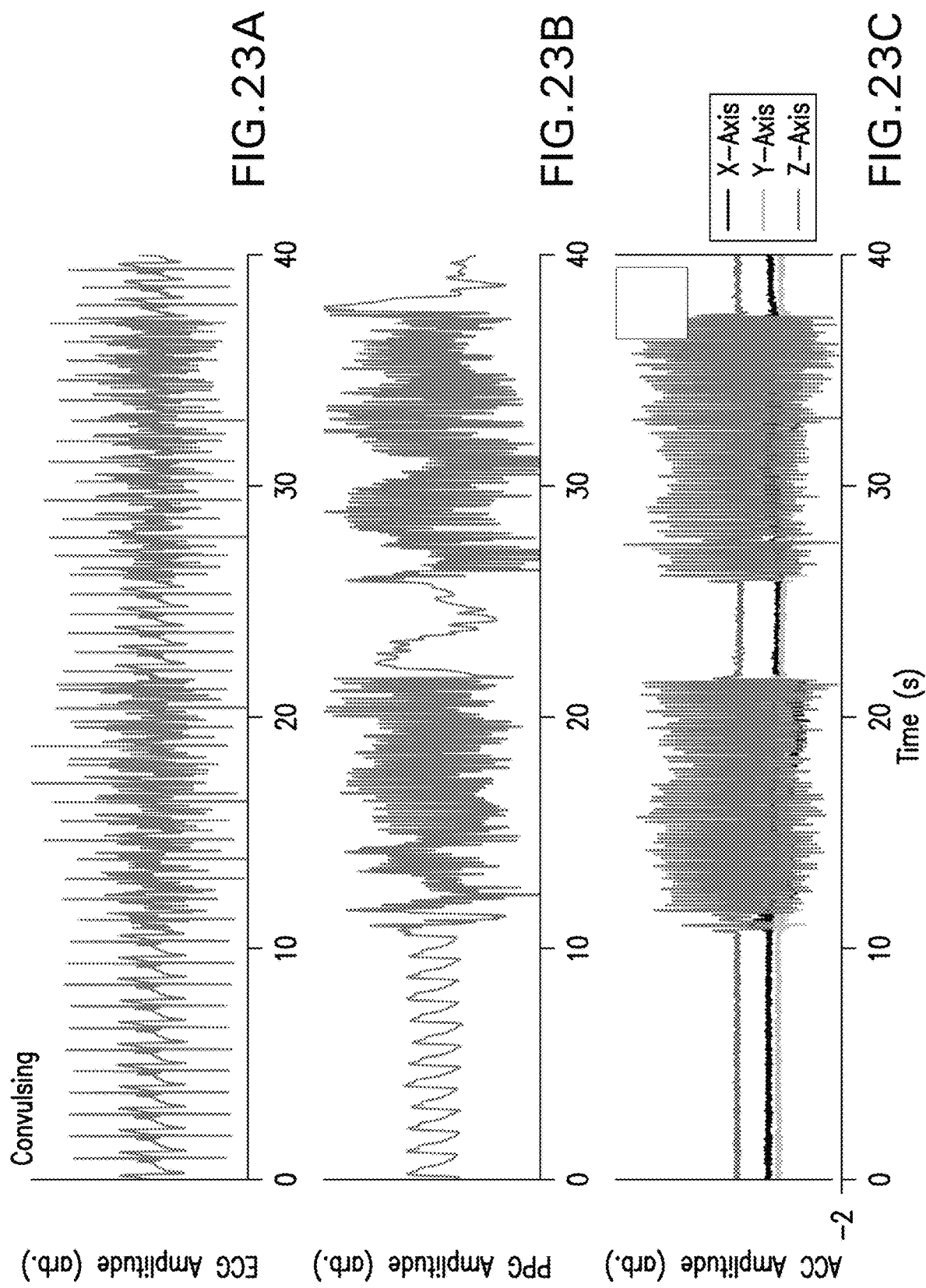

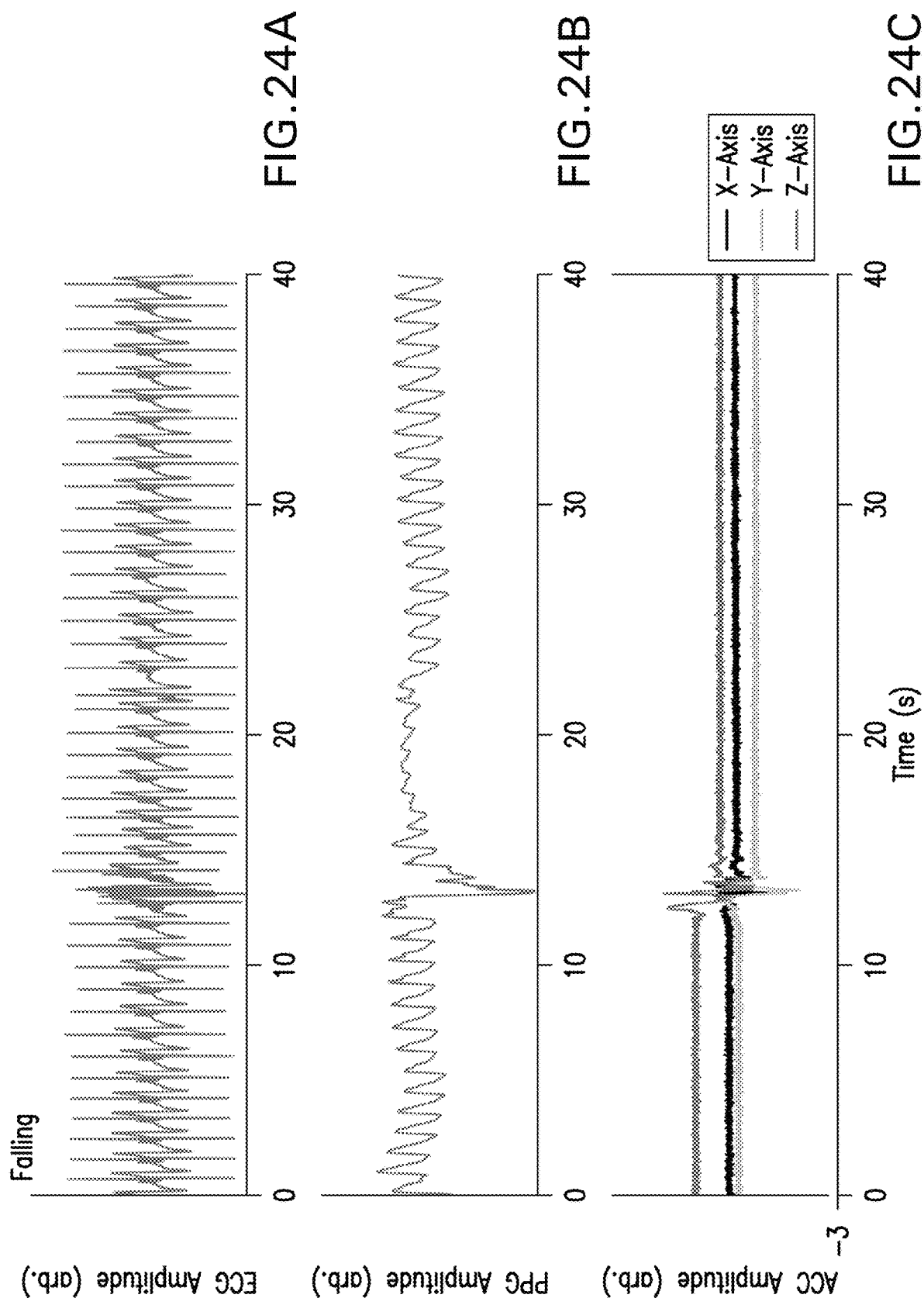

BODY-WORN MONITOR FOR MEASURING RESPIRATION RATE

CROSS REFERENCES TO RELATED APPLICATIONS

This application is a continuation of U.S. patent application Ser. No. 16/827,162, filed Mar. 23, 2020, which is a continuation of U.S. patent application Ser. No. 12/559,426, filed Sep. 14, 2009, now U.S. Pat. No. 10,595,746, which are hereby incorporated by reference in their entirety.

BACKGROUND OF THE INVENTION

Field of the Invention

The present invention relates to medical devices for monitoring vital signs, e.g., respiration rate.

Description of the Related Art

Respiration rate (RR) is a vital sign typically measured in the hospital using either an indirect electrode-based technique called 'impedance pneumography' (IP), a direct optical technique called 'end-tidal CO2' (et-CO2), or simply through manual counting of breaths by a medical professional. IP is typically used in lower-acuity areas of the hospital, and uses the same electrodes deployed in a conventional 'Einthoven's triangle' configuration for measuring heart rate (HR) from an electrocardiogram (ECG). One of the electrodes supplies a low-amperage (~4 mA) current that is typically modulated at a high frequency (~50-100 kHz). Current passes through a patient's chest cavity, which is characterized by a time-dependent capacitance that varies with each breath. A second electrode detects the current, which is modulated by the changing capacitance. Ultimately this yields an analog signal that is processed with a series of amplifiers and filters to detect the time-dependent capacitance change and, subsequently, the patient's RR.

In et-CO2, a device called a capnometer features a small plastic tube that typically inserts in the patient's mouth. With each breath the tube collects expelled CO2. A beam of infrared radiation emitted from an integrated light source passes through the CO2 and is absorbed in a time-dependent manner that varies with the breathing rate. A photodetector and series of processing electronics analyze the transmitted signal to determine RR. et-CO2 systems are typically used in high-acuity areas of the hospital, such as the intensive care unit (ICU), where patients often use ventilators to assist them in breathing.

In yet another technique, RR is measured from the envelope of a time-dependent optical waveform called a photoplethysmogram (PPG) that is measured from the index finger during a conventional measurement of the patient's oxygen saturation (SpO2). Breathing changes the oxygen content in the patient's blood and, subsequently, its optical absorption properties. Such changes cause a slight, low-frequency variation in the PPG that can be detected with a pulse oximeter's optical system, which typically operates at both red and infrared wavelengths.

Not surprisingly, RR is an important predictor of a decompensating patient. For example, a study in 1993 concluded that a respiratory rate greater than 27 breaths/minute was the most important predictor of cardiac arrests in hospital wards (Fieselmann et al., 'Respiratory rate predicts cardiopulmonary arrest for internal medicine patients', *J Gen Intern Med* 1993; 8: 354-360). Subbe et al. found that, in unstable patients, relative changes in respiratory rate were much greater than changes in heart rate or systolic blood pressure, and thus that the respiratory rate was likely to be a better means of discriminating between stable patients and patients at risk (Subbe et al., 'Effect of introducing the Modified Early Warning score on clinical outcomes, cardiopulmonary arrests and intensive care utilization in acute medical admissions', *Anaesthesia* 2003; 58: 797-802). Goldhill et al. reported that 21% of ward patients with a respiratory rate of 25-29 breaths/minute assessed by a critical care outreach service died in hospital (Goldhill et al., 'A physiologically-based early warning score for ward patients: the association between score and outcome', *Anaesthesia* 2005; 60: 547-553). Those with a higher respiratory rate had an even higher mortality rate. In another study, just over half of all patients suffering a serious adverse event on the general wards (e.g. a cardiac arrest or ICU admission) had a respiratory rate greater than 24 breaths/minute. These patients could have been identified as high risk up to 24 hours before the event with a specificity of over 95% (Cretikos et al., 'The Objective Medical Emergency Team Activation Criteria: a case—control study', *Resuscitation* 2007; 73: 62-72). Medical references such as these clearly indicate that an accurate, easy-to-use device for measuring respiratory rate is important for patient monitoring within the hospital.

Despite its importance and the large number of available monitoring techniques, RR is notoriously difficult to measure, particularly when a patient is moving. During periods of motion, non-invasive techniques based on IP and PPG signals are usually overwhelmed by artifacts and thus completely ineffective. This makes it difficult or impossible to measure RR from an ambulatory patient. Measurements based on et-CO2 are typically less susceptible to motion, but require a plastic tube inserted in the patient's mouth, which is typically impractical for ambulatory patients.

SUMMARY OF THE INVENTION

This invention provides methods, devices, and systems for use in measuring RR using multiple input signals, including IP, PPG, and ECG waveforms, and a signal processing technique based on adaptive filtering. After being measured with a body-worn system, these waveforms are processed along with those from an accelerometer mounted on the patient's torso (most typically the chest or abdomen). The accelerometer measures small, breathing-induced movements to generate a time-dependent waveform (ACC). With adaptive filtering, an initial RR is preferably estimated from the IP waveform, and alternatively from the PPG or ECG waveform. The initial RR is then processed and used to determine parameters for a bandpass digital filter, typically implemented with a finite impulse response function. This yields a customized filtering function which then processes the ACC waveform. The filtering function generates a relatively noise-free ACC waveform with well-defined pulses corresponding to RR. Each pulse can then be further processed and counted to determine an accurate RR value, even during periods of motion.

The body-worn monitor measures IP, PPG, ECG, and ACC waveforms with a series of sensors integrated into a comfortable, low-profile system that preferably communicates wirelessly with a remote computer in the hospital. The system typically features three accelerometers, each configured to measure a unique signal along its x, y, and z axes, to yield a total of nine ACC waveforms. In certain embodiments, the accelerometers are deployed on the patient's torso, upper arm, and lower arm, and may be embedded in the monitor's cabling or processing unit. Each ACC waveform can be additionally processed to determine the patient's posture, degree of motion, and activity level. These parameters serve as valuable information that can ultimately reduce occurrences of 'false positive' alarms/alerts in the hospital. For example, if processing of additional ACC waveforms indicates a patient is walking, then their RR rate, which may be affected by walking-induced artifacts, can be ignored by an alarm/alert engine associated with the body-worn monitor. The assumption in this case is that a walking patient is likely relatively healthy, regardless of their RR value. Perhaps more importantly, with a conventional monitoring device a walking patient may yield a noisy IP signal that is then processed to determine an artificially high RR, which then triggers a false alarm. Such a situation can be avoided with an independent measurement of motion, such as that described herein. Other heuristic rules based on analysis of ACC waveforms may also be deployed according to this invention.

Sensors attached to the wrist and bicep each measure signals that are collectively analyzed to estimate the patient's arm height; this can be used to improve accuracy of a continuous blood pressure measurement (cNIBP), as described below, that measures systolic (SYS), diastolic (DIA), and mean (MAP) arterial blood pressures. And the sensor attached to the patient's chest measures signals that are analyzed to determine posture and activity level, which can affect measurements for RR, SpO2, cNIBP, and other vital signs. Algorithms for processing information from the accelerometers for these purposes are described in detail in the following patent applications, the contents of which are fully incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009). As described therein, knowledge of a patient's motion, activity level, and posture can greatly enhance the accuracy of alarms/alerts generated by the body-worn monitor.

The body-worn monitor features systems for continuously monitoring patients in a hospital environment, and as the patient transfers from different areas in the hospital, and ultimately to the home. Both SpO2 and cNIBP rely on accurate measurement of PPG and ACC waveforms, along with an ECG, from patients that are both moving and at rest. cNIBP is typically measured with the 'Composite Technique', which is described in detail in the co-pending patent application entitled: VITAL SIGN MONITOR FOR MEASURING BLOOD PRESSURE USING OPTICAL, ELECTRICAL, AND PRESSURE WAVEFORMS (U.S. Ser. No. 12/138,194; filed Jun. 12, 2008), the contents of which are fully incorporated herein by reference.

As described in these applications, the Composite Technique (or, alternatively, the 'Hybrid Technique' referred to therein) typically uses a single PPG waveform from the SpO2 measurement (typically generated with infrared radiation), along with the ECG waveform, to calculate a parameter called 'pulse transit time' (PTT) which strongly correlates to blood pressure. Specifically, the ECG waveform features a sharply peaked QRS complex that indicates depolarization of the heart's left ventricle, and, informally, provides a time-dependent marker of a heart beat. PTT is the time separating the peak of the QRS complex and the onset, or 'foot', of the PPG waveforms. The QRS complex, along with the foot of each pulse in the PPG, can be used to more accurately extract AC signals using a mathematical technique described in detail below. In other embodiments both the red and infrared PPG waveforms are collectively processed to enhance the accuracy of the cNIBP measurement.

In certain embodiments, the electrical system for measuring RR features a small-scale, low-power circuit mounted on a circuit board that fits within the wrist-worn transceiver. The transceiver additionally includes a touchpanel display, barcode reader, and wireless systems for ancillary applications described, for example, in the above-referenced applications, the contents of which have been previously incorporated herein by reference.

In one aspect, the invention provides a multi-sensor system that uses an algorithm based on adaptive filtering to monitor a patient's RR. The system features a first sensor selected from the following group: i) an IP sensor featuring at least two electrodes and an IP processing circuit configured to measure an IP signal; ii) an ECG sensor featuring at least two electrodes and an ECG processing circuit configured to measure an ECG signal; and iii) a PPG sensor featuring a light source, photodetector, and PPG processing circuit configured to measure a PPG signal. Each of these sensors measures a time-dependent signal which is sensitive to RR and is processed to determine an initial RR value. The system features a second sensor (e.g. a digital 3-axis accelerometer) that attaches to the patient's torso and measures an ACC signal indicating movement of the chest or abdomen that is also sensitive to RR.

A body-worn processing system receives a first signal representing at least one of the IP, ECG, and PPG signals, and a second signal representing the ACC signal. The processing system is configured to: i) process the first signal to determine an initial RR; ii) process the second signal with a digital filter determined from the initial RR to determine a third signal; and iii) process the third signal to determine a final value for the patient's RR.

The processing system, as described herein, can include one or more microprocessors. For example, it can include first microprocessor embedded within a single ASIC that also measures IP and ECG, or mounted on a circuit board that also contains the ASIC or an equivalent circuit made from discrete components. In these cases the first microprocessor is mounted on the patient's torso. A wrist-worn transceiver can contain the second microprocessor. In embodiments, the first microprocessor mounted on the patient's torso determines a RR from multiple time-dependent signals; this value is transmitted to the second microprocessor within the wrist-worn transceiver as a digital or analog data stream transmitted through a cable. The second microprocessor further processes the RR value alongside data describing the patient's motion and other vital signs. The secondary processing, for example, can be used to generate alarms/alerts based on RR, or suppress alarms/alerts because of the patient's motion.

In embodiments, the digital filter used for adaptive filtering is a bandpass filter or low-pass filter. Typically the digital filter is determined from a finite impulse response function. The bandpass filter typically features an upper frequency limit determined from a multiple (e.g. 1-3×) of the initial RR. Such a digital filter is used to process time-dependent waveforms to remove noise and other artifacts to determine the initial version of RR. In this case the filter is not adaptive, and instead has a pre-determined passband. The final version of RR is determined from the adaptive filter, which as described above has a passband that depends on the initial version of RR.

In other embodiments, the processing system is further configured to determine both initial and final versions of RR by processing a filtered waveform with a mathematical derivative and then determine a zero-point crossing indicating a 'count' marking a respiratory event. Such counts are evident in the processed IP signal, which features a first series of pulses that, once analyzed by the processing system, yields the initial RR. Alternatively, the initial RR is determined from either an ECG or PPG, both of which feature a series of heartbeat-induced pulses with amplitudes characterized by a time-varying envelope, with the frequency of the envelope representing the initial RR. The waveforms used to determine the initial and final values for RR can be interchanged, e.g. the ACC waveform can be processed to determine the initial RR value, and this can then be used to design a digital filter that processes the IP, ECG, or PPG waveforms to determine the final RR value. In general, according to the invention, any combination of the above-described waveforms can be used in the adaptive filtering process to determine the initial and final RR values.

In another aspect, the invention provides a system for monitoring a patient's RR that also accounts for their posture, activity level, and degree of motion. Such patient states can result in artifacts that affect the RR measurement, and thus proper interpretation of them can reduce the occurrence of erroneous RR values and ultimately false alarms/alerts in the hospital.

In another aspect, the invention provides a cable within a body-worn monitor that includes an IP system, a motion sensor (e.g. accelerometer), and a processing system that determines RR from signals generated by these sensors. These components, for example, can be included in a terminal end of the cable, typically worn on the patient's torso, which connects to a series of disposable electrodes that attach to the patient's body. A mechanical housing, typically made of plastic, covers these and other components, such as sensors for measuring signals relating to ECG and skin temperature.

In embodiments, the cable includes at least one conductor configured to transmit both a first digital data stream representing the digital IP signal or information calculated therefrom, and a second digital data stream representing the digital motion signal or information calculated therefrom. In other embodiments these signals are processed by a microprocessor on the chest to determine an RR value, and this value is then sent in the digital data stream to another processor, such as one within the wrist-worn transceiver, where it is further processed. To transmit the serial data stream, the terminal portion of the cable can include a transceiver component, e.g. a serial transceiver configured to transmit a digital data stream according to the CAN protocol. Other properties, such as heart rate, temperature, alarms relating to ECG signals, and other information relating to the CAN communication protocol and its timing can be transmitted by the transceiver component.

In embodiments, both the IP and ECG systems are contained within a single integrated circuit. The ECG system can be modular and determine multi-lead ECG signals, such as three, five, and twelve-lead ECG signals.

In another aspect, the invention provides a method for determining RR during periods of motion. The method includes the following steps: (a) measuring a first time-dependent signal by detecting a modulated electrical current passing through the patient's torso; (b) measuring a second time-dependent signal by detecting respiration-induced movements in the patient's torso with at least one motion sensor; (c) determining a motion-related event not related to the patient's respiration rate value by processing signals from the motion sensor; and (d) collectively processing both the first and second time-dependent signals to determine a value for RR corresponding to a period when the patient's motion-related event is below a pre-determined threshold. For example, the motion-related event determined during step (c) can be the patient's posture, activity level, or degree of motion. Typically these parameters are determined from signals measured with an accelerometer mounted on the patient's torso. These signals are processed with an algorithm, described in detail below, that yields a vector indicating orientation of the patient's chest and their subsequent posture. Specifically, an angle separating the vector from a pre-determined coordinate system ultimately yields posture, as is described in detail below. Activity level (corresponding, e.g., to moving, walking, falling, convulsing) can be calculated from a mathematical transform of time-dependent variations of a motion signal that yields a frequency-domain spectrum. Portions of the spectrum (e.g. the power of specific frequency components) are compared to pre-determined frequency parameters to determine the activity level. Other operations, such as a mathematical derivative of the time-dependent motion signal, or a series of 'decision rules' based on a decision-tree algorithm, can also yield the activity level.

In another aspect, the invention provides a method for suppressing alarms related to RR by processing the patient's posture, activity level, and degree of motion as determined by the accelerometer. For example, the alarm can be suppressed if the patient is standing upright, or if their posture changes from lying down to one of sitting and standing upright. Or the alarm can be suppressed if their posture changes from either standing upright or sitting to lying down. In general, a rapid change in posture, which can be determined with the chest-worn accelerometer, may disrupt the signals used to determine RR to the point where a false alarm/alert is generated. In this embodiment, posture is determined from the vector-based analysis, described above.

In yet another aspect, the invention provides a system for monitoring a patient's RR featuring a sensor unit configured to be mounted on the patient's torso. The sensor unit features IP and motion sensors, as described above, and additionally attaches directly to an electrode that secures the unit to the patient's torso (e.g. chest or abdomen). Here, a housing comprising the IP and motion sensors additionally includes a connector featuring an opening configured to receive a metal snap on the exterior of a conventional disposable electrode. Other electrodes used for IP and ECG measurements connect to the unit through cables. The unit can additionally send a digital data stream including RR data over a CAN bus to a wrist-worn transceiver, which as described above can further process the RR value to account for alarms/alerts, motion, etc.

In all embodiments, the wrist-worn transceiver can include a display configured to display the patient's RR and other vital signs, along with a touchpanel interface. A wireless transceiver within the wrist-worn transceiver can transmit information to a remote computer using conventional protocols such as 802.11, 802.15.4, and cellular. The remote computer, for example, can be connected to a hospital network. It can also be a portable computer, such as a tablet computer, personal digital assistant, or cellular phone.

Many advantages are associated with this invention. In general, it provides an accurate measurement of RR, along with an independent measurement of a patient's posture, activity level, and motion, to characterize an ambulatory patient in the hospital. These parameters can be collectively analyzed to improve true positive alarms while reducing the occurrence of false positive alarms. Additionally, the measurement of RR is performed with a body-worn monitor that is comfortable, lightweight, and low-profile, making it particularly well suited for patients that are moving about. Such a monitor could continuously monitor a patient as, for example, they transition from the emergency department to the ICU, and ultimately to the home after hospitalization.

Still other embodiments are found in the following detailed description of the invention and in the claims.

BRIEF DESCRIPTION OF THE DRAWINGS

FIG. 1A shows a schematic view of a patient wearing accelerometers on their abdomen (position 1) and chest (position 2) to measure ACC waveforms and RR according to the adaptive filtering process of the invention;

FIG. 1B shows a schematic view of the accelerometers from FIG. 1 along with their three-dimensional measurement axes;

FIG. 2A shows a schematic view of a patient wearing ECG electrodes on their chest in a conventional Einthoven's triangle configuration to measure an IP waveform;

FIG. 2B shows a schematic view of ECG and IP circuits that simultaneously process signals from each ECG electrode in FIG. 2A to determine both ECG and IP waveforms;

FIGS. 5A-C show an ACC waveform filtered with a 0.01→0.1 Hz bandpass filter (FIG. 5A; top), an IP waveform (FIG. 5B), and a et-CO2 waveform (FIG. 5C; bottom) simultaneously measured from a supine patient undergoing fast, deep breaths;

FIGS. 8A-C show an ACC waveform filtered with a 0.01→0.1 Hz bandpass filter (FIG. 8A; top), an IP waveform (FIG. 8B), and a et-CO2 waveform (FIG. 8C; bottom) simultaneously measured from a standing patient undergoing medium, shallow breaths;

FIGS. 9A-C show an ACC waveform filtered with a 0.01→0.1 Hz bandpass filter (FIG. 9A; top), an IP waveform (FIG. 9B), and a et-CO2 waveform (FIG. 9C; bottom) simultaneously measured from a standing patient undergoing fast, deep breaths;

FIGS. 10A-C show an ACC waveform filtered with a 0.01→0.1 Hz bandpass filter (FIG. 10A; top), an IP waveform (FIG. 10B), and a et-CO2 waveform (FIG. 10C; bottom) simultaneously measured from a supine patient undergoing slow, deep breaths, followed by a period of apnea, followed by relatively fast, deep breaths;

FIGS. 15A-E show graphs of an ACC waveform filtered initially with a 0.01→2 Hz bandpass filter (FIG. 15A; top), an IP waveform filtered initially with a 0.01→12 Hz bandpass (FIG. 15B), an ACC waveform adaptively filtered with a bandpass filter ranging from 0.01 Hz to 1.5 times the breathing rate calculated from the IP waveform in FIG. 15B (FIG. 15C), a first derivative of the filtered waveform in FIG. 15C (FIG. 15D), and the adaptively filtered waveform in FIG. 15C along with markers (FIG. 15E; bottom) indicating slow, deep breaths as determined from the algorithm shown by the flow chart in FIG. 14;

FIGS. 18A-B show graphs of an ACC waveform filtered initially with a 0.01→2 Hz bandpass filter (FIG. 18A; top), and an IP waveform filtered initially with a 0.01→12 Hz bandpass (FIG. 18B; bottom) measured from a walking patient;

FIG. 18C is a flow chart showing the algorithmic steps used to process the waveforms shown in FIGS. 18A-B;

FIG. 20A is a graph showing an unfiltered ECG waveform measured from a resting patient;

FIG. 20B is a graph showing the time-dependent envelope of the ECG waveform shown in FIG. 20A;

FIG. 20C is a graph showing an unfiltered PPG waveform measured simultaneously with the ECG waveform of FIG. 20A;

FIG. 20D is a graph showing the time-dependent envelope of the PPG waveform shown in FIG. 20C;

FIG. 20E is a graph showing an IP waveform measured simultaneously with the ECG waveform of FIG. 20A and the PPG waveform of FIG. 20C;

FIGS. 21A-C show graphs of time-dependent ECG waveforms (FIG. 21A; top), PPG waveforms (FIG. 21B), and ACC waveforms (FIG. 21C; bottom) measured along the x, y, and z-axes for a resting patient;

FIGS. 22A-C show graphs of time-dependent ECG waveforms (FIG. 22A; top), PPG waveforms (FIG. 22B), and ACC waveforms (FIG. 22C; bottom) measured along the x, y, and z-axes for a walking patient;

FIGS. 23A-C show graphs of time-dependent ECG waveforms (FIG. 23A; top), PPG waveforms (FIG. 23B), and ACC waveforms (FIG. 23C; bottom) measured along the x, y, and z-axes for a convulsing patient;

FIGS. 24A-C show graphs of time-dependent ECG waveforms (FIG. 24A; top), PPG waveforms (FIG. 24B), and ACC waveforms (FIG. 24C; bottom) measured along the x, y, and z-axes for a falling patient;

DETAILED DESCRIPTION OF THE INVENTION

Sensor Configuration

Figure 3A:
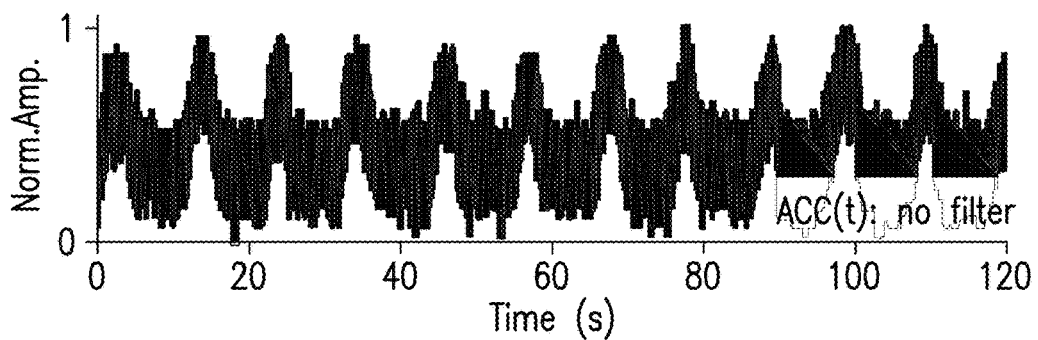
FIGS. 3A-D each show an ACC waveform measured with the configuration shown in FIG. 1 after processing with no filter (FIG. 3A; top), a 0.01→1 Hz bandpass filter (FIG. 3B), a 0.01→0.5 Hz bandpass filter (FIG. 3C), and a 0.01→0.1 Hz bandpass filter (FIG. 3C; bottom)

Referring to FIGS. 1A and 1B, a pair of accelerometers 12, 14 attach, respectively, to the chest and abdomen of a patient 10 to predict RR through the patient's torso movement and an algorithm based on adaptive filtering. Each accelerometer 12, 14 simultaneously measures acceleration (e.g. motion) along x, y, and z axes of a local coordinate system 18. As shown in FIG. 1B, the accelerometers 12, 14 are preferably aligned so the z axis points into the patient's torso. Within each accelerometer 12, 14 is an internal analog-to-digital converter that generates a digital ACC waveform 19 corresponding to each axis. Waveforms are sent as a stream of digital data to a wrist-worn transceiver (shown, for example, in FIGS. 27A, B, and 28) where they are processed using an adaptive filtering algorithm described in detail below to determine the patient's RR. Alternatively, the adaptive filtering algorithm can be performed with a microprocessor mounted proximal to the accelerometers 12, 14 on the patient's torso. Additional properties such as the patient's posture, degree of motion, and activity level are determined from these same digital ACC waveforms. As indicated by FIG. 1B, the axis within the accelerometer's coordinate system 18 that is aligned along the patient's torso (and thus orthogonal to their respiration-induced torso movement) is typically more sensitive to events not related to respiration, e.g. walking and falling.

In a preferred embodiment, digital accelerometers manufactured by Analog Devices (e.g. the ADXL345 component) are used in the configuration shown in FIG. 1A. These sensors detect acceleration over a range of +/−2 g (or, alternatively, up to +/−8 g) with a small-scale, low-power circuit.

Many patient's are classified as 'abdomen breathers', meaning during respiration their abdomen undergoes larger movements than their chest. A relative minority of patients are 'chest breathers', indicating that it is the chest that undergoes the larger movements. For this reason it is preferred that RR is determined using an ACC waveform detected along the z-axis with an accelerometer 14 positioned on the patient's abdomen. In alternate configurations the accelerometer 12 on the chest can be used in its place or two augment data collected with the abdomen-mounted sensor. Typically, ACC waveforms along multiple axes (e.g. the x and y-axes) are also modulated by breathing patterns, and can thus be used to estimate RR. In still other configurations multiple signals from one or both accelerometers 12, 14 are collectively processed to determine a single 'effective' ACC waveform representing, e.g., an average of the two waveforms. This waveform is then processed using adaptive filtering to determine the patient's RR.

As shown in FIGS. 2A and 2B, ECG waveforms are simultaneously measured with the ACC waveforms using a trio of electrodes 20, 22, 24 typically positioned on the chest of the patient 10 in an Einthoven's triangle configuration. During a measurement, each electrode 20, 22, 24 measures a unique analog signal that passes through a shielded cable to an ECG circuit 26, which is typically mounted in a small plastic box 25 attached to the patient's chest. The ECG circuit 26 typically includes a differential amplifier and a series of analog filters with passbands that pass the high and low-frequency components that contribute to the ECG waveform 28, but filter out components associated with electrical and mechanical noise. Also within the box 25 is an accelerometer 12 and, alternatively as described above, a microprocessor for performing the adaptive filtering algorithm. A conventional analog ECG waveform 28, such as that shown in FIG. 20A, features a series of heartbeat-induced pulses, each characterized by a well-known 'QRS complex' that, informally, marks the initial depolarization of the patient's heart. To determine RR, a separate IP circuit 27 within the plastic box 25 generates a low-amperage current (typically 1-4 mA) that is modulated at a high frequency (typically 50-100 kHz). The current typically passes through electrode LL ('lower left') 24, which is located on the lower left-hand side of the patient's torso. It then propagates through the patient's chest, as indicated by the arrow 29, where a respiration-induced capacitance change modulates it according to the RR. Electrode UR ('upper right') 20 detects the resultant analog signal, which is then processed with a separate differential amplifier and series of analog filters within the IP circuit to determine an analog IP waveform 30 featuring a low-frequency series of pulses corresponding to RR. Typically the analog filters in the IP circuit 27 are chosen to filter out high-frequency components that contribute to the ECG QRS complex.

In other embodiments, the plastic box includes a temperature sensor 33, such as a conventional thermocouple, that measures the skin temperature of the patient's chest. This temperature is typically a few degrees lower than conventional core temperature, usually measured with a thermometer inserted in the patient's throat or rectum. Despite this discrepancy, skin temperature measured with the temperature sensor 33 can be monitored continuously and can therefore be used along with RR and other vital signs to predict patient decompensation.

In a preferred embodiment, both the ECG 28 and IP 30 waveforms are generated with a single application-specific integrated circuit (ASIC), or a circuit composed of a series of discrete elements which are known in the art. Preferably the ECG circuit includes an internal analog-to-digital converter that digitizes both waveforms before transmission to the wrist-worn transceiver for further processing. This circuitry, along with that associated with both the ECG and IP circuits, is contained within a single, small-scale electronic package.

Transmission of digital IP, ECG, and ACC waveforms, along with processed RR values, has several advantages over transmission of analog waveforms. First, a single transmission line in the monitor's cabling can transmit multiple digital waveforms, each generated by different sensors. This includes multiple ECG waveforms 28 (corresponding, e.g., to vectors associated with three, five, and twelve-lead ECG systems) from the ECG circuit 26, the IP waveform 30 from the IP circuit 27, and ACC waveforms 19 associated with the x, y, and z axes of accelerometers 10, 12 attached to the patient's chest. Limiting the transmission line to a single cable reduces the number of wires attached to the patient, thereby decreasing the weight and cable-related clutter of the body-worn monitor. Second, cable motion induced by an ambulatory patient can change the electrical properties (e.g. electrical impendence) of its internal wires. This, in turn, can add noise to an analog signal and ultimately the vital sign calculated from it. A digital signal, in contrast, is relatively immune to such motion-induced artifacts. More sophisticated ECG circuits can plug into the wrist-worn transceiver to replace the three-lead system shown in FIG. 2A. These ECG circuits can include, e.g., five and twelve leads.

Digital data streams are typically transmitted to the wrist-worn transceiver using a serial protocol, such as a controlled area network (CAN) protocol, USB protocol, or RS-232 protocol. CAN is the preferred protocol for the body-worn monitor described in FIGS. 27A, 27B.

Determining RR from ACC Waveforms

Accelerometers positioned in the above-described locations on the patient's torso can detect respiration-induced motion associated with the chest and abdomen, and can therefore be processed to determine RR. Digital filtering is typically required to remove unwanted noise from the ACC waveform and isolate signal components corresponding to RR. Good filtering is required since respiratory-induced motions are typically small compared to those corresponding to activities (e.g. walking, falling) and posture changes (e.g. standing up, sitting down) associated with a patient's motion. Often these signals are only slightly larger than the accelerometer's noise floor.

Figure 3B:
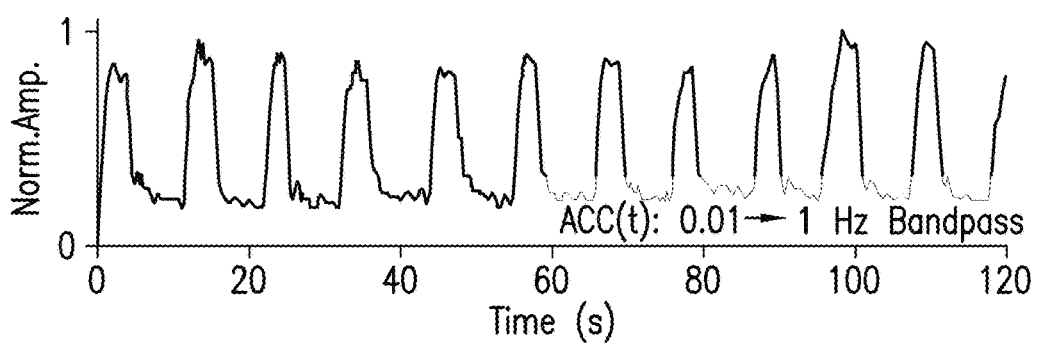

FIGS. 3A-3D show a common, normalized ACC waveform without any filtering (FIG. 3A), and then filtered with a progressively narrow digital bandpass filter generated from a finite impulse response function featuring 1048 coefficients. FIGS. 3E-3H show the first derivative of these waveforms, and feature a zero-point crossing corresponding to a positive-to-negative slope change of a single pulse in the ACC waveform. This feature can be easily analyzed with a computer algorithm to count the various pulses that contribute to RR. As shown in FIG. 3A (the top figure), an unfiltered ACC waveform typically includes a series of respiration-induced pulses characterized by a peak amplitude which, in this case, is roughly twice that of the noise floor. This poor signal-to-noise ratio yields a derivatized signal in FIG. 3E that has no discernible zero-point crossing, thus making it nearly impossible to analyze. As shown in FIG. 3B, a relatively wide bandpass filter (0.01→1 Hz) yields an ACC waveform with a significantly improved signal-to-noise ratio. Still, as shown in FIG. 3F, the derivative of this waveform features a primary zero-point crossing occurring near 25 seconds, and a series of artificial noise-induced crossings, both before and after the primary crossing, that could be erroneously counted by an algorithm to yield an artificially high value for RR.

Figure 3C:
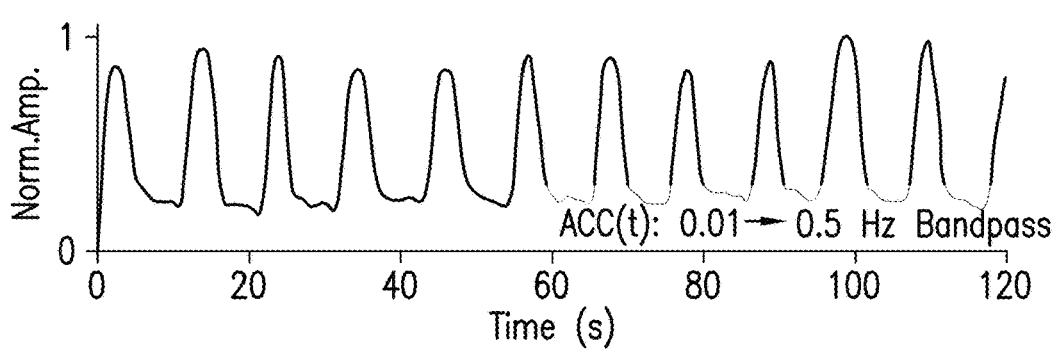
Figure 3D:
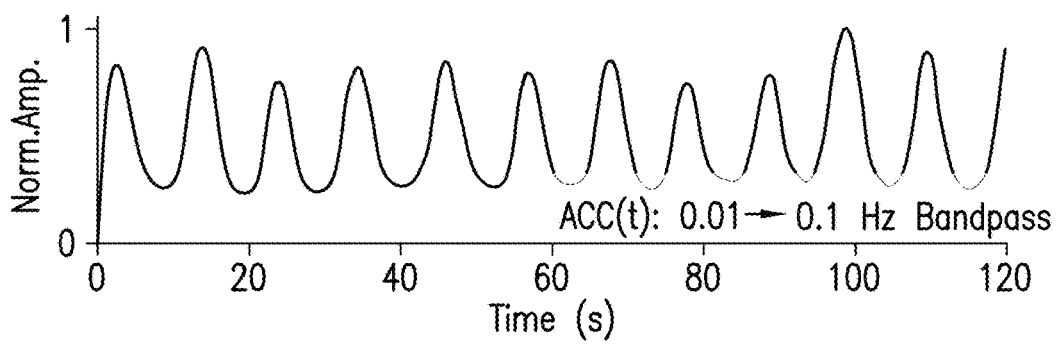
Figure 3E:
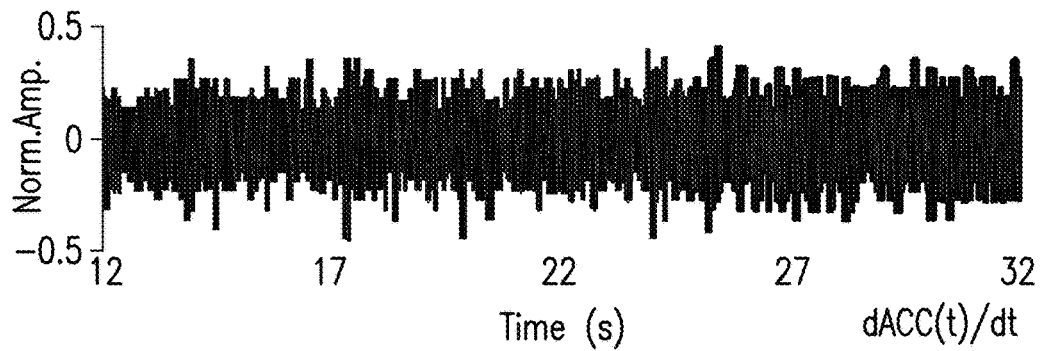
FIGS. 3E-H show, respectively, time-dependent derivatives of the ACC waveforms shown in FIGS. 3A-D.
Figure 3F:
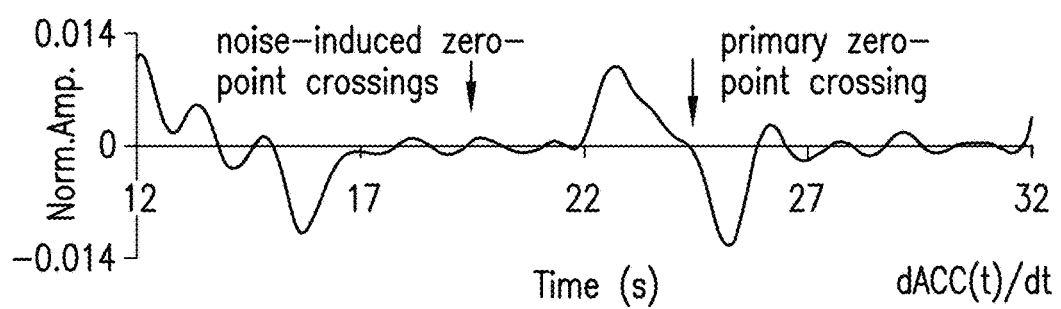
Figure 3G:
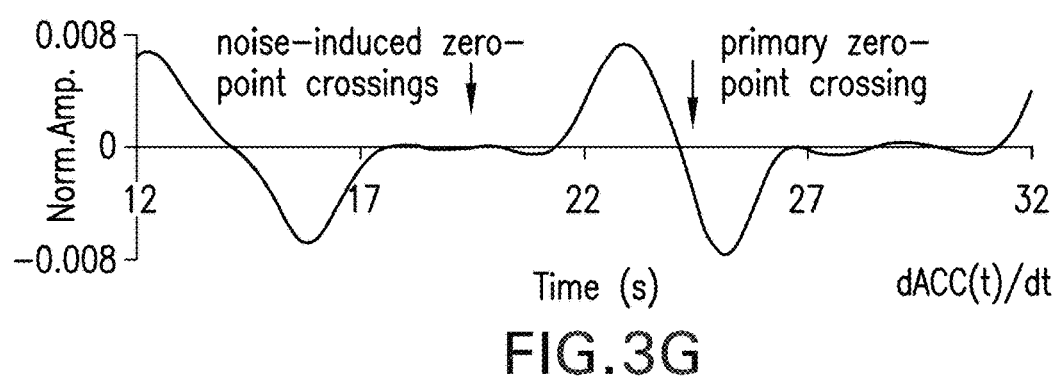
Figure 3H:
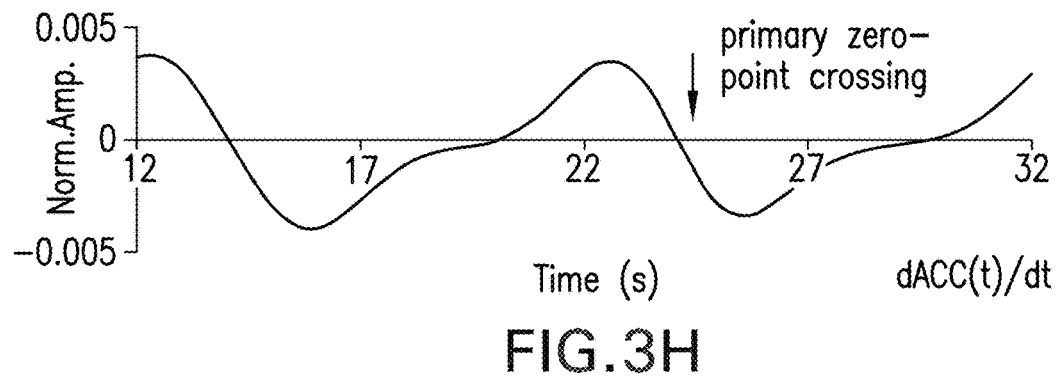
Figure 4A:
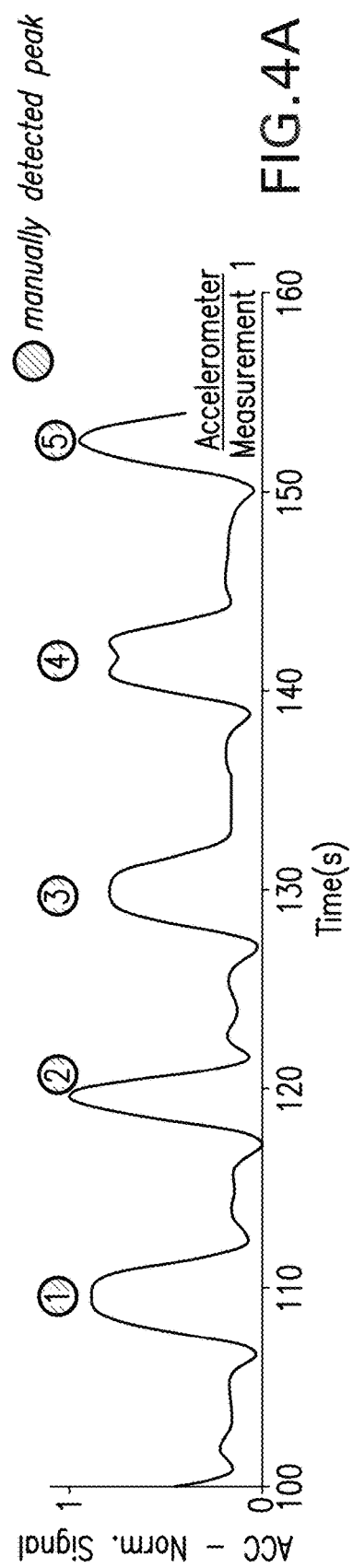
FIGS. 4A-C show an ACC waveform filtered with a 0.01→0.1 Hz bandpass filter (FIG. 4A; top), an IP waveform (FIG. 4B), and a et-CO2 waveform (FIG. 4C; bottom) simultaneously measured from a supine patient undergoing slow, deep breaths.
Figure 4B:
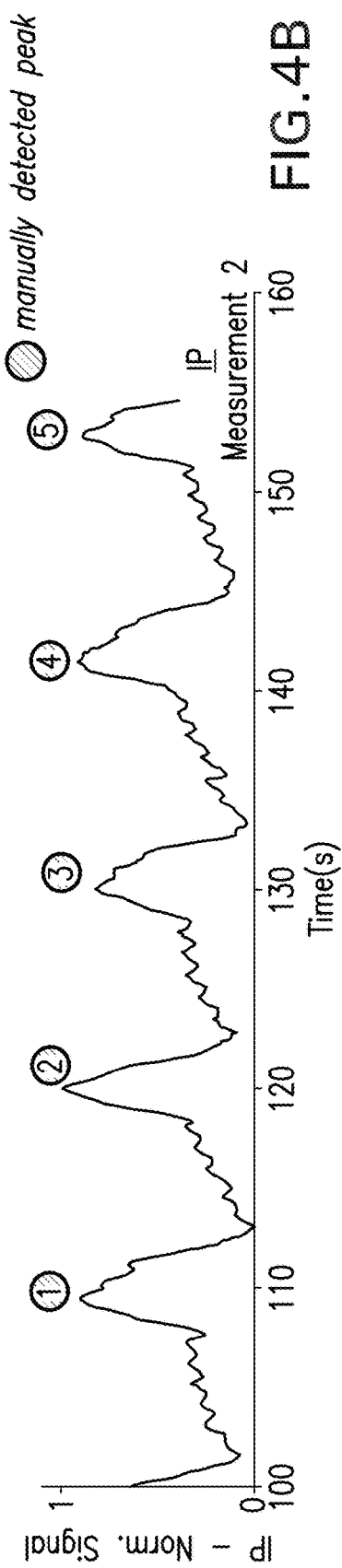
Figure 4C:
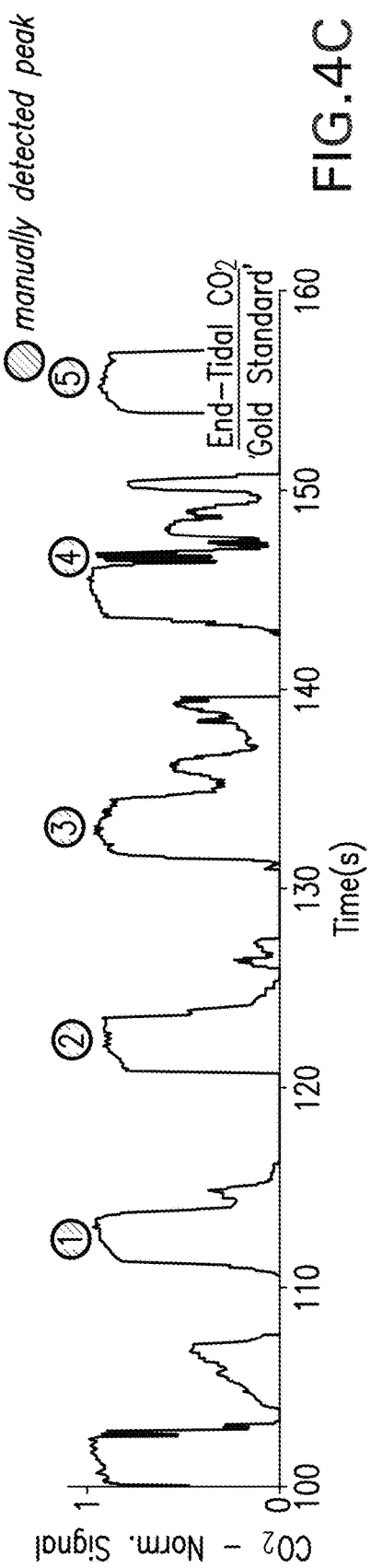
Figure 6A:
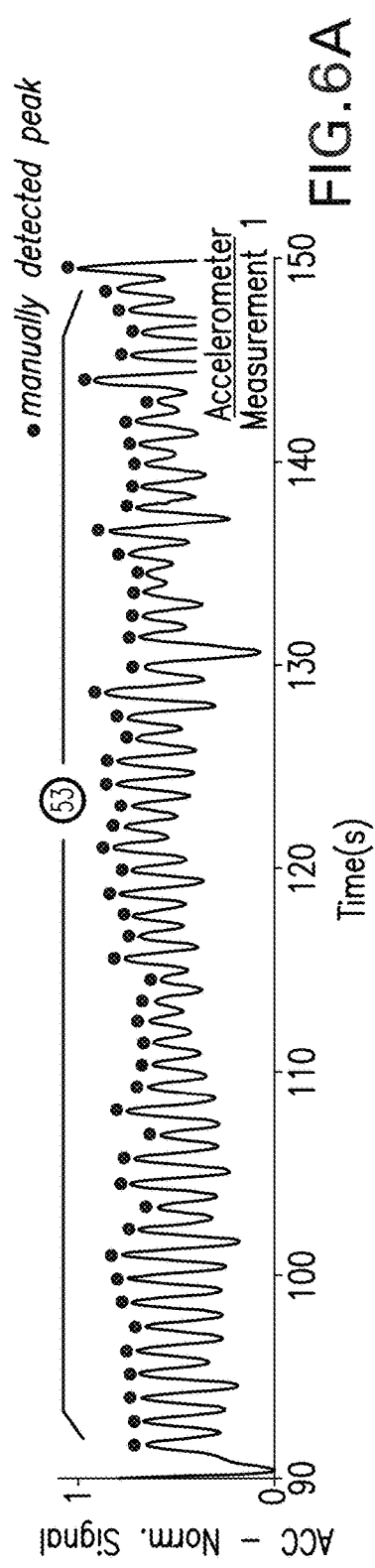
FIGS. 6A-C show an ACC waveform filtered with a 0.01→0.1 Hz bandpass filter (FIG. 6A; top), an IP waveform (FIG. 6B), and a et-CO2 waveform (FIG. 6C; bottom) simultaneously measured from a supine patient undergoing very fast, deep breaths.
Figure 6B:
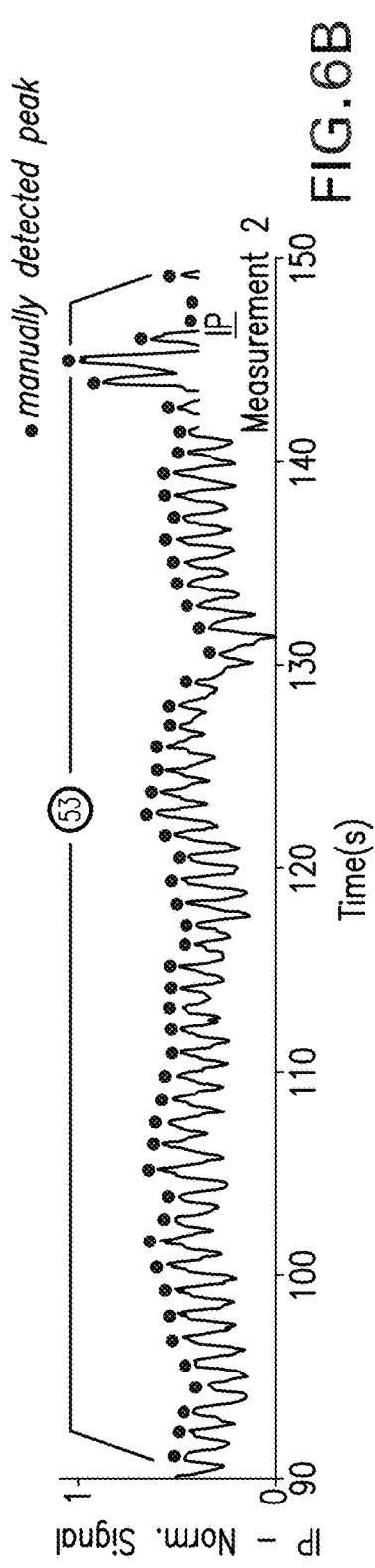
Figure 6C:
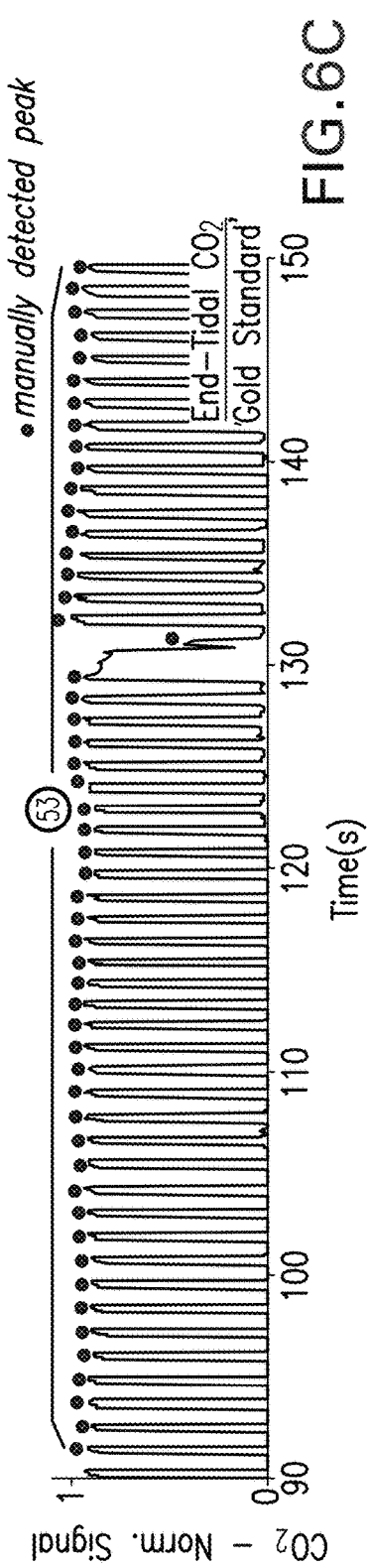

FIGS. 3C and 3G show, respectively, an ACC waveform and corresponding first derivative that result from a relatively narrow 0.01→0.5 Hz bandpass filter. These signals have higher signal-to-noise ratios than those shown in FIGS. 3B, 3F, but still include artificial zero-point crossings on both sides of the primary zero-point crossing. While small, these features still have the potential to yield an artificially high value for RR. The signals shown in FIGS. 3D, 3H, in contrast, are ideal. Here, a narrow 0.01→0.1 Hz bandpass filter removes high-frequency components associated with artifacts in the ACC waveform, and in the process removes similar frequency components that contribute to sharp rising and falling edges of the individual breathing-induced pulses. This generates a smooth, sinusoid-shaped pulse train that once derivatized, as shown in FIG. 3H, yields a clean signal with only a single zero-point crossing. An algorithm can easily analyze this to determine RR. Importantly, as indicated by the alignment of the primary zero-point crossing in FIGS. 3F, 3G, and 3H, the finite impulse response function introduces little or no phase shift in the ACC waveforms.

As shown in FIGS. 4-9, under ideal conditions RR determined from a filtered ACC waveform agrees well with that determined from IP, which is a signal used during the adaptive filtering algorithm described herein, and et-CO2, which represents a 'quasi' gold standard for determining RR. Data shown in each of these figures were collected simultaneously. ACC and IP waveforms were collected using an accelerometer mounted on a patient's abdomen, similar to that shown in FIG. 1A, and a trio of electrodes mounted in an Einthoven's triangle configuration, similar to that shown in FIG. 2A. The IP waveform is unfiltered, while the ACC waveform is filtered with a 0.01→0.1 Hz bandpass filter, as described with reference to FIGS. 3A, 3H. et-CO2 was measured with a separate sensor positioned within the patient's mouth; signals from this sensor were not filtered in any way. In all cases breathing-induced pulses corresponding to RR were determined manually, and are marked accordingly in the figures. Numerical values within the markers indicate the exact number of counted pulses.

FIGS. 4-9 indicate that RR determined from both IP and ACC waveforms correlates well to absolute RR determined from et-CO2. The correlation holds for a variety of breathing conditions, ranging from slow, deep breathing (FIGS.

Figure 7A:
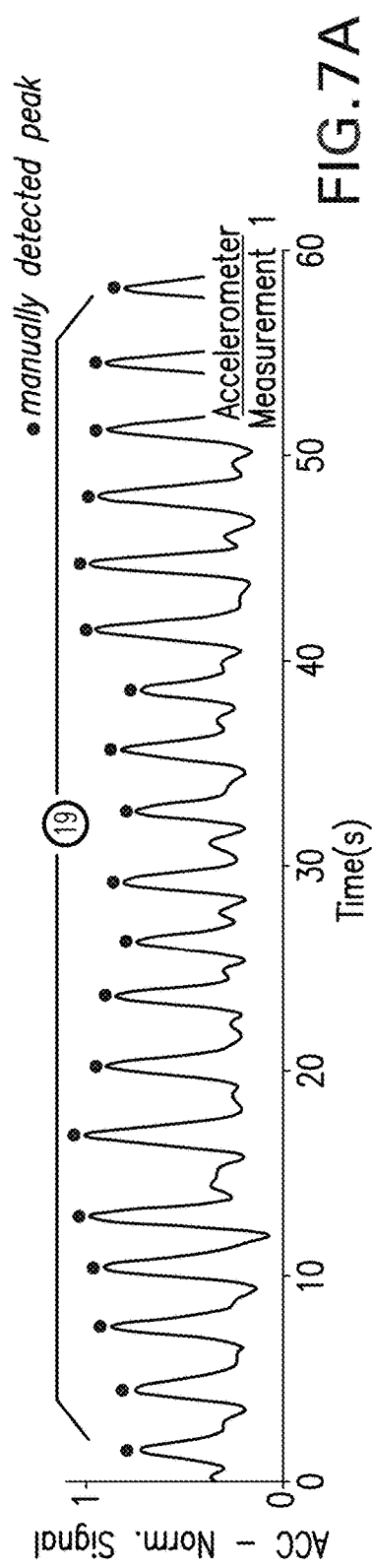
FIGS. 7A-C show an ACC waveform filtered with a 0.01→0.1 Hz bandpass filter (FIG. 7A; top), an IP waveform (FIG. 7B), and a et-CO2 waveform (FIG. 7C; bottom) simultaneously measured from a supine patient undergoing medium, shallow breaths.
Figure 7B:
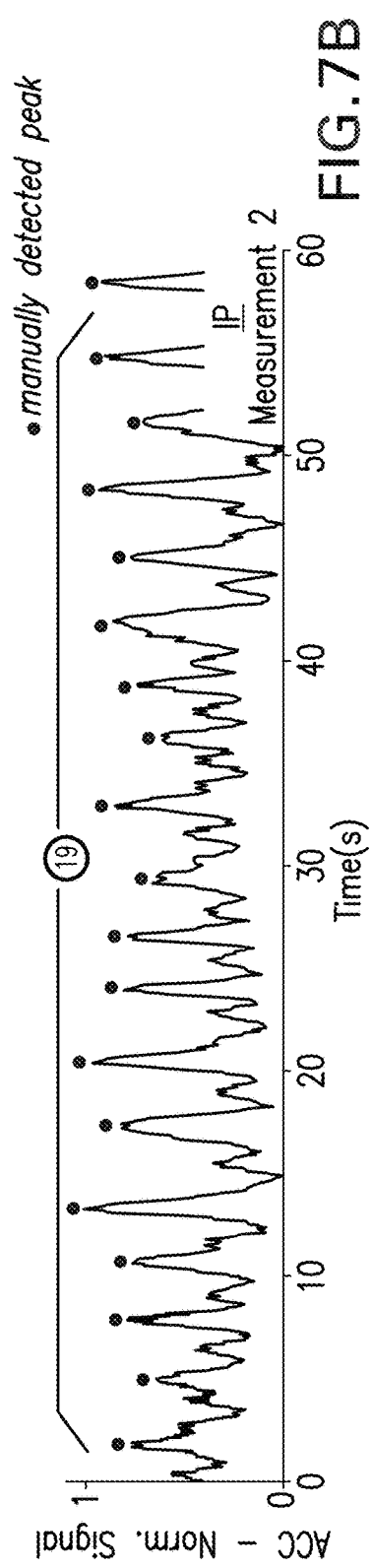
Figure 7C:
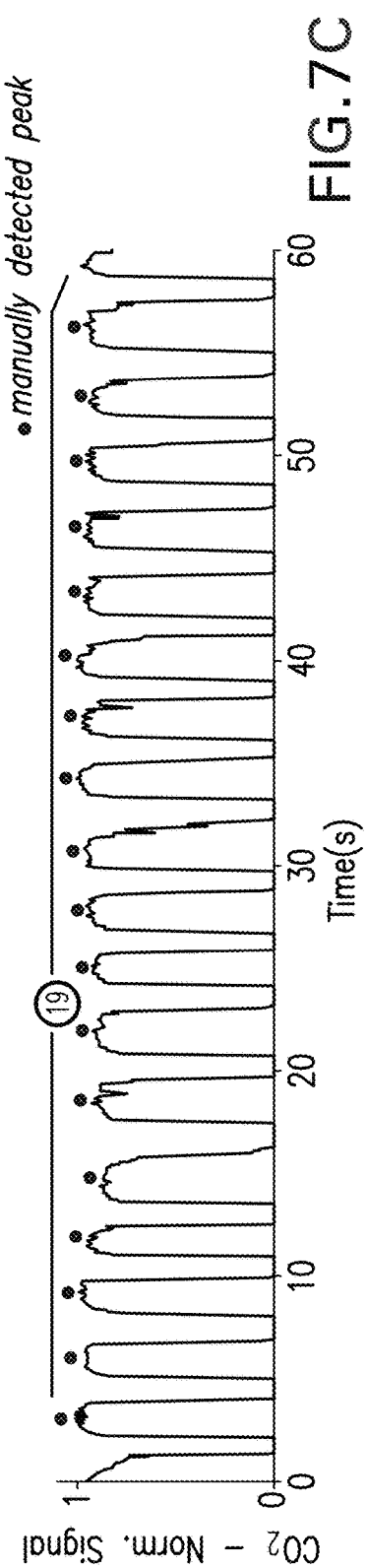

4A-4C); fast, deep breathing (FIGS. 5A-5C); very fast, deep breathing (FIGS. 6A-6C); and shallow, slow breathing (FIGS. 7A-7C). Data were measured under these conditions from a patient in a prone (i.e. lying down) posture. Additionally, the agreement continues to hold for a standing patient undergoing deep, slow breathing (FIG. 8A-8C) and deep, fast breathing (FIG. 9A-9C). Even with this range of configurations, RR determined from both ACC and IP waveforms agreed to within 1 breath/minute to that determined from et-CO2. In most cases the filtered ACC waveform appeared to have a superior signal-to-noise ratio when compared to the IP waveform, with the case for slow, deep breathing for a standing patient (FIGS. 8A-C) being the one exception.

Figure 11A:
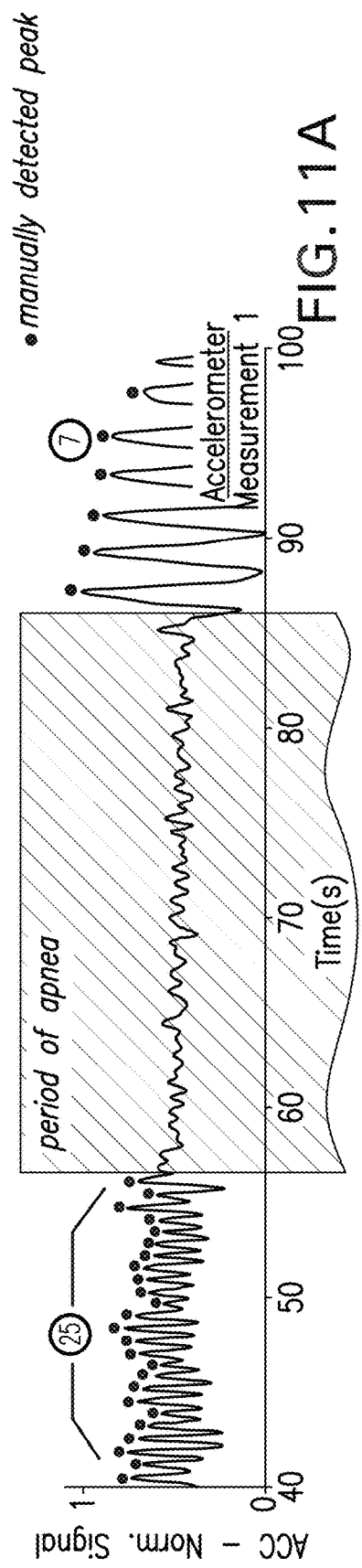
FIGS. 11A-C show an ACC waveform filtered with a 0.01→0.1 Hz bandpass filter (FIG. 11A; top), an IP waveform (FIG. 11B), and a et-CO2 waveform (FIG. 11C; bottom) simultaneously measured from a supine patient undergoing very fast, shallow breaths, followed by a period of apnea, followed by relatively slow, shallow breaths.
Figure 11B:
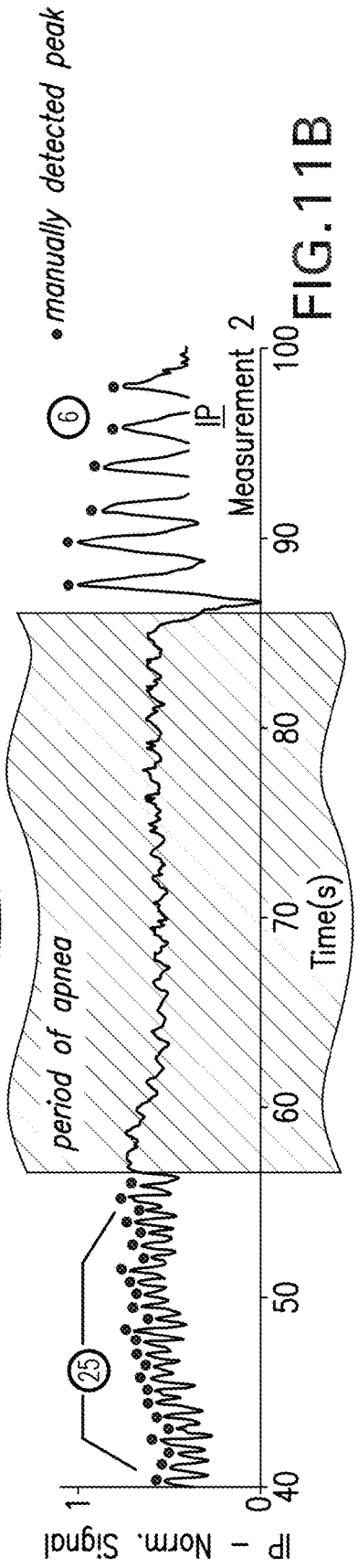
Figure 11C:
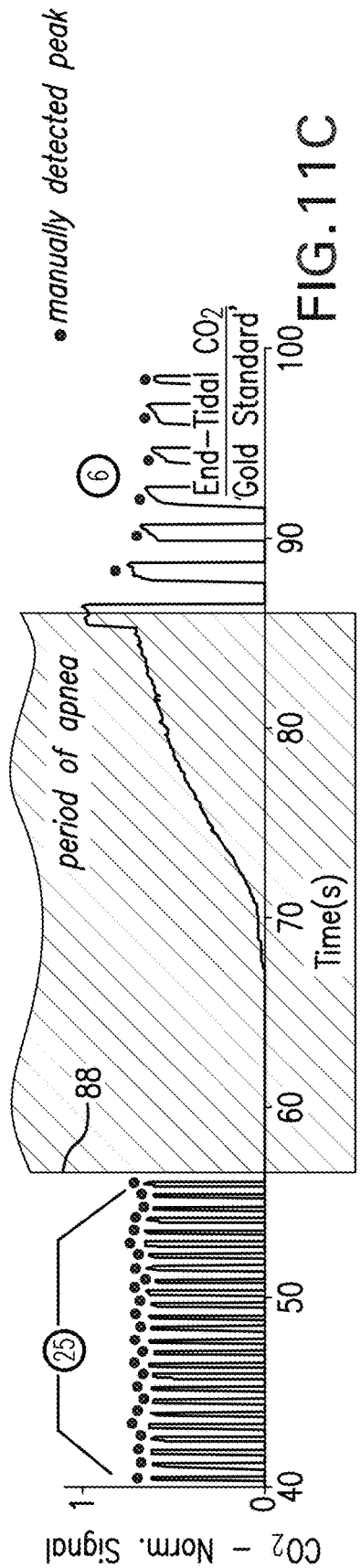

As shown in FIGS. 10-11, agreement between RR calculated from ACC, IP, and et-CO2 waveforms also holds before and after periods of apnea, as indicated by the shaded region 31 in FIGS. 10A-10C (lasting about 10 seconds), and region 32 in FIGS. 11A-11C (lasting about 30 seconds). As shown in FIGS. 10A-10C, for example, the patient exhibited slow, deep breaths before the period of apnea 31, and fast, deep breaths afterwards. FIGS. 11A-11C show an opposing configuration. Here, the patient exhibited fast, shallow breaths before the period of apnea, and slow, shallow breaths afterwards. In both cases agreement between RR calculated from the three unique waveforms was maintained. These data, as described in more detail below, indicate that an adaptive filtering approach utilizing both ACC and IP waveforms can be used to predict a RR that correlates well to that measured with a gold standard, such as et-CO2.

Figure 12A:
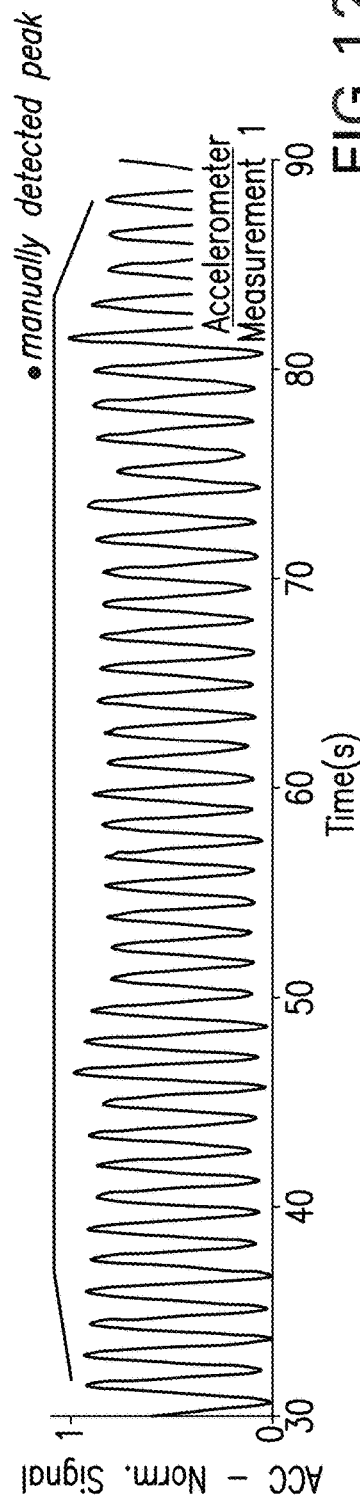
FIGS. 12A-C show an ACC waveform filtered with a 0.01→0.1 Hz bandpass filter (FIG. 12A; top), an IP waveform (FIG. 12B), and a et-CO2 waveform (FIG. 12C; bottom) simultaneously measured from a walking patient undergoing fast, deep breaths.
Figure 12B:
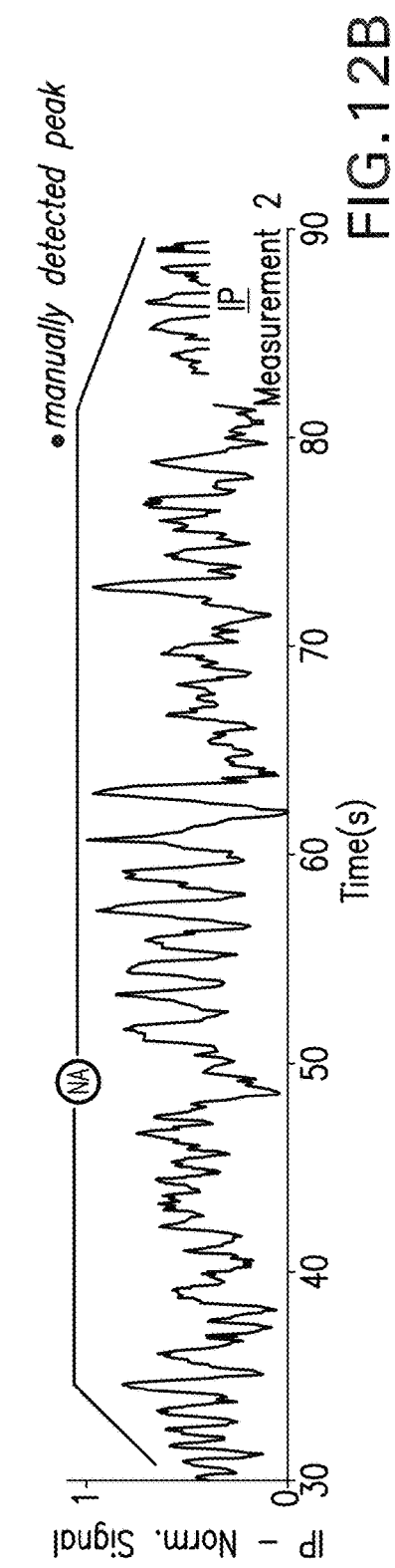
Figure 12C:
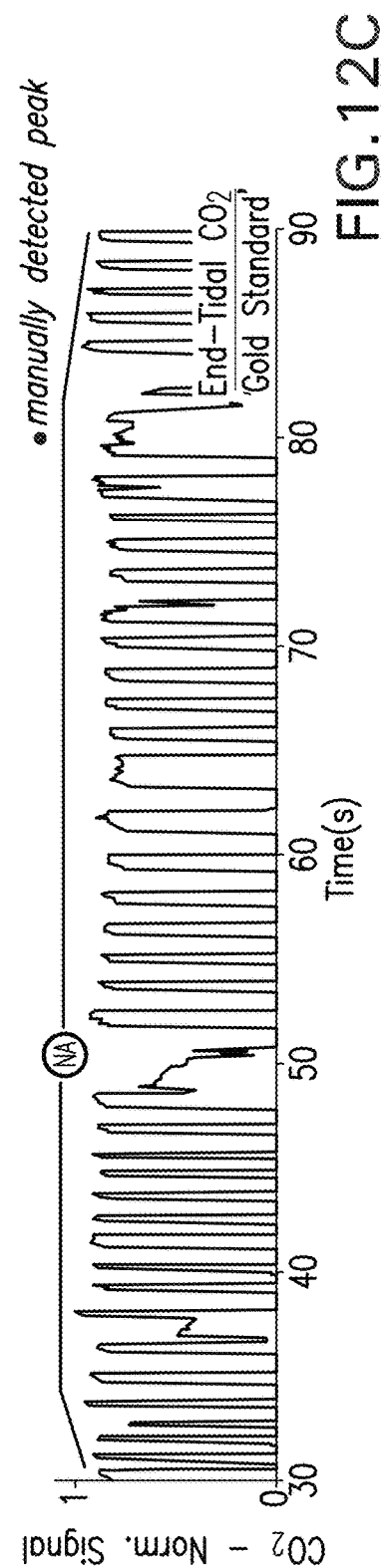

One confounding situation occurs when the patient is walking, as shown in FIGS. 12A-C. Here, in the ACC waveform, signals corresponding to the walking motion overwhelm those corresponding to breathing, making it impossible to selectively determine RR. However, the walking motion results in a well-defined, periodic signal characterized by a very high signal-to-noise ratio. The IP signal, in contrast, is completely corrupted by random noise, presumably caused by a combination of movements associated with the electrodes and their wires, electrical noise due to motion of the underlying muscles, and general corruption of the underlying capacitance in the patient's torso. This makes it impossible to determine RR or any other mechanical/physiological state corresponding to the patient. In this case RR determined from the et-CO2 waveform is somewhat noisy, but still discernible.

While impossible to determine RR from the ACC and IP waveforms shown in FIG. 12A-B, the ACC waveform can be analyzed to determine walking, which it turn may be processed to avoid triggering a false alarm/alert that would normally be generated with a conventional vital sign monitor from the IP waveform, alone. For example, the ACC waveform shown in FIG. 12A, particularly when coupled with ACC waveforms corresponding to other axes of the chest-worn accelerometer as well as those from other accelerometers in the body-worn monitor, shows a clear signal indicative of walking. This determination can be corroborated with the IP waveform, which for a walking patient features an uncharacteristically low signal-to-noise ratio. Based on these signal inputs, an algorithm can determine that the patient is indeed walking, and can assume that their RR value is within normal limits, as a patient undergoing a consistent walking pattern is likely not in dire need of medical attention. For this reason an alarm/alert associated with RR is not generated. Similar alarms can be avoided when processing of the ACC waveforms determines that the patient is convulsing or falling (see, e.g., FIGS. 21-24), although in these cases a different type of alarm/alert may sound. In this way, collective processing of both the ACC and IP waveforms can help reduce false alarms/alerts associated with RR, while improving real alarms/alerts corresponding to other patient situations.

Adaptive Filtering

Figure 13:
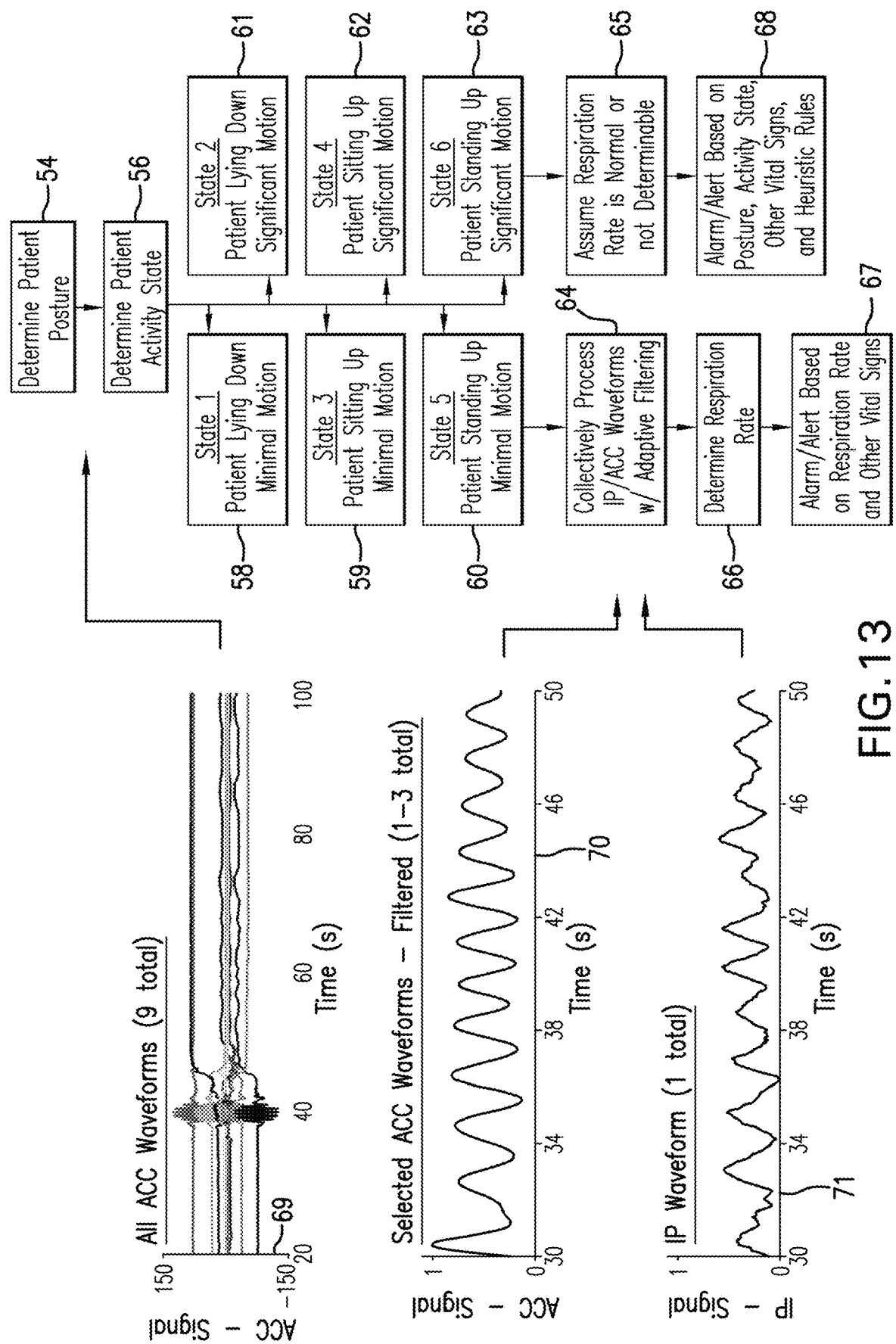
FIG. 13 shows a flow chart along with ACC and IP waveforms used to determine RR using an adaptive filtering technique.

FIG. 13 illustrates in more detail how ACC and IP waveforms can be collectively processed to determine RR, activity levels, posture, and alarms/alerts associated with these patient states. The figure shows a flow chart describing an algorithm that would typically run using a microprocessor, such as that contained within a wrist-worn transceiver such as that shown in FIG. 28. Alternatively, the algorithm could run on a microprocessor mounted on the patient's torso with the IP and accelerometer sensors or elsewhere. The algorithm begins with steps 54, 56 that process all nine ACC waveforms, which are shown in the graph 69 on the left-hand side of the figure, to determine the patient's posture (step 54) and activity level (step 56). Both these processes are described in detail below. In general, determining posture (step 54) involves processing DC values of the ACC waveform generated by the accelerometer mounted on the patient's chest; such signals are shown in the initial and end portions of the graph 69, which show changing DC values representing a posture change. Once sampled, the DC values are processed with an algorithm to estimate states corresponding to the patient such as standing, sitting, prone, supine, and lying on their side. This algorithm is also described with reference to FIG. 26A, 26B, below.

Once posture is determined, the algorithm then analyzes AC portions of the ACC waveforms to determine the patient's activity level (step 56). This part of the algorithm, which is also described in detail below, can be performed in several ways. For example, the AC portions of the ACC waveforms, such as the oscillating portion in the graph 69, can be processed with a Fourier Transform-based analysis to determine a frequency-dependent power-spectrum. Specific activity levels, such as walking and convulsing, involve periodic or quasi-periodic motions; these result in a well-defined power spectrum with frequency components between about 0 and 15 Hz (with this value representing the upper limit of human motion). Frequency bands in the power spectrum can be analyzed to estimate the patient's activity level. This analysis can also be combined with the posture determination from step 54 to refine the calculation for activity level. For example, a patient that is sitting down may be convulsing, but cannot be walking. Similarly, a falling event will begin with a standing posture, and end with a prone or supine posture.

Alternatively, the patient's activity level may be estimated with an algorithm based on probability and the concept of a 'logit variable', which considers a variety of time and frequency-domain parameters extracted from the AC portions of the ACC waveforms, and then processes these with a probability analysis that considers activity levels from a previously measured group of patients. An analysis based on a series of 'decision trees' can also be used to estimate the patient's activity level. Here, the decision trees feature steps that process both the AC and DC portions of the ACC waveforms to estimate the patient's activity level.

Algorithms that describe the patient's posture and activity level are described in detail in the following co-pending patent applications, the contents of which are incorporated herein by reference: VITAL SIGN MONITOR FEATURING 3 ACCELEROMETERS (U.S. Ser. No. 12/469,094; filed May 20, 2009) and METHOD FOR GENERATING ALARMS/ALERTS BASED ON A PATIENT'S POSTURE AND VITAL SIGNS (U.S. Ser. No. 12/469,236; filed May 20, 2009).

The patient's overall state is preferably grouped into one of two categories once posture and activity level are determined with steps 54 and 56. The first group involves relatively motion-free states, and includes categories such as patients that are: lying down with minimal motion (step 58), sitting up with minimal motion (step 59), and standing upright with minimal motion (step 60). Adaptive filtering that processes both ACC and IP waveforms will be effective in determining RR from this group of patients. The second group features patients that are undergoing some type of motion that will likely influence both the ACC and IP waveforms. Categories for this group include patients that are: lying down with significant motion, e.g. convulsing or talking in an animated manner (step 61), sitting up with significant motion (step 62), or standing upright with significant motion, e.g. walking (step 63). Here, the adaptive filtering approach is abandoned, as a pair of respiratory-influenced waveforms with high signal-to-noise ratios is not available. Instead, the second group of patients is processed with a series of heuristic rules, described above, to determine whether or not to generate an alarm/alert based on their posture, activity level, and vital signs (including RR).

Patients within the first group (steps 58, 59, 60) yield ACC and IP waveforms that are collectively processed with an algorithm based on adaptive filtering to determine RR. Representative waveforms are described above and are shown, for example, by graphs 70, 71, as well as those shown in FIGS. 4-11. Details of the adaptive filtering algorithm are described below with reference to FIG. 14. This technique yields an accurate value for RR (step 66). An alarm/alert is generated if this value exceeds pre-set high and low limits for RR for a well-defined period of time (step 67).

For the second group of patients undergoing motion (steps 61, 62, 63) it is assumed that RR is normal but cannot be accurately determined (step 65). The underlying theory is that a patient that is walking or talking likely has a normal RR, and that such activity levels may result in artificially high or low values of RR that may trigger a false alarm. Still, an alarm/alert may be generated depending on the patient's posture or activity level, coupled with other vital signs and a set of heuristic rules (step 68). For example, activity levels such as convulsing or falling will automatically generate an alarm/alert. In another example, during step 68 the algorithm may ignore vital signs that are known to be strongly affected by motion (e.g. RR, blood pressure, and SpO2), and process only those that are relatively immune to motion (e.g. heart rate and temperature). An alarm/alert may be triggered based on these parameters and the patient's motion and activity level. The set of heuristic rules used during step 68, along with a general approach for generating alarms/alerts with the body-worn monitor described herein, are described in more detail in the following co-pending patent application, the contents of which have been fully incorporated by reference above: METHOD FOR GENERATING ALARMS/ALERTS BASED ON A PATIENT'S POSTURE AND VITAL SIGNS (U.S. Ser. No. 12/469,236; filed May 20, 2009).

Figure 14:
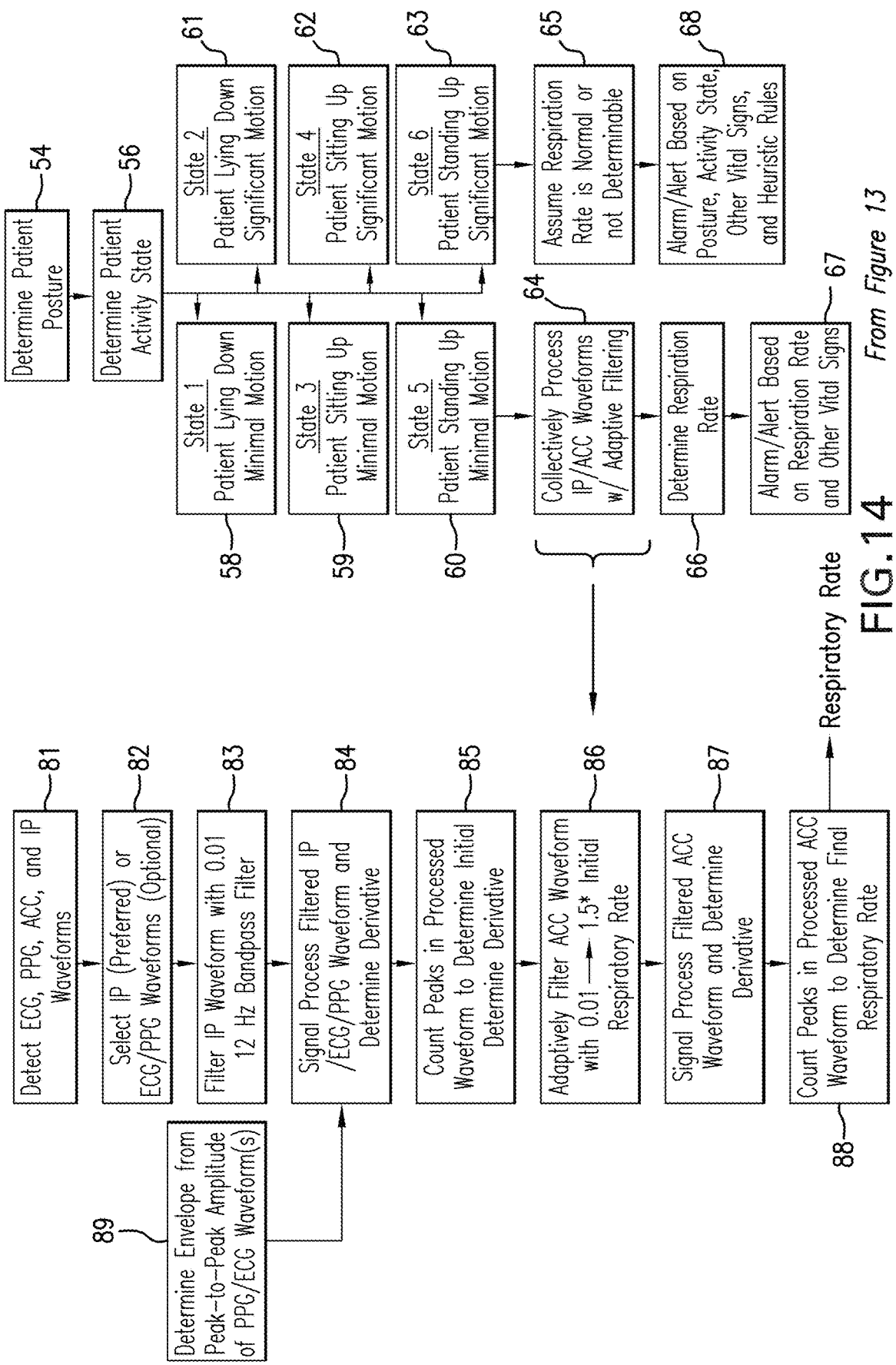
FIG. 14 shows a flow chart that describes details of the adaptive filtering technique shown in FIG. 13.

FIG. 14 describes in more detail an exemplary adaptive filtering algorithm used during step 64 to determine RR from the IP and ACC waveforms. The algorithm involves collecting ECG, PPG, ACC, and IP waveforms using the body-worn monitor described in FIGS. 27A, B (step 81). ECG and PPG waveforms are processed with external algorithms to determine heart rate, blood pressure, and pulse oximetry, as described in more detail below. Additionally, as described with reference to FIGS. 20A-E, these waveforms feature envelopes that are modulated by respiratory rate, and thus may be analyzed to provide an initial RR value for the adaptive filtering algorithm. Once collected, the ECG, PPG, and IP waveforms are analyzed with a series of simple metrics, such as analysis of signal-to-noise ratios and comparison of extracted RR values to pre-determined limits, to determine which one will provide the initial input to the adaptive filtering algorithm (step 82). Ideally RR is extracted from the IP waveform, as this provides a reliable initial value. If during step 82 it is determined that IP does not yield a reliable initial RR value, the envelopes of both the PPG and ECG waveforms are extracted and analyzed as described above. If they are acceptable, RR values are then extracted from these waveforms and used for the initial value (step 89). The algorithm is terminated if each of the IP, PPG, and ECG waveforms fails to yield a reliable RR value.

If the IP waveform is deemed suitable, it is filtered with a finite impulse response filter with a bandpass of 0.01→12 Hz to remove electrical and mechanical noise that may lead to artifacts (step 83). Once filtered, the waveform is derivatized to yield a waveform similar to that shown in FIG. 3H (step 84), and then analyzed to find a zero-point crossing so that peaks corresponding to RR can be counted (step 85). During step 85 several simple signal processing algorithms may also be deployed to avoid counting features that don't actually correspond to RR, such as those shown in FIGS. 3F, 3G. For example, prior to looking for the zero-point crossing, the derivatized waveform may be squared to accentuate lobes on each side of the crossing. The resultant waveform may then be filtered again with a bandpass filter, or simply smoothed with a moving average. In other embodiments only lobes that exceed a pre-determined magnitude are considered when determining the zero-point crossing.

Once determined during step 85, the initial RR serves as the basis for the adaptive filter used in step 85. Typically this rate is multiplied by a factor (e.g. 1.5), and then used as an upper limit for a bandpass filter based on a finite impulse response function used to filter the ACC waveform (step 86). The lower limit for the bandpass filter is typically 0.01 Hz, as described above. Filtering the ACC waveform with these tailored parameters yields a resulting waveform that has a high signal-to-noise ratio, limited extraneous frequency components, and can easily be processed to determine RR. During step 87 signal processing technique similar to those described above with reference to step 84 may be used to further process the ACC waveform. These yield a smooth, derivatized waveform that is analyzed to determine a zero-point crossing and count the resulting peaks contributing to RR (step 88).

FIGS. 15, 16, and 17 illustrate how the above-described adaptive filtering algorithm can be applied to both ACC and IP waveforms. In each of the figures, the graphs show the ACC waveform filtered with an initial, non-adaptive filter (15A, 16A, 17A; 0.01→2 Hz bandpass), and the IP waveform filtered under similar conditions with a slightly larger bandpass filter (15B, 16B, 17B; 0.01→12 Hz bandpass). Typically the IP waveform is filtered with the larger bandpass so that high-frequency components composing the rising and falling edges of pulses within these waveforms are preserved.

Once filtered, the IP waveform is processed as described above to determine an initial RR. This value may include artifacts due to motion, electrical, and mechanical noise that erroneously increases or decreases the initial RR value. But typically such errors have little impact on the final RR value that results from the adaptive filter. The middle graph (FIGS. 15C, 16C, and 17C) in each figure show the ACC waveform processed with the adaptive filter. In all cases this waveform features an improved signal-to-noise ratio compared to data shown in the top graph (15A, 16A, 17A), which is processed with a non-adaptive (and relatively wide) filter. Typically the narrow bandpass on the adaptive filter removes many high-frequency components that contribute the sharp rising and falling edges of pulses in the ACC waveforms. This slightly distorts the waveforms by rounding the pulses, giving the filtered waveform a shape that resembles a conventional sinusoid. Such distortion, however, has basically no affect on the absolute number of pulses in each waveform which are counted to determine RR.

Figure 15F:
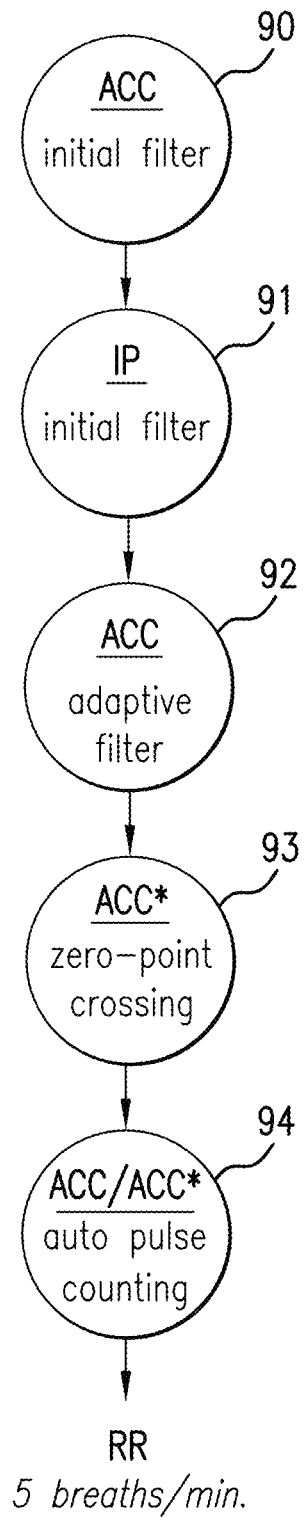
FIG. 15F is a flow chart showing the algorithmic steps used to process the waveforms shown in FIGS. 15A-E.
Figure 16A:
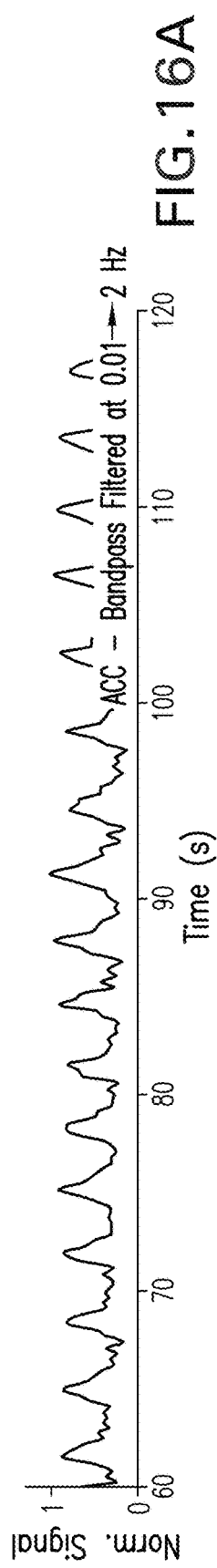
FIGS. 16A-E show graphs of an ACC waveform filtered initially with a 0.01→2 Hz bandpass filter (FIG. 16A; top), an IP waveform filtered initially with a 0.01→12 Hz bandpass (FIG. 16B), an ACC waveform adaptively filtered with a bandpass filter ranging from 0.01 Hz to 1.5 times the breathing rate calculated from the IP waveform in FIG. 16B (FIG. 16C), a first derivative of the filtered waveform in FIG. 16C (FIG. 16D), and the adaptively filtered waveform in FIG. 16C along with markers (FIG. 16E; bottom) indicating fast, deep breaths as determined from the algorithm shown by the flow chart in FIG. 14.
Figure 16B:
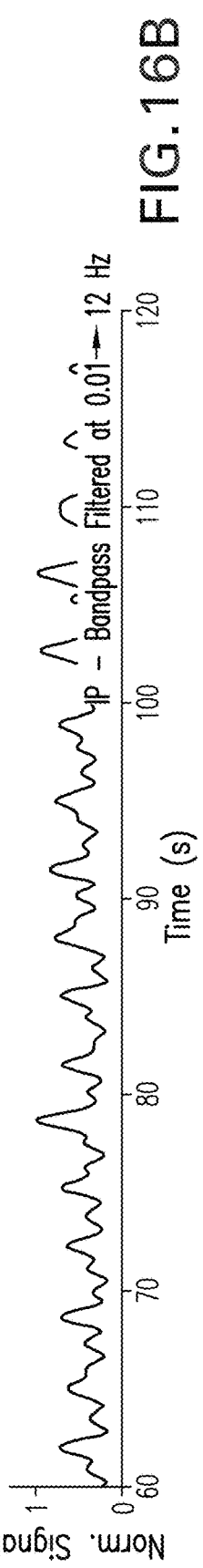
Figure 16C:
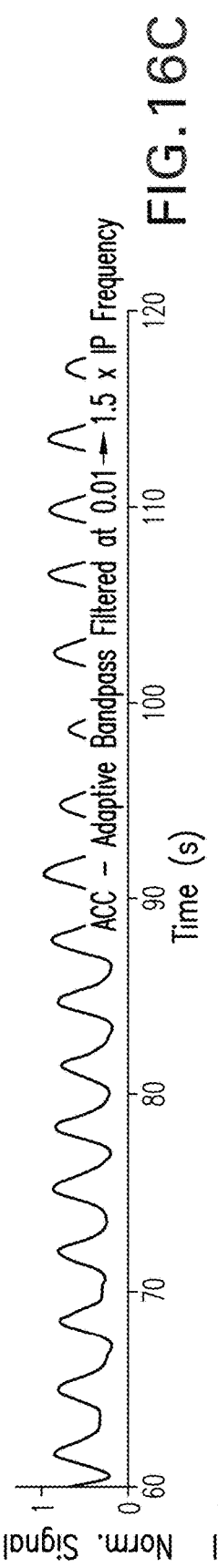
Figure 16D:
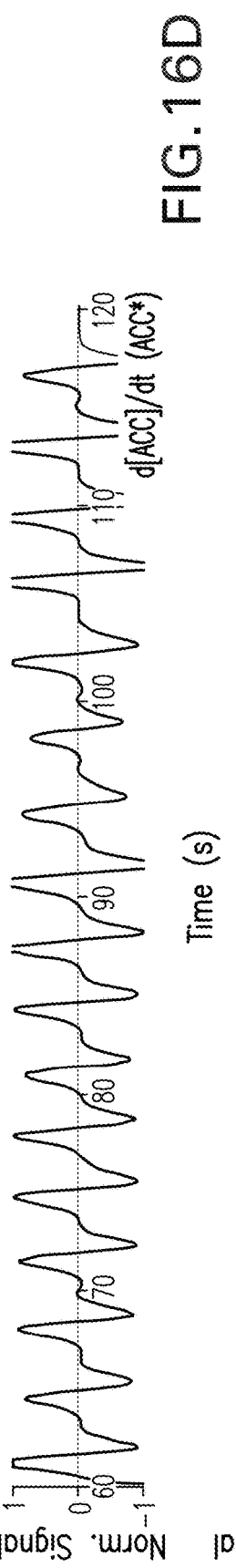
Figure 16E:
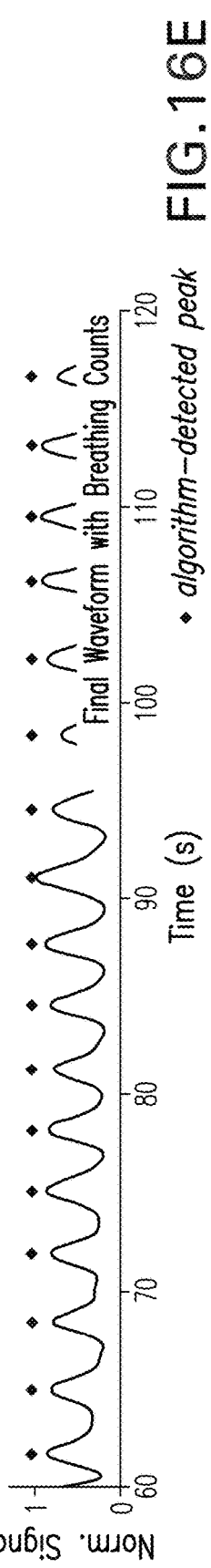
Figure 16F:
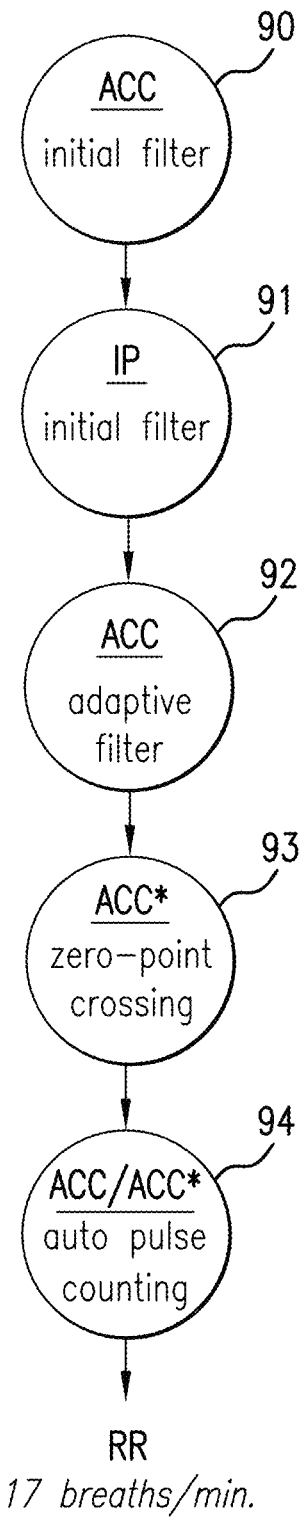
FIG. 16F is a flow chart showing the algorithmic steps used to process the waveforms shown in FIGS. 16A-E.
Figure 17A:
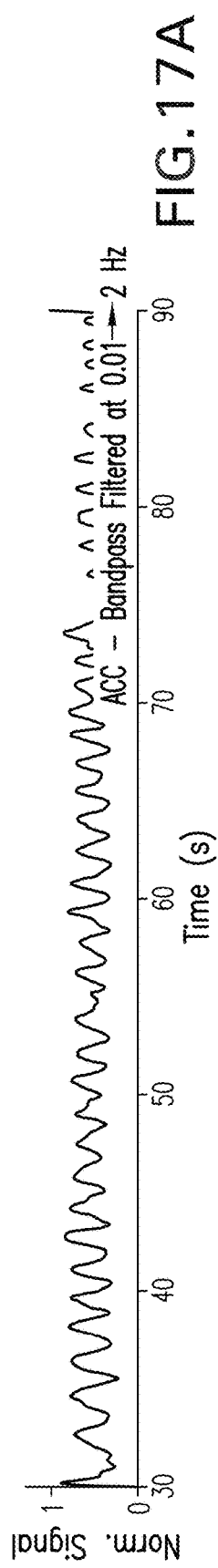
FIGS. 17A-E show graphs of an ACC waveform filtered initially with a 0.01→2 Hz bandpass filter (FIG. 17A; top), an IP waveform filtered initially with a 0.01→12 Hz bandpass (FIG. 17B), an ACC waveform adaptively filtered with a bandpass filter ranging from 0.01 Hz to 1.5 times the breathing rate calculated from the IP waveform in FIG. 17B (FIG. 17C), a first derivative of the filtered waveform in FIG. 17C (FIG. 17D), and the adaptively filtered waveform in FIG. 17C along with markers (FIG. 17E; bottom) indicating very fast, deep breaths as determined from the algorithm shown by the flow chart in FIG. 14.
Figure 17B:
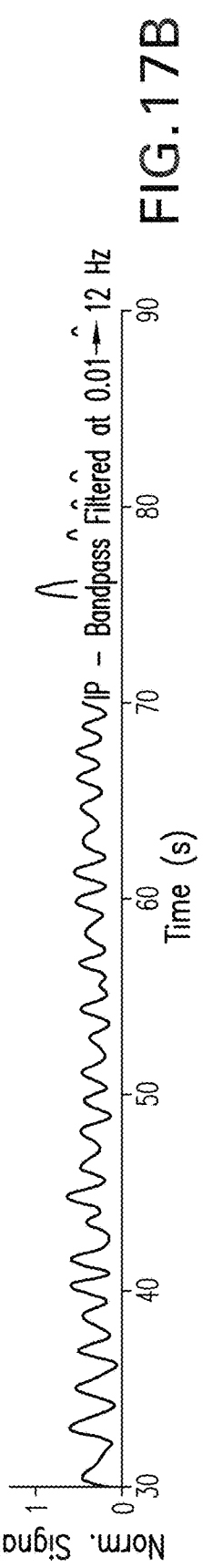
Figure 17C:
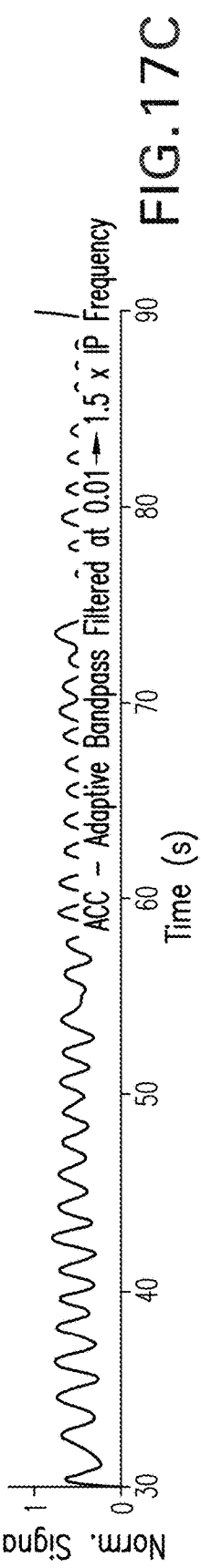
Figure 17D:
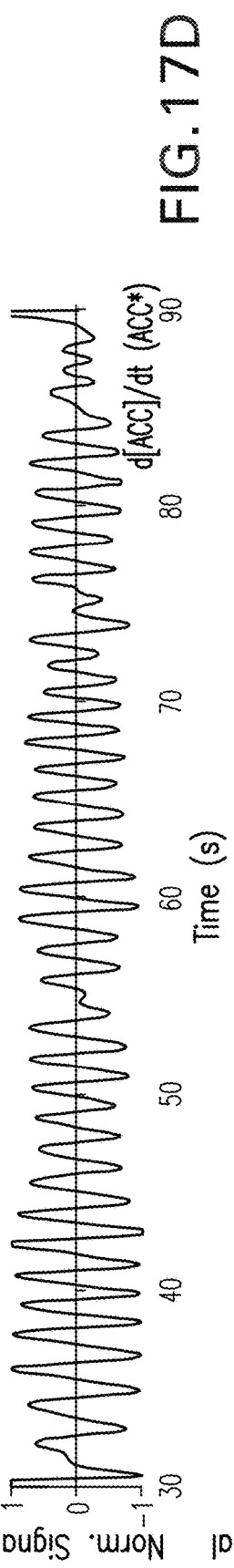
Figure 17E:
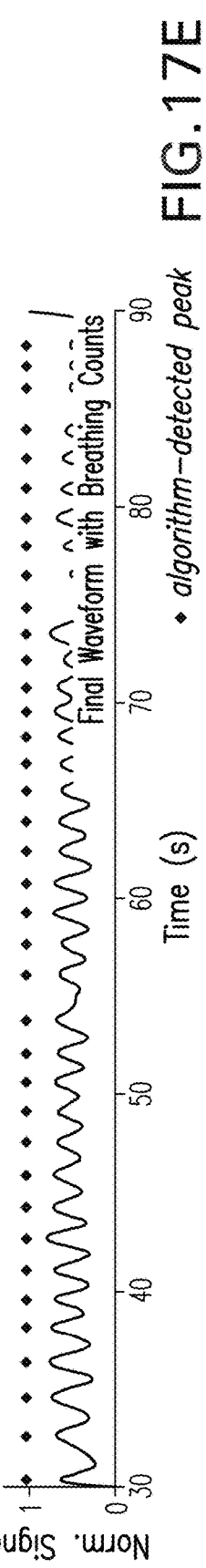
Figure 17F:
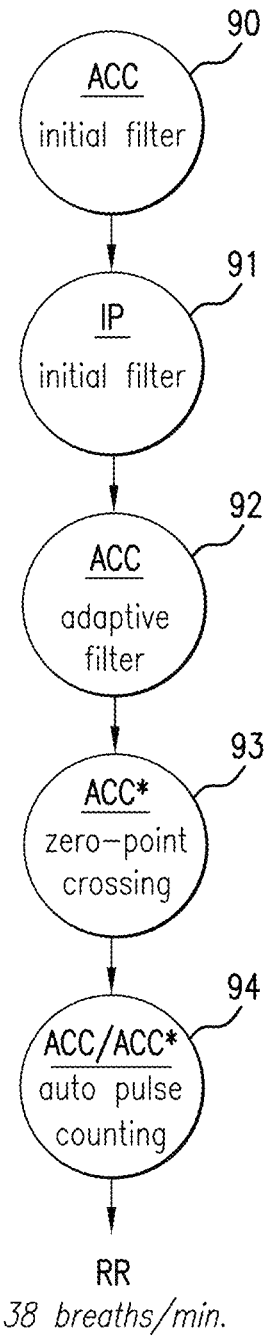
FIG. 17F is a flow chart showing the algorithmic steps used to process the waveforms shown in FIGS. 17A-E.

The adaptively filtered waveform is then derivatized and graphed in FIGS. 15D, 16D, and 17D. This waveform is then processed with the above-mentioned signal processing techniques, e.g. squaring the derivative and filtering out lobes that fall beneath pre-determined threshold values, to yield an algorithm-determined 'count', indicated in FIGS. 15E, 16E, and 17E as a series of black triangles. The count is plotted along with the adaptively filtered waveforms from FIGS. 15C, 16C, and 17C. Exact overlap between each pulse in the waveform and the corresponding count indicates the algorithm is working properly. Data from each of the figures correspond to varying respiratory behavior (5, 17, and 38 breaths/minute in, respectively, FIGS. 15, 16, and 17), and indicate that this technique is effective over a wide range of breathing frequencies. The right-hand side of the figures (FIGS. 15F, 16F, and 17F) show a series of steps 90-94 that indicate the analysis required to generate the corresponding graphs in the figure.

FIG. 18 shows data collected when the patient is walking. Here, the walking motion manifests in the ACC waveform in FIG. 18A as a series of periodic pulses which look similar to RR, particularly after the initial bandpass filter of 0.01→2 Hz. However, the IP waveform shown in FIG. 18B has a poor signal-to-noise ratio, and fails to yield an accurate initial value for RR. This is indicated by step 95 in the modified flow chart shown in FIG. 18C, which highlights an alternate series of steps that are deployed when motion is present. As shown in step 96, in this case other ACC waveforms (e.g., those along the x and y-axes, indicated by ACC') are analyzed to determine that the patient is walking. In this case no value of RR is reported, and an alarm/alert is not triggered because of the above-mentioned heuristic rules (i.e. a walking patient typically has a normal RR, and is not in need of medical attention).

Figure 19:
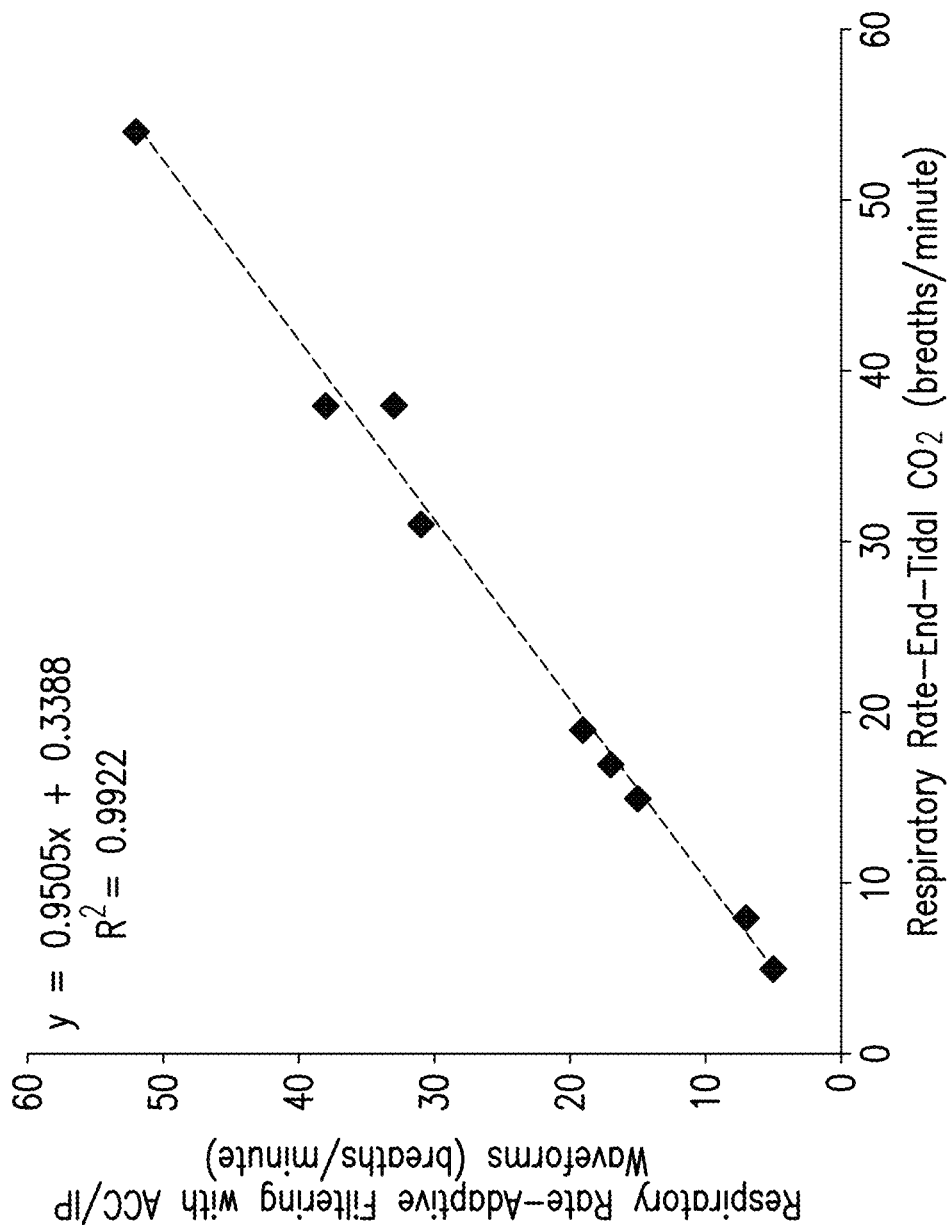
FIG. 19 is a graph showing correlation between respiratory rates measured with the adaptive filtering technique shown by the flow chart in FIG. 14 and et-CO2.

The efficacy of using adaptive filtering to determine RR from ACC and IP waveforms is summarized with the correlation graph in FIG. 19. The graph shows correlation with et-CO2, which in this case represents a gold standard. Correlation is strong ($r^2=0.99$ for a RR range of 5-54 breaths/minute), and the graph includes data collected from patients in a range of postures (standing upright, lying down) and undergoing a range of breathing behaviors (deep breaths, shallow breaths). Bias calculated from these data was 0.8 breaths/minute, and the standard deviation of the differences was 1.6 breaths/minute. These statistics indicate adaptive filtering yields RR with an accuracy that is within the FDA's standards of +/−2 breaths/minute over a range of 0-70 breaths/minute.

Determining Respiratory Rate from ECG and PPG Waveforms

As described above, RR can additionally be determined from both the PPG and ECG waveforms by analyzing an envelope outlining heartbeat-induced pulses in these waveforms. Both PPG and ECG waveforms are collected with the body-worn monitor of FIGS. 27A, 27B, where they are further analyzed to continuously determine cNIBP according to the Composite Technique, as described above. FIGS. 20A-E show representative data that indicate this technique. FIG. 20A, for example, shows an unfiltered ECG waveform featuring a train of pulses, each representing an individual QRS complex. The envelope of the QRS complexes is extracted by determining the maximum and minimum of each complex. Alternatively it can be determined with a series of digital filters that only pass very low frequencies. Comparison of the ECG envelope in FIG. 20B with the IP waveform in FIG. 20E indicates good agreement between these two approaches. Similarly, the PPG waveform shown in FIG. 20C features a train of pulses, each corresponding to a unique heartbeat, that typically follow the ECG QRS complex by a few hundred milliseconds. It is this time difference (typically called a 'pulse transit time', or PTT) that is sensitive to blood pressure changes, and is used during the Composite Technique to measure an absolute value for blood pressure. The PPG envelope, like the ECG envelope, is modulated by RR, and can be determined by extracting the maximum and minimum of each pulse. Alternatively this envelope can be determined with a low-pass filter similar to that used to extract the ECG envelope. As shown in FIG. 20D, the resulting envelope agrees well with the IP waveform, indicating it too is indicative of RR.

Figure 27B:
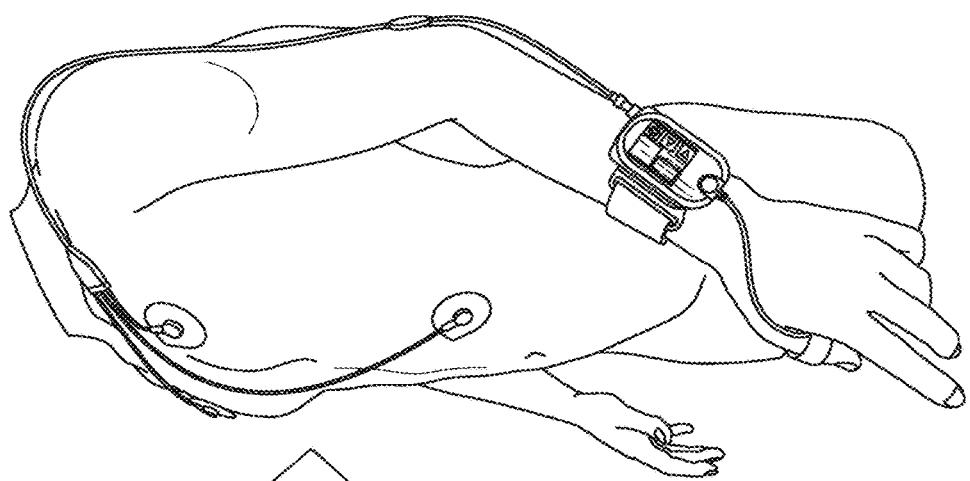
FIGS. 27A and 27B show, respectively, a three-dimensional image of the body-worn monitor of the invention attached to a patient during and after an initial indexing measurement.
Figure 27A:
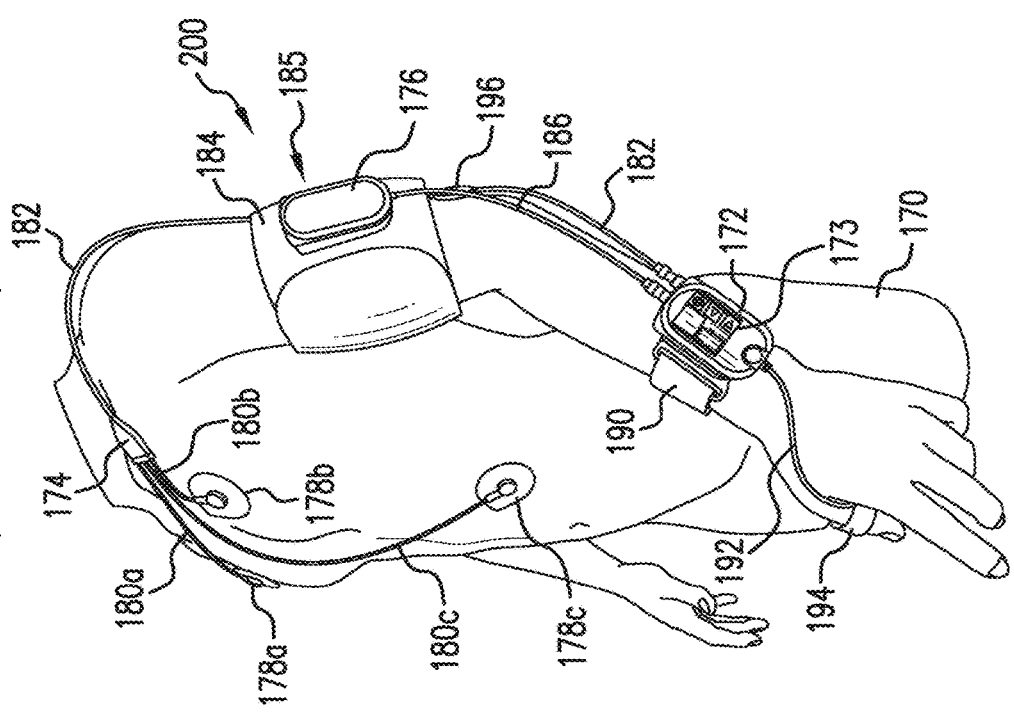

The body-worn monitor shown in FIGS. 27A, 27B measures two separate PPG waveforms (generated with red and infrared radiation) to determine the patient's SpO2 value. The algorithm for this calculation is described in detail in the following co-pending patent applications, the contents of which are incorporated herein by reference: BODY-WORN PULSE OXIMETER (U.S. Ser. No. 61/218,062; filed Jun. 17, 2009). In embodiments, envelopes from both PPG waveforms can be extracted and processed to determine an initial value of RR. This value may also be calculated from the ECG waveform alone, or from this waveform and one or both PPG waveforms. As described above, this method for determining an initial RR value for the adaptive filter algorithm is less preferred than one that uses an IP waveform. Such an algorithm would be used, for example, if an IP waveform featuring a good signal-to-noise ratio was not available.

Affect of Motion on ECG, PPG, and ACC Waveforms

A patient's activity level, as characterized by ACC waveforms, can have a significant impact on the PPG and ECG waveforms used to measure RR and cNIBP. For example, FIGS. 21-24 show time-dependent graphs of ECG, PPG, and ACC waveforms for a patient who is resting (FIG. 21), walking (FIG. 22), convulsing (FIG. 23), and falling (FIG. 24). Each graph includes a single ECG waveform, PPG waveform and three ACC waveforms. In all cases the PPG waveforms are generated with the infrared light source. The ACC waveforms correspond to signals measured along the x, y, and z axes by a single accelerometer worn on the patient's wrist, similar to the accelerometer used within the wrist-worn transceiver shown in FIG. 28.

The figures indicate that time-dependent properties of both ECG and PPG waveforms can be strongly affected by certain patient activities, which are indicated by the ACC waveforms. Accuracy of RR and cNIBP calculated from these waveforms is therefore affected as well. FIGS. 21A-C, for example, shows data collected from a patient at rest. This state is clearly indicated by the ACC waveforms (FIG. 21C; bottom), which feature a relatively stable baseline along all three axes of the accelerometer. High-frequency noise in all the ACC waveforms shown in FIGS. 21-24 is due to electrical noise, and is not indicative of patient motion in any way. The ECG (FIG. 21A; top) and PPG (FIG. 21B; middle) waveforms for this patient are correspondingly stable, thus allowing algorithms operating on the body-worn monitor to accurately determine SpO2 (from the PPG waveform), along with heart rate and respiratory rate (from the ECG waveform), cNIBP (from a PTT extracted from both the ECG and PPG waveforms). Based on the data shown in FIG. 21, algorithms operating on the body-worn monitor assume that vital signs calculated from a resting patient are relatively stable; the algorithm therefore deploys normal threshold criteria for alarms/alerts, described below in Table 1, for patients in this state.

The ECG and PPG waveforms shown, respectively, in FIGS. 21A and 21B also feature envelopes indicated by the dashed lines 97a, 97b, 98 that are modulated by RR. This modulation is similar to that shown in FIGS. 20A and 20C.

FIGS. 22A-C shows ECG (FIG. 22A; top), PPG (FIG. 22B; middle), and ACC (FIG. 22C; top) waveforms measured from a walking patient wearing the body-worn monitor. In this case, the ACC waveform clearly indicates a quasi-periodic modulation, with each 'bump' in the modulation corresponding to a particular step. The 'gaps' in the modulation, shown near 10, 19, 27, and 35 seconds, correspond to periods when the patient stops walking and changes direction. Each bump in the ACC waveform includes relatively high-frequency features (other than those associated with electrical noise, described above) that correspond to walking-related movements of the patient's wrist.

The ECG waveform measured from the walking patient is relatively unaffected by motion, other than indicating an increase in heart rate (i.e., a shorter time separation between neighboring QRS complexes) and respiratory rate (i.e. a higher frequency modulation of the waveform's envelope) caused by the patient's exertion. The PPG waveform, in contrast, is strongly affected by this motion, and pulses within it become basically immeasurable. Its distortion is likely due in part to a quasi-periodic change in light levels, caused by the patient's swinging arm, and detected by the photodetector within the thumb-worn sensor. Movement of the patient's arm additionally affects blood flow in the thumb and can cause the optical sensor to move relative to the patient's skin. The photodetector measures all of these artifacts, along with a conventional PPG signal (like the one shown in FIG. 21B) caused by volumetric expansion in the underlying arteries and capillaries within the patient's thumb. The artifacts produce radiation-induced photocurrent that is difficult to distinguish from normal PPG signal used to calculate SpO2 and cNIBP. These vital signs are thus difficult or impossible to accurately measure when the patient is walking.

The body-worn monitor may deploy multiple strategies to avoid generating false alarms/alerts during a walking activity state that correspond to RR as well as all other vital signs. As described in detail below, the monitor can detect this state by processing the ACC waveforms shown in FIG. 22C along with similar waveforms measured from the patient's bicep and chest. Walking typically elevates heart rate, respiratory rate, and blood pressure, and thus alarm thresholds for these parameters, as indicated by Table 1, are systematically and temporarily increased when this state is detected. Values above the modified thresholds are considered abnormal, and trigger an alarm. SpO2, unlike heart rate, respiratory rate and blood pressure, does not typically increase with exertion. Thus the alarm thresholds for this parameter, as shown in Table 1, do not change when the patient is walking. Body temperature measured with the body-worn monitor typically increases between 1-5%, depending on the physical condition of the patient and the speed at which they are walking.

TABLE 1 motion-dependent alarm/alert thresholds and heuristic rules for a walking patient

| Vital Sign | Motion State | Modified Threshold for Alarms/Alerts | Heuristic Rules for Alarms/Alerts |
|---|---|---|---|
| Blood Pressure (SYS, DIA) | Walking | Increase (+10-30%) | Ignore Threshold; Do Not Alarm/Alert |
| Heart Rate | Walking | Increase (+10-300%) | Use Modified Threshold; Alarm/Alert if Value Exceeds Threshold |
| Respiratory Rate | Walking | Increase (+10-300%) | Ignore Threshold; Do Not Alarm/Alert |
| SpO2 | Walking | No Change | Ignore Threshold; Do Not Alarm/Alert |
| Temperature | Walking | Increase (+10-30%) | Use Original Threshold; Alarm/Alert if Value Exceeds Threshold |

To further reduce false alarms/alerts, software associated with the body-worn monitor or remote monitor can deploy a series of heuristic rules determined beforehand using practical, empirical studies. These rules, for example, can indicate that a walking patient is likely healthy, breathing, and characterized by a normal RR. Accordingly, the rules dictate that cNIBP, RR, and SpO2 values measured during a walking state that exceed predetermined alarm/alert thresholds are likely corrupted by artifacts; the system, in turn, does not sound the alarm/alert in this case. Heart rate, as indicated by FIG. 22A, and body temperature can typically be accurately measured even when a patient is walking; the heuristic rules therefore dictate the modified thresholds listed in Table 1 be used to generate alarms/alerts for a patient in this state.

Additionally, despite the patient's walking motion, the ECG waveform shown in FIG. 22A still features an envelope shown by the dashed lines 99a, 99b that represents the patient's RR. This indicates that RR may be determined from a walking patient by processing the ECG envelope, even when other signals (e.g. IP and ACC waveforms) are corrupted. Because of the motion-induced noise in these signals, RR is typically determined directly from the ECG envelope, without using any adaptive filtering.

FIGS. 23A-C show ECG (FIG. 23A; top), PPG (FIG. 23B; middle), and ACC (FIG. 23C; bottom) waveforms measured from a patient that is simulating convulsing by rapidly moving their arm back and forth. A patient undergoing a Gran-mal seizure, for example, would exhibit this type of motion. As is clear from the waveforms, the patient is at rest for the initial 10 seconds shown in the graph, during which the ECG and PPG waveforms are uncorrupted by motion. The patient then begins a period of simulated, rapid convulsing that lasts for about 12 seconds. A brief 5-second period of rest follows, and then convulsing begins for another 12 seconds or so.

Convulsing modulates the ACC waveform due to rapid motion of the patient's arm, as measured by the wrist-worn accelerometer. This modulation is strongly coupled into the PPG waveform, likely because of the phenomena described above, i.e.: 1) ambient light coupling into the oximetry probe's photodiode; 2) movement of the photodiode relative to the patient's skin; and 3) disrupted blow flow underneath the probe. Note that from about 23-28 seconds the ACC waveform is not modulated, indicating that the patient's arm is at rest. During this period the ambient light is constant and the optical sensor is stationary relative to the patient's skin. But the PPG waveform is still strongly modulated, albeit at a different frequency than the modulation that occurred when the patient's arm was moving, and the pulses therein are difficult to resolve. This indicates that the disrupted blood flow underneath the optical sensor continues even after the patient's arm stops moving. Using this information, both ECG and PPG waveforms similar to those shown in FIG. 23 can be analyzed in conjunction with ACC waveforms measured from groups of stationary and moving patients. These data can then be analyzed to estimate the effects of specific motions and activities on the ECG and PPG waveforms, and then deconvolute these factors using known mathematical techniques to effectively remove any motion-related artifacts. The deconvoluted ECG and PPG waveforms can then be used to calculate vital signs, as described in detail below.

The ECG waveform is modulated by the patient's arm movement, but to a lesser degree than the PPG waveform. In this case, modulation is caused primarily by electrical 'muscle noise' instigated by the convulsion and detected by the ECG electrodes, and well as by convulsion-induced motion in the ECG cables and electrodes relative to the patient's skin. Such motion is expected to have a similar affect on temperature measurements, which are determined by a sensor that also includes a cable.

Table 2, below, shows examples of the modified threshold values and heuristic rules for alarms/alerts generated by a convulsing patient. In general, when a patient experiences convulsions, such as those simulated during the two 12-second periods in FIG. 23, it is virtually impossible to accurately measure any vital signs from the ECG and PPG waveforms. For this reason the threshold values corresponding to each vital sign are not adjusted when convulsions are detected. Heart rate determined from the ECG waveform, for example, is typically erroneously high due to high-frequency convulsions, and RR is immeasurable from the distorted waveform. Strong distortion of the optical waveform also makes both SpO2 and PPT-based cNIBP difficult or impossible to measure. For this reason, algorithms operating on either the body-worn monitor or a remote monitor will not generate alarms/alerts based on vital signs when a patient is convulsing, as these vital signs will almost certainly be corrupted by motion-related artifacts.

TABLE 2 motion-dependent alarm/alert thresholds and heuristic rules for a convulsing patient

| Vital Sign | Motion State | Modified Threshold for Alarms/Alerts | Heuristic Rules for Alarms/Alerts |
| --- | --- | --- | --- |
| Blood Pressure (SYS, DIA) | Convulsing | No Change | Ignore Threshold; Generate Alarm/Alert Because of Convulsion |
| Heart Rate | Convulsing | No Change | Ignore Threshold; Generate Alarm/Alert Because of Convulsion |
| Respiratory Rate | Convulsing | No Change | Ignore Threshold; Generate Alarm/Alert Because of Convulsion |
| SpO2 | Convulsing | No Change | Ignore Threshold; Generate Alarm/Alert Because of Convulsion |

TABLE 2-continued motion-dependent alarm/alert thresholds and heuristic rules for a convulsing patient

| Vital Sign | Motion State | Modified Threshold for Alarms/Alerts | Heuristic Rules for Alarms/Alerts |
| --- | --- | --- | --- |
| Temperature | Convulsing | No Change | Ignore Threshold; Generate Alarm/Alert Because of Convulsion |

Table 2 also shows exemplary heuristic rules for convulsing patients. Here, the overriding rule is that a convulsing patient needs assistance, and thus an alarm/alert for this patient is generated regardless of their vital signs (which, as described above, are likely inaccurate due to motion-related artifacts). The system always generates an alarm/alert for a convulsing patient.

FIGS. 24A-C shows ECG (FIG. 24A; top), PPG (FIG. 24B; middle), and ACC (FIG. 24C; bottom) waveforms measured from a patient that experiences a fall roughly 13 seconds into the measuring period. The ACC waveform clearly indicates the fall with a sharp decrease in its signal, followed by a short-term oscillatory signal, due (literally) to the patient bouncing on the floor. After the fall, ACC waveforms associated with the x, y, and z axes also show a prolonged decrease in value due to the resulting change in the patient's posture. In this case, both the ECG and PPG waveforms are uncorrupted by motion prior to the fall, but basically immeasurable during the fall, which typically takes only 1-2 seconds. Specifically, this activity adds very high frequency noise to the ECG waveform, making it impossible to extract heart rate and RR during this short time period. Falling causes a sharp drop in the PPG waveform, presumably for the same reasons as described above (i.e. changes in ambient light, sensor movement, and disruption of blood flow) for walking and convulsing, making it difficult to measure SpO2 and cNIBP.

After a fall, both the ECG and PPG waveforms are free from artifacts, but both indicate an accelerated heart rate and relatively high heart rate variability for roughly 10 seconds. During this period the PPG waveform also shows distortion and a decrease in pulse amplitude. Without being bound to any theory, the increase in heart rate may be due to the patient's baroreflex, which is the body's haemostatic mechanism for regulating and maintaining blood pressure. The baroreflex, for example, is initiated when a patient begins faint. In this case, the patient's fall may cause a rapid drop in blood pressure, thereby depressing the baroreflex. The body responds by accelerating heart rate (indicated by the ECG waveform) and increasing blood pressure (indicated by a reduction in PTT, as measured from the ECG and PPG waveforms) in order to deliver more blood to the patient's extremities.

Table 3 shows exemplary heuristic rules and modified alarm thresholds for a falling patient. Falling, similar to convulsing, makes it difficult to measure waveforms and the vital signs calculated from them. Because of this and the short time duration associated with a fall, alarms/alerts based on vital signs thresholds are not generated during an actual falls. However, this activity, optionally coupled with prolonged stationary period or convulsion (both determined from the following ACC waveform), generates an alarm/alert according to the heuristic rules.

TABLE 3 motion-dependent alarm/alert thresholds
and heuristic rules for a falling patient
Processing ACC Waveforms to Determine Posture

| Vital Sign | Motion State | Modified Threshold for Alarms/Alerts | Heuristic Rules for Alarms/Alerts |
|---|---|---|---|
| Blood Pressure (SYS, DIA) | Falling | No Change | Ignore Threshold; Generate Alarm/Alert Because of Fall |
| Heart Rate | Falling | No Change | Ignore Threshold; Generate Alarm/Alert Because of Fall |
| Respiratory Rate | Falling | No Change | Ignore Threshold; Generate Alarm/Alert Because of Fall |
| SpO2 | Falling | No Change | Ignore Threshold; Generate Alarm/Alert Because of Fall |
| Temperature | Falling | No Change | Ignore Threshold; Generate Alarm/Alert Because of Fall |

Figure 25:
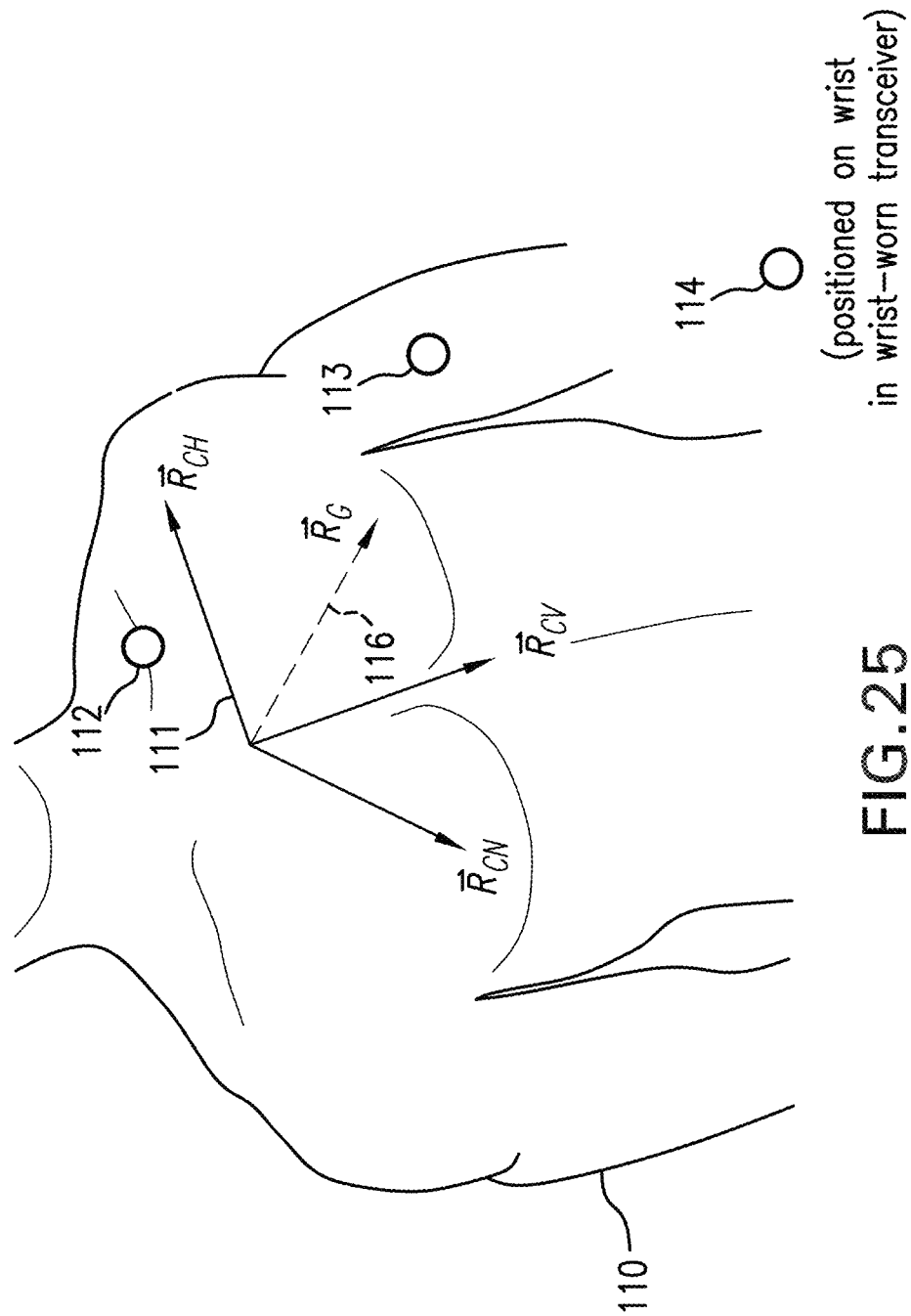
FIG. 25 shows a schematic view of the patient of FIG. 1 and a coordinate axis used with an algorithm and ACC waveforms to determine the patient's posture.

In addition to activity level, as described above and indicated in FIGS. 21-24, a patient's posture can influence how the above-described system generates alarms/alerts from RR, cNIBP, and other vital signs. For example, the alarms/alerts related to both RR and cNIBP may vary depending on whether the patient is lying down or standing up. FIG. 25 indicates how the body-worn monitor can determine motion-related parameters (e.g. degree of motion, posture, and activity level) from a patient 110 using time-dependent ACC waveforms continuously generated from the three accelerometers 112, 113, 114 worn, respectively, on the patient's chest, bicep, and wrist. The height of the patient's arm can affect the cNIBP measurement, as blood pressure can vary significantly due to hydrostatic forces induced by changes in arm height. Moreover, this phenomenon can be detected and exploited to calibrate the cNIBP measurement, as described in detail in the above-referenced patent application, the contents of which have been previously incorporated by reference: BODY-WORN VITAL SIGN MONITOR WITH SYSTEM FOR DETECTING AND ANALYZING MOTION (U.S. Ser. No. 12/469,094; filed May 20, 2009). As described in this document, arm height can be determined using DC signals from the accelerometers 113, 114 disposed, respectively, on the patient's bicep and wrist. Posture, in contrast, can be exclusively determined by the accelerometer 112 worn on the patient's chest. An algorithm operating on the wrist-worn transceiver extracts DC values from waveforms measured from this accelerometer and processes them with an algorithm described below to determine posture.

Specifically, torso posture is determined for a patient 110 using angles determined between the measured gravitational vector and the axes of a torso coordinate space 111. The axes of this space 111 are defined in a three-dimensional Euclidean space where $\vec{R}_{CV}$ is the vertical axis, $\vec{R}_{CV}$ is the horizontal axis, and $\vec{R}_{CN}$ is the normal axis. These axes must be identified relative to a 'chest accelerometer coordinate space' before the patient's posture can be determined.

The first step in determining a patient's posture is to identify alignment of $\vec{R}_{CV}$ in the chest accelerometer coordinate space. This can be determined in either of two approaches. In the first approach, $\vec{R}_{CV}$ is assumed based on a typical alignment of the body-worn monitor relative to the patient. During a manufacturing process, these parameters are then preprogrammed into firmware operating on the wrist-worn transceiver. In this procedure it is assumed that accelerometers within the body-worn monitor are applied to each patient with essentially the same configuration. In the second approach, $\vec{R}_{CV}$ is identified on a patient-specific basis. Here, an algorithm operating on the wrist-worn transceiver prompts the patient (using, e.g., video instruction operating on the wrist-worn transceiver, or audio instructions transmitted through a speaker) to assume a known position with respect to gravity (e.g., standing upright with arms pointed straight down). The algorithm then calculates $\vec{R}_{CV}$ from DC values corresponding to the x, y, and z axes of the chest accelerometer while the patient is in this position. This case, however, still requires knowledge of which arm (left or right) the monitor is worn on, as the chest accelerometer coordinate space can be rotated by 180 degrees depending on this orientation. A medical professional applying the monitor can enter this information using the GUI, described above. This potential for dual-arm attachment requires a set of two pre-determined vertical and normal vectors which are interchangeable depending on the monitor's location. Instead of manually entering this information, the arm on which the monitor is worn can be easily determined following attachment using measured values from the chest accelerometer values, with the assumption that $\vec{R}_{CV}$ is not orthogonal to the gravity vector.

The second step in the procedure is to identify the alignment of $\vec{R}_{CN}$ in the chest accelerometer coordinate space. The monitor determines this vector in the same way it determines $\vec{R}_{CV}$ using one of two approaches. In the first approach the monitor assumes a typical alignment of the chest-worn accelerometer on the patient. In the second approach, the alignment is identified by prompting the patient to assume a known position with respect to gravity. The monitor then calculates $\vec{R}_{CV}$ from the DC values of the time-dependent ACC waveform.

The third step in the procedure is to identify the alignment of $\vec{R}_{CH}$ in the chest accelerometer coordinate space. This vector is typically determined from the vector cross product of $\vec{R}_{CV}$ and $\vec{R}_{CN}$, or it can be assumed based on the typical alignment of the accelerometer on the patient, as described above.

A patient's posture is determined using the coordinate system described above and in FIG. 25, along with a gravitational vector $\vec{R}_G$ that extends normal from the patient's chest. The angle between $\vec{R}_{CV}$ and $\vec{R}_G$ is given by equation (1):

$$\theta_{VG}[n] = \arccos\left(\frac{\vec{R}_G[n] \cdot \vec{R}_{CV}}{\|\vec{R}_G[n]\|\|\vec{R}_{CV}\|}\right) \quad (1)$$

where the dot product of the two vectors is defined as:

$$\vec{R}_G[n] \cdot \vec{R}_{CV} = (y_{Cx}[n] \times r_{CVx}) + (y_{Cy}[n] \times r_{CVy}) + (y_{Cz}[n] \times r_{CVz}) \quad (2)$$

The definition of the norms of $\vec{R}_G$ and $\vec{R}_{CV}$ are given by equations (3) and (4):

$$\|\vec{R}_G[n]\| = \sqrt{(y_{Cx}[n])^2 + (y_{Cy}[n])^2 + (y_{Cz}[n])^2} \quad (3)$$

$$\|\vec{R}_{CV}\| = \sqrt{(r_{CVx})^2 + (r_{CVy})^2 + (r_{CVz})^2}$$

As indicated in equation (5), the monitor compares the vertical angle $\theta_{VG}$ to a threshold angle to determine whether the patient is vertical (i.e. standing upright) or lying down:

if $\theta_{VG} \leq 45°$ then Torso State=0, the patient is upright (5)

If the condition in equation (5) is met the patient is assumed to be upright, and their torso state, which is a numerical value equated to the patient's posture, is equal to 0. The patient is assumed to be lying down if the condition in equation (5) is not met, i.e. $\theta_{VG} > 45$ degrees. Their lying position is then determined from angles separating the two remaining vectors, as defined below.

The angle $\theta_{NG}$ between $\vec{R}_{CN}$ and $\vec{R}_G$ determines if the patient is lying in the supine position (chest up), prone position (chest down), or on their side. Based on either an assumed orientation or a patient-specific calibration procedure, as described above, the alignment of $\vec{R}_{CN}$ is given by equation (6), where i, j, k represent the unit vectors of the x, y, and z axes of the chest accelerometer coordinate space respectively:

$$\vec{R}_{CN} = r_{CNx}\hat{i} + r_{CNy}\hat{j} + r_{CNz}\hat{k} \quad (6)$$

The angle between $\vec{R}_{CN}$ and $\vec{R}_G$ determined from DC values extracted from the chest accelerometer ACC waveform is given by equation (7):

$$\theta_{NG}[n]\arccos = \left(\frac{\vec{R}_G[n] \cdot \vec{R}_{CN}}{\|\vec{R}_G[n]\|\|\vec{R}_{CN}\|}\right) \quad (7)$$

The body-worn monitor determines the normal angle $\theta_{NG}$ and then compares it to a set of predetermined threshold angles to determine which position the patient is lying in, as shown in equation (8):

if $\theta_{NG} \leq 35°$ then Torso State=1, the patient is supine if $\theta_{NG} \geq 135°$ then Torso State=2, the patient is prone (8)

If the conditions in equation (8) are not met then the patient is assumed to be lying on their side. Whether they are lying on their right or left side is determined from the angle calculated between the horizontal torso vector and measured gravitational vectors, as described above.

The alignment of $\vec{R}_{CH}$ is determined using either an assumed orientation, or from the vector cross-product of $\vec{R}_{CV}$ and $\vec{R}_{CN}$ as given by equation (9), where i, j, k represent the unit vectors of the x, y, and z axes of the accelerometer coordinate space respectively. Note that the orientation of the calculated vector is dependent on the order of the vectors in the operation. The order below defines the horizontal axis as positive towards the right side of the patient's body.

$$\vec{R}_{CH} = r_{CVx}\hat{i} + r_{CVy}\hat{j} + r_{CVz}\hat{k} = \vec{R}_{CV} \times \vec{R}_{CN}$$

The angle $\theta_{HG}$ between $\vec{R}_{CH}$ and $\vec{R}_G$ is determined using equation (10):

$$\theta_{HG}[n] = \left(\frac{\vec{R}_G[n] \cdot \vec{R}_{CH}}{\|\vec{R}_G[n]\|\|\vec{R}_{CH}\|}\right) \quad (10)$$

The monitor compares this angle to a set of predetermined threshold angles to determine if the patient is lying on their right or left side, as given by equation (11):

if $\theta_{HG} \geq 90°$ then Torso State=3, the patient is on their right side if $\theta_{NG} < 90°$ then Torso State=4, the patient is on their left side (11)

Table 4 describes each of the above-described postures, along with a corresponding numerical torso state used to render, e.g., a particular icon on a remote computer:

TABLE 4

| postures and their corresponding torso states | |
|---|---|
| Posture | Torso State |
| standing upright | 0 |
| supine: lying on back | 1 |
| prone: lying on chest | 2 |
| lying on right side | 3 |
| lying on left side | 4 |
| undetermined posture | 5 |

Figure 26A:
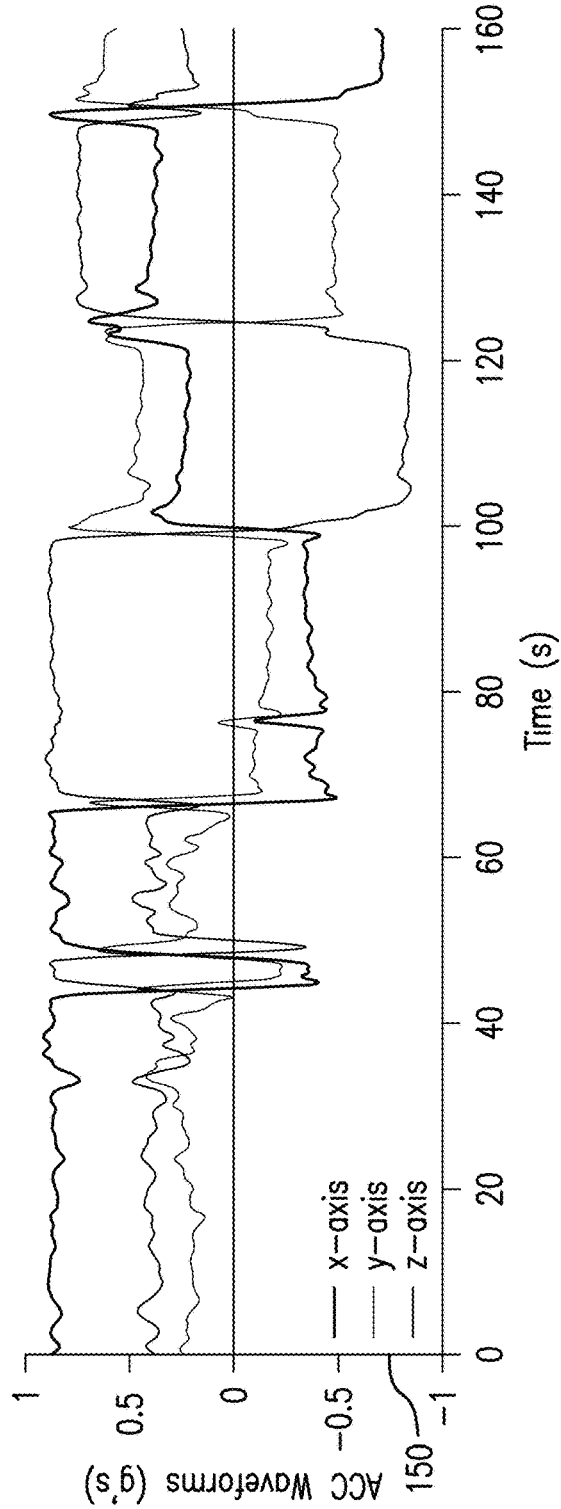
FIG. 26A shows a graph of time-dependent ACC waveforms measured from a patient's chest during different postures.
Figure 26B:
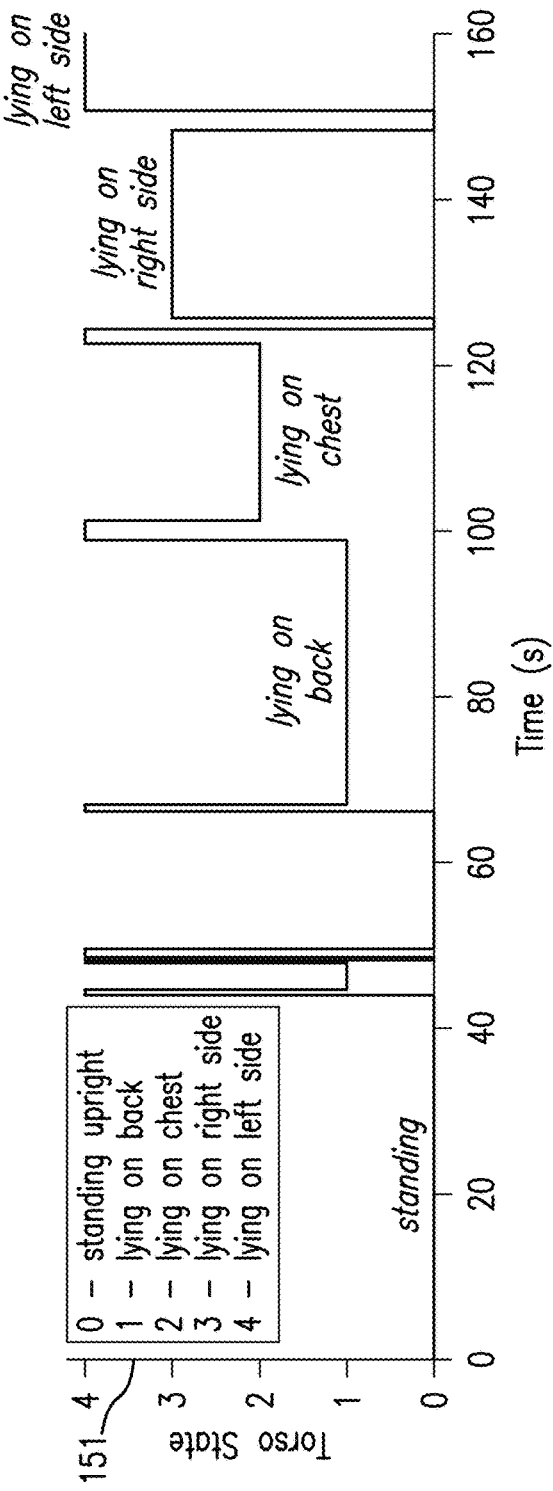
FIG. 26B shows a graph of time-dependent postures determined by processing the ACC waveforms of FIG. 26A with an algorithm and coordinate axis shown in FIG. 25.

FIGS. 26A and 26B show, respectively, graphs of time-dependent ACC waveforms measured along the x, y, and z-axes (FIG. 26A), and the torso states (i.e. postures; FIG. 26B) determined from these waveforms for a moving patient, as described above. As the patient moves, the DC values of the ACC waveforms measured by the chest accelerometer vary accordingly, as shown in FIG. 26A. The body-worn monitor processes these values as described above to continually determine $\vec{R}_G$ and the various quantized torso states for the patient, as shown in FIG. 26B. The torso states yield the patient's posture as defined in Table 4. For this study the patient rapidly alternated between standing, lying on their back, chest, right side, and left side within a time period of about 160 seconds. As described above, different alarm/alert conditions (e.g. threshold values) for vital signs can be assigned to each of these postures, or the specific posture itself may result in an alarm/alert. Additionally, the time-dependent properties of the graph can be analyzed (e.g. changes in the torso states can be counted) to determine, for example, how often the patient moves in their hospital bed. This number can then be equated to various metrics, such as a 'bed sore index' indicating a patient that is so stationary in their bed that lesions may result. Such a state could then be used to trigger an alarm/alert to the supervising medical professional.

Hardware for Measuring Respiratory Rate

FIGS. 27A and 27B show how the body-worn monitor 200 described above attaches to a patient 170 to measure RR, cNIBP, and other vital signs. These figures show two configurations of the system: FIG. 27A shows the system used during the indexing portion of the Composite Technique, and includes a pneumatic, cuff-based system 185, while FIG. 27B shows the system used for subsequent RR and cNIBP measurements. The indexing measurement typically takes about 60 seconds, and is typically performed once every 4 hours. Once the indexing measurement is complete the cuff-based system 185 is typically removed from the patient. The remainder of the time the monitor 200 performs the RR, SpO2 and cNIBP measurements.

Figure 28:
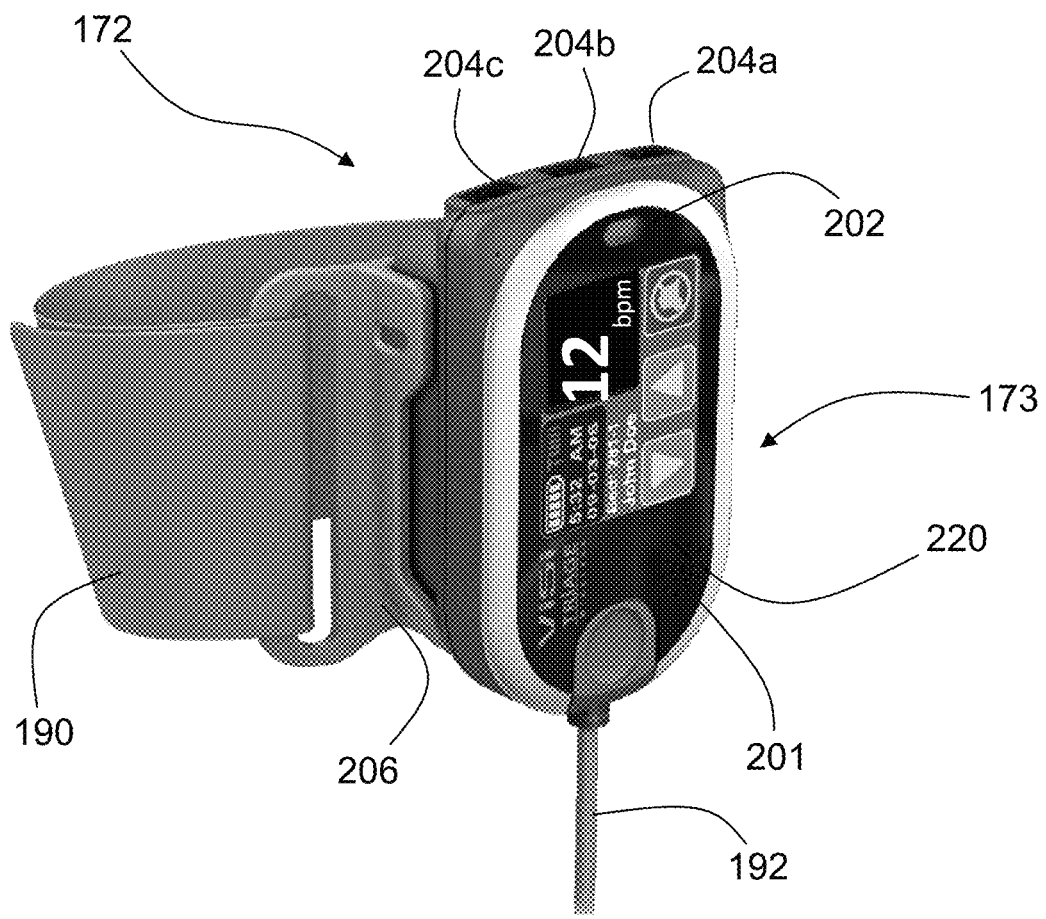
FIG. 28 shows a three-dimensional image of the wrist-worn transceiver used with the body-worn monitor of FIGS. 27A and 27B.

The body-worn monitor 200 features a wrist-worn transceiver 172, described in more detail in FIG. 28, featuring a touch panel interface 173 that displays RR, blood pressure values and other vital signs. A wrist strap 190 affixes the transceiver 172 to the patient's wrist like a conventional wristwatch. A flexible cable 192 connects the transceiver 172 to a pulse oximeter probe 194 that wraps around the base of the patient's thumb. During a measurement, the probe 194 generates a time-dependent PPG waveform which is processed along with an ECG to measure cNIBP, SpO2, and possible RR. This provides an accurate representation of blood pressure in the central regions of the patient's body, as described above.

To determine ACC waveforms the body-worn monitor 200 features three separate accelerometers located at different portions on the patient's arm and chest. The first accelerometer is surface-mounted on a circuit board in the wrist-worn transceiver 172 and measures signals associated with movement of the patient's wrist. As described above, this motion can also be indicative of that originating from the patient's fingers, which will affect the SpO2 measurement. The second accelerometer is included in a small bulkhead portion 196 included along the span of the cable 182. During a measurement, a small piece of disposable tape, similar in size to a conventional bandaid, affixes the bulkhead portion 196 to the patient's arm. In this way the bulkhead portion 196 serves two purposes: 1) it measures a time-dependent ACC waveform from the mid-portion of the patient's arm, thereby allowing their posture and arm height to be determined as described in detail above; and 2) it secures the cable 182 to the patient's arm to increase comfort and performance of the body-worn monitor 200, particularly when the patient is ambulatory. The third accelerometer is mounted in a bulkhead component 174 that connects through cables 180*a-c* to ECG electrodes 178*a-c*. As described in detail above, this accelerometer, which can also be mounted closer to the patient's abdomen, measures respiration-induced motion of the patient's chest and abdomen. These signals are then digitized, transmitted through the cable 182 to the wrist-worn transceiver 172, where they are processed with an algorithm as described above to determine RR.

The cuff-based module 185 features a pneumatic system 176 that includes a pump, valve, pressure fittings, pressure sensor, analog-to-digital converter, microcontroller, and rechargeable Li:ion battery. During an indexing measurement, the pneumatic system 176 inflates a disposable cuff 184 and performs two measurements according to the Composite Technique: 1) it performs an inflation-based measurement of oscillometry to determine values for SYS, DIA, and MAP; and 2) it determines a patient-specific relationship between PTT and MAP. These measurements are described in detail in the above-referenced patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138,194; filed Jun. 12, 2008), the contents of which have been previously incorporated herein by reference.

The cuff 184 within the cuff-based pneumatic system 185 is typically disposable and features an internal, airtight bladder that wraps around the patient's bicep to deliver a uniform pressure field. During the indexing measurement, pressure values are digitized by the internal analog-to-digital converter, and sent through a cable 186 according to a CAN protocol, along with SYS, DIA, and MAP blood pressures, to the wrist-worn transceiver 172 for processing as described above. Once the cuff-based measurement is complete, the cuff-based module 185 is removed from the patient's arm and the cable 186 is disconnected from the wrist-worn transceiver 172. cNIBP is then determined using PTT, as described in detail above.

To determine an ECG, the body-worn monitor 200 features a small-scale, three-lead ECG circuit integrated directly into the bulkhead 174 that terminates an ECG cable 182. The ECG circuit features an integrated circuit that collects electrical signals from three chest-worn ECG electrodes 178*a-c* connected through cables 180*a-c*. As described above, the ECG electrodes 178*a-c* are typically disposed in a conventional Einthoven's Triangle configuration which is a triangle-like orientation of the electrodes 178*a-c* on the patient's chest that features three unique ECG vectors. From these electrical signals the ECG circuit determines up to three ECG waveforms, which are digitized using an analog-to-digital converter mounted proximal to the ECG circuit, and sent through the cable 182 to the wrist-worn transceiver 172 according to the CAN protocol. There, the ECG and PPG waveforms are processed to determine the patient's blood pressure. Heart rate and RR are determined directly from the ECG waveform using known algorithms, such as those described above. The cable bulkhead 174 also includes an accelerometer that measures motion associated with the patient's chest as described above.

As described above, there are several advantages of digitizing ECG and ACC waveforms prior to transmitting them through the cable 182. First, a single transmission line in the cable 182 can transmit multiple digital waveforms, each generated by different sensors. This includes multiple ECG waveforms (corresponding, e.g., to vectors associated with three, five, and twelve-lead ECG systems) from the ECG circuit mounted in the bulkhead 174, along with waveforms associated with the x, y, and z-axes of accelerometers mounted in the bulkheads 174, 196. More sophisticated ECG circuits (e.g. five and twelve-lead systems) can plug into the wrist-worn transceiver to replace the three-lead system shown in FIGS. 27A and 27B.

FIG. 28 shows a close-up view of the wrist-worn transceiver 172. As described above, it attaches to the patient's wrist using a flexible strap 190 which threads through two D-ring openings in a plastic housing 206. The transceiver 172 features a touchpanel display 220 that renders a GUI 173 which is altered depending on the viewer (typically the patient or a medical professional). Specifically, the transceiver 172 includes a small-scale infrared barcode scanner 202 that, during use, can scan a barcode worn on a badge of a medical professional. The barcode indicates to the transceiver's software that, for example, a nurse or doctor is viewing the user interface. In response, the GUI 173 displays vital sign data and other medical diagnostic information appropriate for medical professionals. Using this GUI 173, the nurse or doctor, for example, can view the vital sign information, set alarm parameters, and enter information about the patient (e.g. their demographic information, medication, or medical condition). The nurse can press a button on the GUI 173 indicating that these operations are complete. At this point, the display 220 renders an interface that is more appropriate to the patient, such as time of day and battery power.

The transceiver 172 features three CAN connectors 204*a-c* on the side of its upper portion, each which supports the CAN protocol and wiring schematics, and relays digitized data to the internal CPU. Digital signals that pass through the CAN connectors include a header that indicates the specific signal (e.g. ECG, ACC, or pressure waveform from the cuff-based module) and the sensor from which the signal originated. This allows the CPU to easily interpret signals that arrive through the CAN connectors 204*a-c*, such as those described above corresponding to RR, and means that these connectors are not associated with a specific cable.

Any cable connecting to the transceiver can be plugged into any connector 204a-c. As shown in FIG. 27A, the first connector 204a receives the cable 182 that transports a digitized ECG waveform determined from the ECG circuit and electrodes, and digitized ACC waveforms measured by accelerometers in the cable bulkhead 174 and the bulkhead portion 196 associated with the ECG cable 182.

The second CAN connector 204b shown in FIG. 28 receives the cable 186 that connects to the pneumatic cuff-based system 185 used for the pressure-dependent indexing measurement (shown in FIG. 27A). This connector 204b receives a time-dependent pressure waveform delivered by the pneumatic system 185 to the patient's arm, along with values for SYS, DIA, and MAP values determined during the indexing measurement. The cable 186 unplugs from the connector 204b once the indexing measurement is complete, and is plugged back in after approximately four hours for another indexing measurement.

The final CAN connector 204c can be used for an ancillary device, e.g. a glucometer, infusion pump, body-worn insulin pump, ventilator, or et-CO2 delivery system. As described above, digital information generated by these systems will include a header that indicates their origin so that the CPU can process them accordingly.

The transceiver includes a speaker 201 that allows a medical professional to communicate with the patient using a voice over Internet protocol (VOIP). For example, using the speaker 201 the medical professional could query the patient from a central nursing station or mobile phone connected to a wireless, Internet-based network within the hospital. Or the medical professional could wear a separate transceiver similar to the shown in FIG. 28, and use this as a communication device. In this application, the transceiver 172 worn by the patient functions much like a conventional cellular telephone or 'walkie talkie': it can be used for voice communications with the medical professional and can additionally relay information describing the patient's vital signs and motion. The speaker can also enunciate pre-programmed messages to the patient, such as those used to calibrate the chest-worn accelerometers for a posture calculation, as described above.

Other Embodiments of the Invention

RR can also be calculated using a combination of ACC, ECG, PPG, IP, and other signals using algorithms that differ from those described above. For example, these signals can be processed with an averaging algorithm, such as one using a weighted average, to determine a single waveform that can then be processed to determine RR. Or the ACC waveform can be used alone, without being integrated in an adaptive filtering algorithm, to determine RR without relying on IP. In this case the ACC waveform is filtered with a simple bandpass filter, e.g. a finite impulse response filter, with a set passband (e.g. 0.01→5 Hz). Similarly, multiple ACC waveforms, such as those measured along axes (e.g. the x or y-axes) orthogonal to the vector normal to the patient's chest (i.e. the z-axis), can be processed with or without adaptive filtering to determine RR. In this case the waveforms may be averaged together with a weighted average to generate a single waveform, which is then filtered, derivatized, and signal processed as described above with reference to FIG. 3 to determine RR. Similarly, envelopes associated with the ECG and PPG waveforms can be processed in a similar manner to determine RR. In still other embodiments, other sensors, such as ultra wide-band radar or acoustic sensors, can detect signals indicative of RR and used with ACC or IP waveforms and the adaptive filtering approach described above to determine RR. Here, the alternative sensors are typically used to replace measurement of the IP waveform, although they can also be used to replace measurement of the ACC waveform. An acoustic sensor suitable for this application is described, for example, in the following co-pending patent application, the contents of which are incorporated herein by reference: DEVICE FOR DETERMINING RESPIRATORY RATE AND OTHER VITAL SIGNS (U.S. Ser. No. 12/171,886; filed Jul. 12, 2008).

In addition to those methods described above, the body-worn monitor can use a number of additional methods to calculate blood pressure and other properties from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S.S.N; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other measurement techniques, such as conventional oscillometry measured during deflation, can be used to determine SYS for the above-described algorithms. Additionally, processing units and probes for measuring pulse oximetry similar to those described above can be modified and worn on other portions of the patient's body. For example, pulse oximetry probes with finger-ring configurations can be worn on fingers other than the thumb. Or they can be modified to attach to other conventional sites for measuring SpO2, such as the ear, forehead, and bridge of the nose. In these embodiments the processing unit can be worn in places other than the wrist, such as around the neck (and supported, e.g., by a lanyard) or on the patient's waist (supported, e.g., by a clip that attaches to the patient's belt). In still other embodiments the probe and processing unit are integrated into a single unit.

In other embodiments, a set of body-worn monitors can continuously monitor a group of patients, wherein each patient in the group wears a body-worn monitor similar to those described herein. Additionally, each body-worn monitor can be augmented with a location sensor. The location sensor includes a wireless component and a location-processing component that receives a signal from the wireless component and processes it to determine a physical location of the patient. A processing component (similar to that described above) determines from the time-dependent waveforms at least one vital sign, one motion parameter, and an alarm parameter calculated from the combination of this information. A wireless transceiver transmits the vital sign, motion parameter, location of the patient, and alarm parameter through a wireless system. A remote computer system featuring a display and an interface to the wireless system receives the information and displays it on a user interface for each patient in the group.

In embodiments, the interface rendered on the display at the central nursing station features a field that displays a map corresponding to an area with multiple sections. Each section corresponds to the location of the patient and includes, e.g., the patient's vital signs, motion parameter, and alarm parameter. For example, the field can display a map corresponding to an area of a hospital (e.g. a hospital bay or emergency room), with each section corresponding to a specific bed, chair, or general location in the area. Typically the display renders graphical icons corresponding to the motion and alarm parameters for each patient in the group. In other embodiments, the body-worn monitor includes a graphical display that renders these parameters directly on the patient.

Typically the location sensor and the wireless transceiver operate on a common wireless system, e.g. a wireless system based on 802.11, 802.15.4, or cellular protocols. In this case a location is determined by processing the wireless signal with one or more algorithms known in the art. These include, for example, triangulating signals received from at least three different base stations, or simply estimating a location based on signal strength and proximity to a particular base station. In still other embodiments the location sensor includes a conventional global positioning system (GPS).

The body-worn monitor can include a first voice interface, and the remote computer can include a second voice interface that integrates with the first voice interface. The location sensor, wireless transceiver, and first and second voice interfaces can all operate on a common wireless system, such as one of the above-described systems based on 802.11 or cellular protocols. The remote computer, for example, can be a monitor that is essentially identical to the monitor worn by the patient, and can be carried or worn by a medical professional. In this case the monitor associated with the medical professional features a GUI wherein the user can select to display information (e.g. vital signs, location, and alarms) corresponding to a particular patient. This monitor can also include a voice interface so the medical professional can communicate directly with the patient.

Figure 29B:
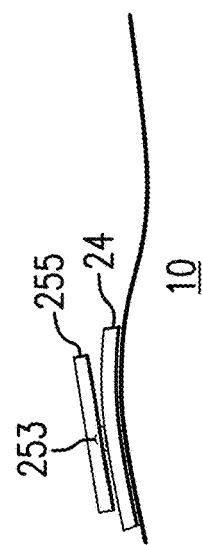
FIG. 29B is a schematic, cross-sectional view of the sensor unit of FIG. 29A connected to the patient's abdomen with an electrode.
Figure 29A:
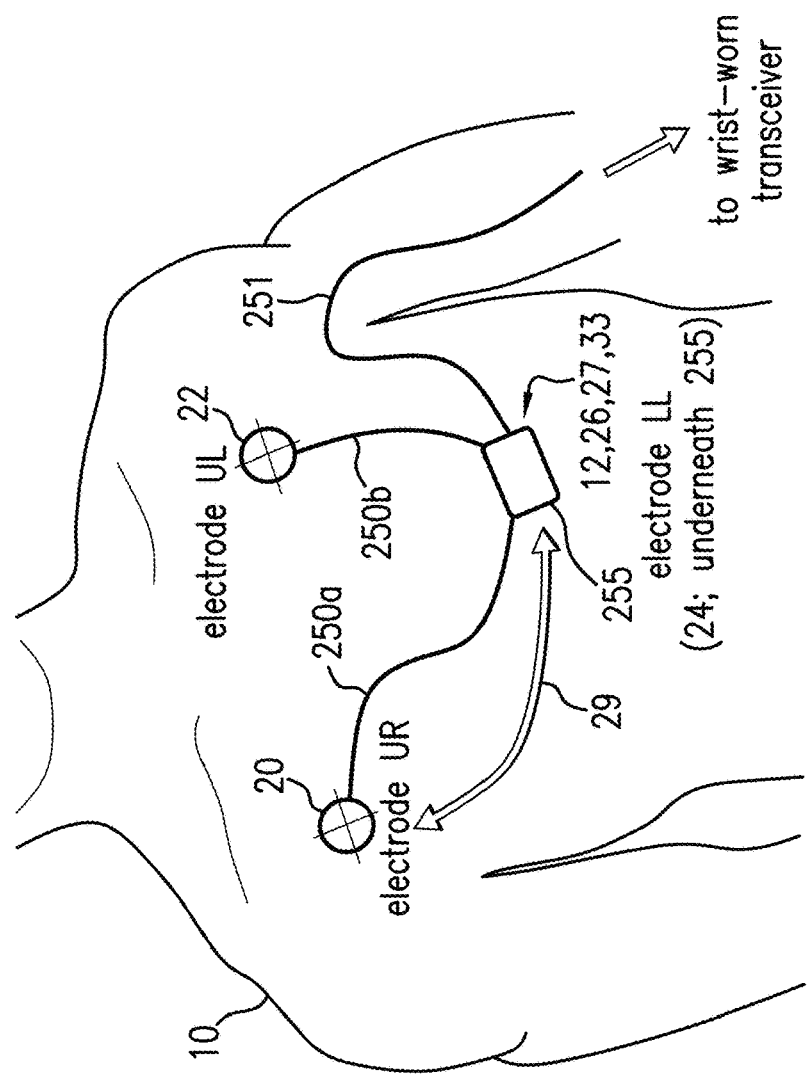
FIG. 29A is a schematic view of a patient wearing an alternate embodiment of the invention featuring a sensor unit for measuring IP and ACC waveforms that connects directly to the patient's abdomen with an electrode.

FIGS. 29A, 29B show yet another alternate embodiment of the invention wherein a sensor unit 255 attaches to the abdomen of a patient 10 using an electrode 24 normally attached to the lower left-hand portion of the patient's torso. Specifically, the sensor unit 255 includes a connector 253 featuring an opening that receives the metal snap or rivet present on most disposable ECG electrodes. Connecting the connector 245 to the electrode's rivet holds the sensor unit 255 in place. This configuration reduces the number of cables in the body-worn monitor, and additionally secures an accelerometer 12 to the patient's abdomen. This is typically the part of their torso that undergoes the greatest motion during respiration, and thus generates ACC waveforms with the highest possible signal-to-noise ratio. Also contained within the sensor unit 255 are the ECG circuit 26, the IP circuit 27, and a temperature sensor 33.

To measure IP and ECG waveforms, the sensor unit 255 connects through cables 250a, 250b to electrodes 20, 22 attached, respectively, to the upper right-hand and left-hand portions of the patient's torso. This system measures RR using the adaptive filtering approach described above, and has the additional advantage of measuring a relatively large ACC signals indicating respiration-induced motions of the patient's abdomen. As described above, these signals are typically generated by the z-axis of the accelerometer 12, which is normal to the patient's torso. ACC signals along the x and y-axes can be additionally processed to determine the patient's posture and activity level, as described above. Once RR and these motion-related properties are measured, a transceiver in the sensor unit (not shown in the figure) transmits them in the form of a digital data stream through a cable 251 to the wrist-worn transceiver for further processing.

Still other embodiments are within the scope of the following claims.

What is claimed is:

1. A body-worn system for monitoring respiratory rate from a patient, comprising:
   a housing configured to be mounted on the patient's torso, an accelerometer system contained within the housing and comprising: (i) a first accelerometer configured to generate a first set of time-dependent digital motion waveforms indicative of movement of the chest or abdomen, (ii) an impedance pneumography system configured to generate a time-dependent digital impedance pneumography waveform, and (iii) an electrocardiogram (ECG) system configured to generate a time-dependent digital ECG waveform;
   a second accelerometer configured to generate a second set of time-dependent digital motion waveforms indicative of motions of the patient's upper arm;
   a third accelerometer configured to generate a third set of time-dependent digital motion waveforms along three orthogonal axes indicative of motions of the patient's lower arm;
   a processing system configured to be mounted on the patient's wrist, wherein the processing system comprises a processor and a cable port operably connected to the processor; and
   a cable that operably connects to each of the first and second accelerometers, the impedance pneumography system, and the ECG system and comprising a terminal connector which inserts into the cable port and thereby provides a single common transmission line for communication of the first set of time-dependent digital motion waveforms, the second set of time-dependent digital motion waveforms, the time-dependent digital impedance pneumography waveform and the time-dependent digital ECG waveform to the processing component, wherein each of the first set of time-dependent digital motion waveforms, the second set of time-dependent digital motion waveforms, the time-dependent digital impedance pneumography waveform and the time-dependent digital ECG waveform are transmitted as data streams comprising a header portion and a data portion, the header portion indicating the specific signal type of the data and the sensor from which the data originates;

wherein the processing system is configured to receive and process the first set of time-dependent digital motion waveforms, the second set of time-dependent digital motion waveforms, the time-dependent digital impedance pneumography waveform and the time-dependent digital ECG waveform and thereby determine the patient's respiratory rate and the patient's posture, activity level, and degree of motion.

* * * * *